(12) United States Patent
Saito et al.

(10) Patent No.: US 8,440,187 B2
(45) Date of Patent: May 14, 2013

(54) USE APPLICATION OF SUGAR CHAIN-RECOGNIZING RECEPTOR

(75) Inventors: Takashi Saito, Kanagawa (JP); Sho Yamasaki, Kanagawa (JP)

(73) Assignee: Riken, Wako-shi (JP)

( * ) Notice: Subject to any disclaimer, the term of this patent is extended or adjusted under 35 U.S.C. 154(b) by 0 days.

(21) Appl. No.: 13/054,556

(22) PCT Filed: Jul. 17, 2009

(86) PCT No.: PCT/JP2009/063008
§ 371 (c)(1),
(2), (4) Date: Apr. 4, 2011

(87) PCT Pub. No.: WO2010/008084
PCT Pub. Date: Jan. 21, 2010

(65) Prior Publication Data
US 2011/0177084 A1  Jul. 21, 2011

(30) Foreign Application Priority Data
Jul. 17, 2008 (JP) .................................. 2008-186570

(51) Int. Cl.
*A61K 39/395* (2006.01)
(52) U.S. Cl.
USPC .................... 424/130.1; 424/133.1; 424/143.1
(58) Field of Classification Search .......................... None
See application file for complete search history.

(56) References Cited

U.S. PATENT DOCUMENTS
2005/0019860 A1   1/2005  Akira et al.
2007/0160578 A1*  7/2007  Waldmann et al. .......... 424/85.2

FOREIGN PATENT DOCUMENTS
JP   2001-112482 A   4/2001
WO  WO 2006/105252 A2  10/2006

OTHER PUBLICATIONS

Heitmann, L., et al., Mincle is not essential for controlling *Mycobacterium tuberculosis* infection. Immunobiology (2012), http://dx.doi.org/10.1016/j.imbio.2012.06.005. pp. 1-11.*
Bugarcic et al., *Glycobiology*, 18(9): 679-685 (2008).
European Patent Office, Extended European Search Report in European Patent Application No. 09798008.0 (Apr. 4, 2012).
Fadok et al., *J. Clin. Invest.*, 108(7): 957-962 (2001).
Kitamura et al., *J. Immunol.*, 178: 480-488 (2007).
Japanese Patent Office, International Search Report in International Patent Application PCT/JP2009/063008 (Sep. 1, 2009) English.
Lorimore et al., *Oncogene*, 20: 7085-7095 (2001).
Marshak-Rothstein, *Nat. Rev. Immunol.*, 6: 823-835 (2006).
Matsumoto et al., *J. Immunol.*, 163: 5039-5048 (1999).
Robinson et al., *Nat. Immunol.*, 7(12): 1258-1265 (2006).
Wells et al., *J. Immunol.*, 180: 7404-7413 (2008).
Yamasaki et al., *Nat. Immunol.*, 9(10): 1179-1188 (2008).

* cited by examiner

*Primary Examiner* — Maher Haddad
(74) *Attorney, Agent, or Firm* — Leydig, Voit & Mayer, Ltd.

(57) ABSTRACT

Provided are a novel means for regulating inflammatory reactions by regulating the signaling in inflammatory responses caused by non-homeostatic cell death, specifically an anti-inflammatory agent comprising a substance that inhibits the expression of Mincle or the interaction of Mincle and SAP130 or FcRγ, a screening method for a substance that regulates inflammatory reactions, comprising contacting Mincle or a fragment containing an extracellular region thereof and SAP130 in the presence and absence of a test substance, and comparing the degrees of the interaction of Mincle or the fragment thereof and SAP130 under the two conditions, a method of detecting non-homeostatic cell death, comprising measuring the amount of SAP130 in a sample collected from a subject animal, and the like.

13 Claims, 13 Drawing Sheets

FIG. 2
a
transmembrane region
| | |
|---|---|
| mMincle | LSWTIAGASILFLSGCFITRCVV |
| rMincle | LSWTMAGASILFLSVCFITRCVV |
| hMincle | FLWTVAGIPILFLSACFITRCVV |
b
IP: anti-Flag
| Mincle | + | + | + |
| Flag-DAP12 | + | − | − |
| Flag-DAP10 | − | + | − |
| Flag-FcRγ | − | − | + |
anti-Mincle
anti-Flag
Total lysates
anti-Mincle
c
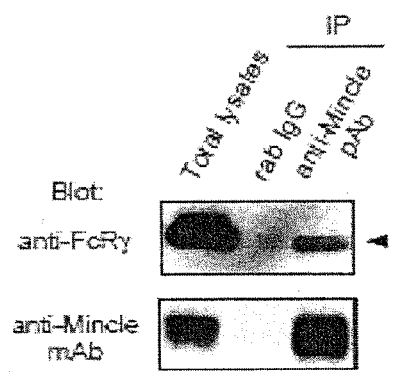
d
IP: anti-FcRγ
| Mincle-Flag | + | WT | R42I |
| FcRγ | + | + | + |
anti-Flag
anti-FcRγ
IP: anti-Flag
anti-FcRγ
anti-Flag
e
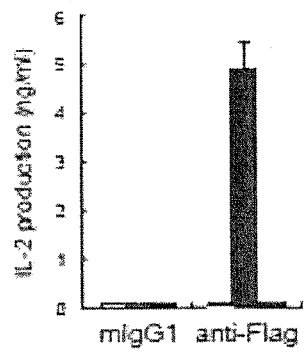

FIG. 7 a

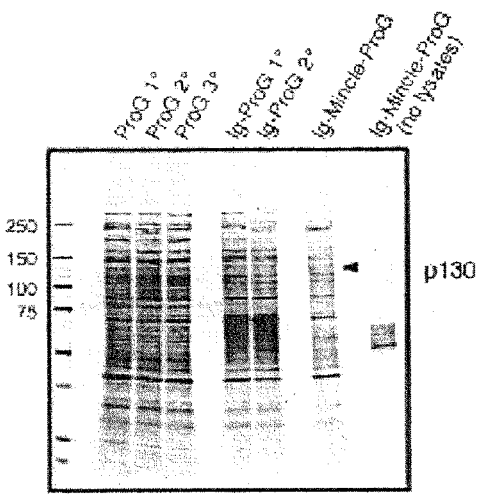

p130 b

| Peptide | Observed | Theoretical | Delta | Head | Tail | Corresponding sequence | Comment |
|---|---|---|---|---|---|---|---|
| AP 1 | 853.528 | 853.539 | 0.013 | 532 | 537 | [K]RPNNEWK[T] | |
| AP 2 | 959.484 | 959.495 | 0.011 | 102 | 109 | [K]IHQETFGK[S] | |
| AP 3 | 1143.65 | 1143.640 | 0.010 | 27 | 36 | [K]QQEIVVSRGK[I] | |
| AP 4 | 1465.845 | 1465.838 | 0.007 | 37 | 49 | [R]ILELLRPDPNTGK[V] | |
| AP 5 | 1699.862 | 1699.85 | 0.012 | 1192 | 1206 | [K]NVSEELDRTIPPEVSK[K] | |
| AP 6 | 2109.902 | 2109.922 | 0.020 | 1172 | 1189 | [K]NVIDGDLCEQFNSMEPNK[Q] | 0Met-ox |
| AP 7 | 2125.897 | 2125.917 | 0.020 | 1172 | 1189 | [K]NVIDGDLCEQFNSMEPNK[Q] | 1Met-ox |
| AP 8 | 2338.233 | 2338.229 | 0.004 | 76 | 96 | [K]DYIVVGSDSGRIVIL EYQPSK[N] | |
| AP 9 | 2348.348 | 2348.334 | 0.014 | 943 | 965 | [K]TPVEEVPAAIAPFQGRVLGVGK[L] | |
| AP 10 | 2900.326 | 2900.321 | 0.005 | 1050 | 1074 | [K]FGNICVVRLPPNTNDEVDEDPTGNK[A] | | c

```
   1 MFLYNLTLQR ATGISFAIHG NFSGTKQQEI VVSRGKILEL LRFDPNTGKV HTLLTVEVFG
  61 VIRSLMAFRL TGGTKDYIVV GSDSGRIVIL EYQPSKNMFE KIHQETFGKS GCRRIVPGQF
 121 LAVDPHGHAV HISAIEKQRL VYTLNRDAJA RLTISSPLEA HKANTLVYHV VGVDVGFSNP
 181 MFACLEMDYE EADNDPTGEA AANTQQILTF YELDLGLNHV VRKYSEPLEE SGNFLITVPG
 241 CSDGPSGVLI CSENYITYKN FGDQPDIRCP IPRRNDLDD PERCMIFVCS ATHNTKSHPF
 301 FLAQTEQGDI FKITLETDED MVTEIRLKYF DTVPVAAAMC VLKTGFLFVA SFFGNHYLYQ
 361 IAHLGDDDEE PEFSSAMPLE EGDTFFFQPR PLKHLVLVDE LDSLSPILPC QIADLANEDT
 421 PQLYVACGRG PRSSLRVLRH GLEVSRMAVS ELPGNPHAVW TVRRHISDEF DAYIIVSFVH
 481 ATLVLSIGET VEEVTDSGFL GTTPTLSCSL LGDDALVQVY PDGIRHIRAD KSVHEWKTPG
 541 KETIVKCAVN QRQWVIALTG GELAYFEMDP SGGLNEYTER KEMSADVVCM SLAHVPPGED
 601 RSRFLAVGLV DNTVRIISLD PSDCLQPLSN QALPAQPESL CIVEMGGTEK QDELGERGSI
 661 GFLYLNIGLQ NGVLLRTVLD PVTGDLSDTR TRYLGSPPVR LFRVRMQGQE AVLAMSSRSW
 721 LSYSYQSRFH LTPLSYETLE PASGPASEQC PEGIVAISTM TLRILALERL GAVFHQVAPP
 781 LGYTPRKFVI HPFSWNLIYI STGHNAYTEA TKAQSRQQMA SEMYSAAGED ESELAASMAA
 841 AFLNEHLPES IFGAPKAGHG QWASVIRVMN PIQGNTLDLV QLEQNEAAFS VAVCRFSNTG
 901 EDWYVLVGVA HDLILSPRSV AGGFVYTYRL VNNGEKLEFL HKTPVEEVPA AIAPFQGRVL
 961 IGVGKLLRVY DLGKKKLLRK CENKHIANYI SGIQTIGERV IVSDVQESFI WVRYKRHENQ
1021 LIIPADDTYP HWVTTASLLD EDTVAGADKF QNICVVRLPP NTNDEVDEDP TGNKALNDRG
1081 LLNGASQKAE VIMNYEVGET VLSLQKTTLI PGGSESLVYT TLSGGIGILV PFTSHEDRDF
1141 PQNVEMHLRS EHPPLCGRDH LSFRSYYPPV KNVIDGDLCE QPNSMEPHKQ KSVSEELDRT
1201 PPEVSKKLED IRTRYAF
```

FIG. 9
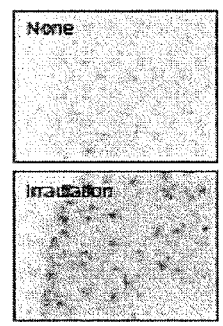
a
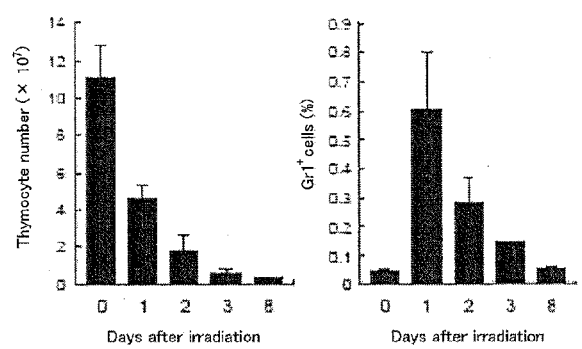
b
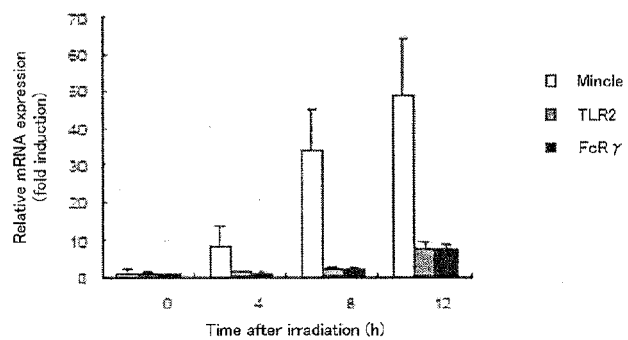
c
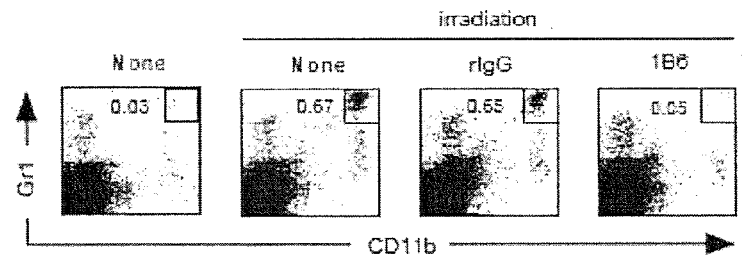
d
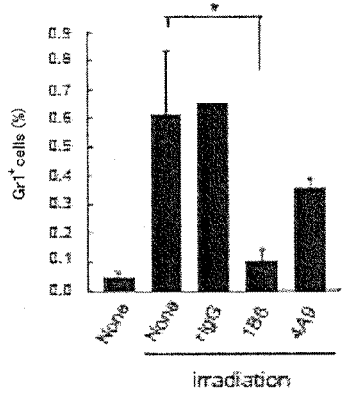
e
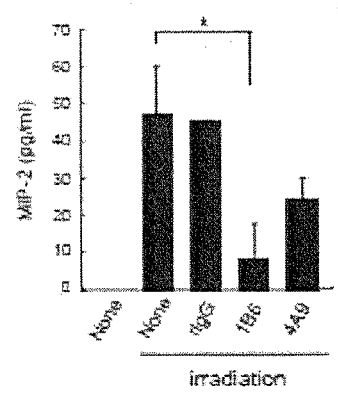
f FIG. 10
a
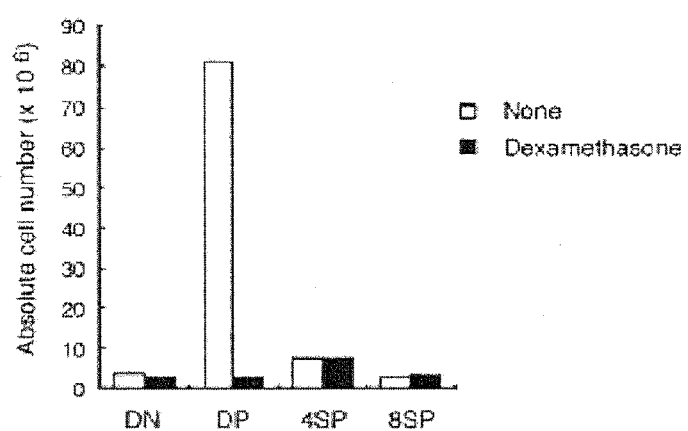
b
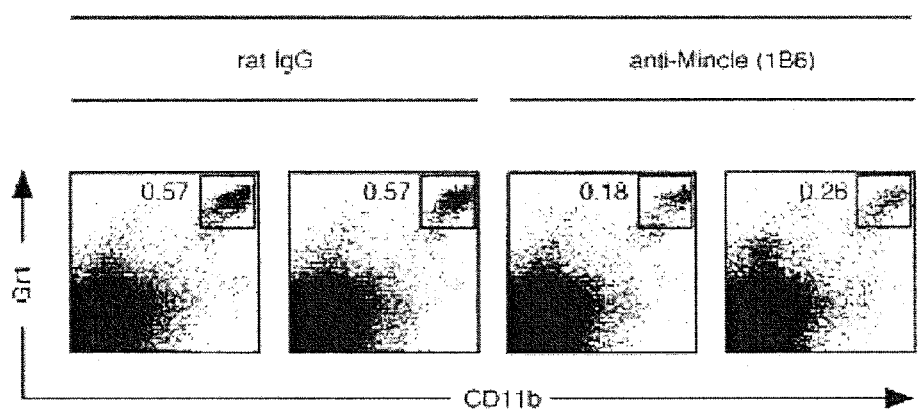

FIG. 11
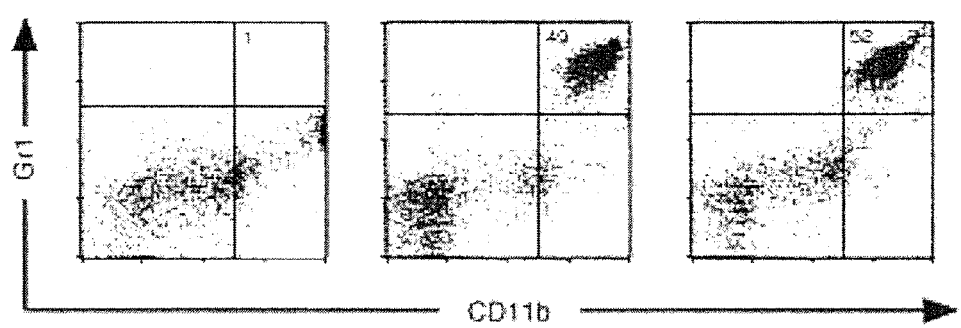
a
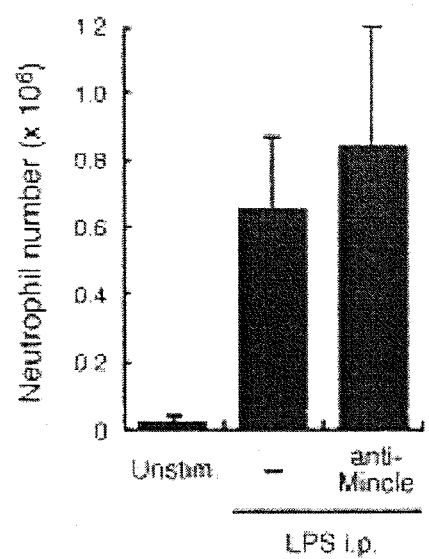
b

FIG. 12
a
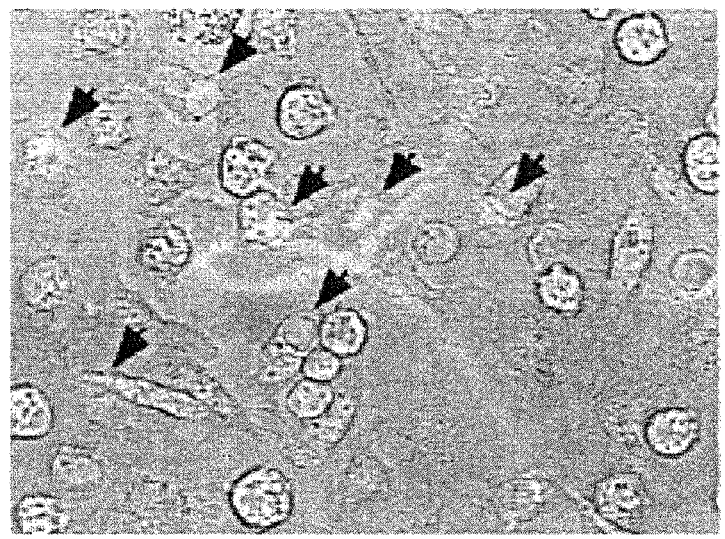
b
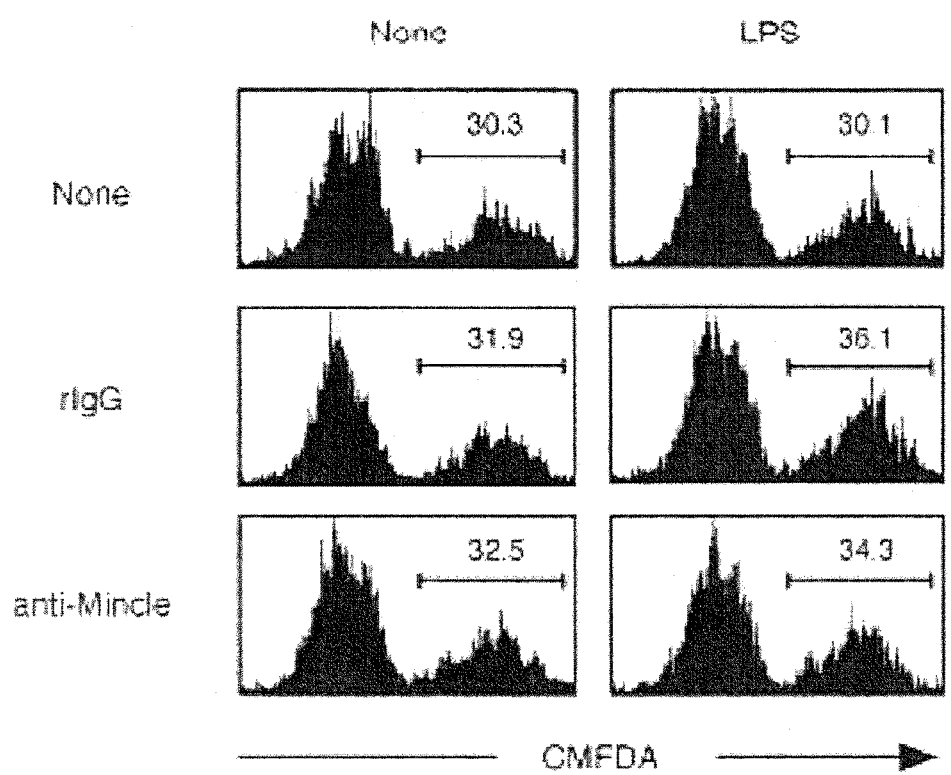

FIG. 13
a U2 snRNPs
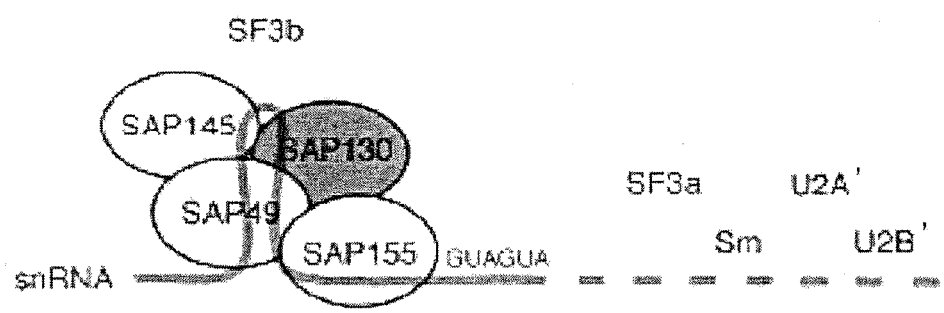
b
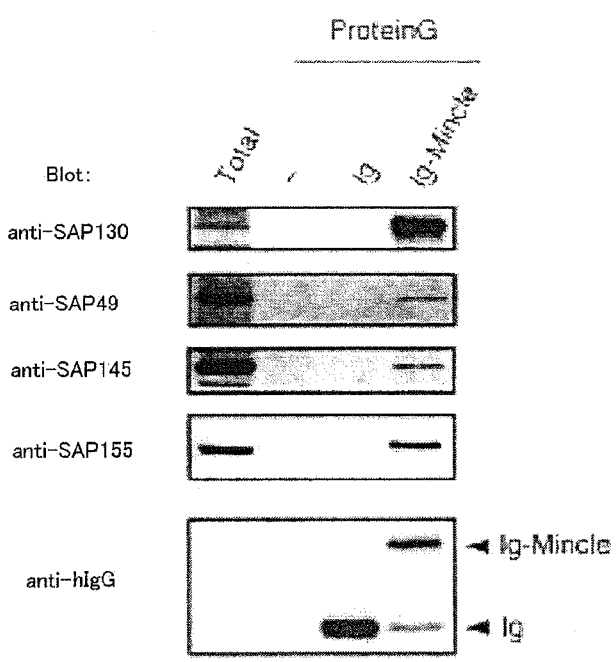

SEQUENCE LISTING

```
<160> NUMBER OF SEQ ID NOS: 39

<210> SEQ ID NO 1
<211> LENGTH: 657
<212> TYPE: DNA
<213> ORGANISM: Homo sapiens
<220> FEATURE:
<221> NAME/KEY: CDS
<222> LOCATION: (1)..(657)

<400> SEQUENCE: 1 atg aat tca tct aaa tca tct gaa aca caa tgc aca gag aga gga tgc      48
Met Asn Ser Ser Lys Ser Ser Glu Thr Gln Cys Thr Glu Arg Gly Cys
1               5                  10                  15 ttc tct tcc caa atg ttc tta tgg act gtt gct ggg atc ccc atc cta      96
Phe Ser Ser Gln Met Phe Leu Trp Thr Val Ala Gly Ile Pro Ile Leu
            20                  25                  30 ttt ctc agt gcc tgt ttc atc acc aga tgt gtt gtg aca ttt cgc atc     144
Phe Leu Ser Ala Cys Phe Ile Thr Arg Cys Val Val Thr Phe Arg Ile
        35                  40                  45 ttt caa acc tgt gat gag aaa aag ttt cag cta cct gag aat ttc aca     192
Phe Gln Thr Cys Asp Glu Lys Lys Phe Gln Leu Pro Glu Asn Phe Thr
    50                  55                  60 gag ctc tcc tgc tac aat tat gga tca ggt tca gtc aag aat tgt tgt     240
Glu Leu Ser Cys Tyr Asn Tyr Gly Ser Gly Ser Val Lys Asn Cys Cys
65                  70                  75                  80 cca ttg aac tgg gaa tat ttt caa tcc agc tgc tac ttt tct act         288
Pro Leu Asn Trp Glu Tyr Phe Gln Ser Ser Cys Tyr Phe Phe Ser Thr
                85                  90                  95 gac acc att tcc tgg gcg tta agt tta aag aac tgc tca gcc atg ggg     336
Asp Thr Ile Ser Trp Ala Leu Ser Leu Lys Asn Cys Ser Ala Met Gly
            100                 105                 110
```

```
gct cac ctg gtg gtt atc aac tca cag gag gag cag gaa ttc ctt tcc    384
Ala His Leu Val Val Ile Asn Ser Gln Glu Glu Gln Glu Phe Leu Ser
        115                 120                 125 tac aag aaa cct aaa atg aga gag ttt ttt att gga ctg tca gac cag    432
Tyr Lys Lys Pro Lys Met Arg Glu Phe Phe Ile Gly Leu Ser Asp Gln
130                 135                 140 gtt gtc gag ggt cag tgg caa tgg gtg gac ggc aca cct ttg aca aag    480
Val Val Glu Gly Gln Trp Gln Trp Val Asp Gly Thr Pro Leu Thr Lys
145                 150                 155                 160 tct ctg agc ttc tgg gat gta ggg gag ccc aac aac ata gct acc ctg    528
Ser Leu Ser Phe Trp Asp Val Gly Glu Pro Asn Asn Ile Ala Thr Leu
            165                 170                 175 gag gac tgt gcc acc atg aga gac tct tca aac cca agg caa aat tgg    576
Glu Asp Cys Ala Thr Met Arg Asp Ser Ser Asn Pro Arg Gln Asn Trp
        180                 185                 190 aat gat gta acc tgt ttc ctc aat tat ttt cgg att tgt gaa atg gta    624
Asn Asp Val Thr Cys Phe Leu Asn Tyr Phe Arg Ile Cys Glu Met Val
    195                 200                 205 gga ata aat cct ttg aac aaa gga aaa tct ctt                        657
Gly Ile Asn Pro Leu Asn Lys Gly Lys Ser Leu
210                 215

<210> SEQ ID NO 2
<211> LENGTH: 219
<212> TYPE: PRT
<213> ORGANISM: Homo sapiens

<400> SEQUENCE: 2

Met Asn Ser Ser Lys Ser Ser Glu Thr Gln Cys Thr Glu Arg Gly Cys
1               5                   10                  15

Phe Ser Ser Gln Met Phe Leu Trp Thr Val Ala Gly Ile Pro Ile Leu
            20                  25                  30

Phe Leu Ser Ala Cys Phe Ile Thr Arg Cys Val Val Thr Phe Arg Ile
        35                  40                  45

Phe Gln Thr Cys Asp Glu Lys Lys Phe Gln Leu Pro Glu Asn Phe Thr
    50                  55                  60

Glu Leu Ser Cys Tyr Asn Tyr Gly Ser Gly Ser Val Lys Asn Cys Cys
65                  70                  75                  80

Pro Leu Asn Trp Glu Tyr Phe Gln Ser Ser Cys Tyr Phe Phe Ser Thr
                85                  90                  95

Asp Thr Ile Ser Trp Ala Leu Ser Leu Lys Asn Cys Ser Ala Met Gly
            100                 105                 110

Ala His Leu Val Val Ile Asn Ser Gln Glu Glu Gln Glu Phe Leu Ser
        115                 120                 125

Tyr Lys Lys Pro Lys Met Arg Glu Phe Phe Ile Gly Leu Ser Asp Gln
    130                 135                 140

Val Val Glu Gly Gln Trp Gln Trp Val Asp Gly Thr Pro Leu Thr Lys
145                 150                 155                 160

Ser Leu Ser Phe Trp Asp Val Gly Glu Pro Asn Asn Ile Ala Thr Leu
                165                 170                 175

Glu Asp Cys Ala Thr Met Arg Asp Ser Ser Asn Pro Arg Gln Asn Trp
            180                 185                 190

Asn Asp Val Thr Cys Phe Leu Asn Tyr Phe Arg Ile Cys Glu Met Val
        195                 200                 205

Gly Ile Asn Pro Leu Asn Lys Gly Lys Ser Leu
    210                 215
```

```
<210> SEQ ID NO 3
<211> LENGTH: 3651
<212> TYPE: DNA
<213> ORGANISM: Homo sapiens
<220> FEATURE:
<221> NAME/KEY: CDS
<222> LOCATION: (1)..(3651)

<400> SEQUENCE: 3
```

| | | | | | | | | | | | | | | | | |
|---|---|---|---|---|---|---|---|---|---|---|---|---|---|---|---|---|
| atg | ttt | ctg | tac | aac | tta | acc | ttg | cag | aga | gcc | act | ggc | atc | agc | ttt | 48 |
| Met | Phe | Leu | Tyr | Asn | Leu | Thr | Leu | Gln | Arg | Ala | Thr | Gly | Ile | Ser | Phe | |
| 1 | | | | 5 | | | | | 10 | | | | | 15 | | |
| gcc | att | cat | gga | aac | ttt | tct | gga | acc | aaa | caa | caa | gaa | att | gtt | gtt | 96 |
| Ala | Ile | His | Gly | Asn | Phe | Ser | Gly | Thr | Lys | Gln | Gln | Glu | Ile | Val | Val | |
| | | | 20 | | | | | 25 | | | | | 30 | | | |
| tcc | cgt | ggg | aag | atc | ttg | gag | ctg | ctt | cgc | cca | gac | ccc | aac | act | ggc | 144 |
| Ser | Arg | Gly | Lys | Ile | Leu | Glu | Leu | Leu | Arg | Pro | Asp | Pro | Asn | Thr | Gly | |
| | | 35 | | | | | 40 | | | | | 45 | | | | |
| aaa | gta | cat | acc | cta | ctc | act | gtg | gaa | gta | ttc | ggt | gtt | atc | cgg | tca | 192 |
| Lys | Val | His | Thr | Leu | Leu | Thr | Val | Glu | Val | Phe | Gly | Val | Ile | Arg | Ser | |
| | 50 | | | | | 55 | | | | | 60 | | | | | |
| ctc | atg | gcc | ttt | agg | ctg | aca | ggt | ggc | acc | aaa | gac | tac | att | gta | gtt | 240 |
| Leu | Met | Ala | Phe | Arg | Leu | Thr | Gly | Gly | Thr | Lys | Asp | Tyr | Ile | Val | Val | |
| 65 | | | | | 70 | | | | | 75 | | | | | 80 | |
| ggc | agt | gac | tct | ggt | cga | att | gtt | att | ttg | gaa | tac | cag | cca | tct | aag | 288 |
| Gly | Ser | Asp | Ser | Gly | Arg | Ile | Val | Ile | Leu | Glu | Tyr | Gln | Pro | Ser | Lys | |
| | | | | 85 | | | | | 90 | | | | | 95 | | |
| aat | atg | ttt | gag | aag | att | cac | caa | gaa | acc | ttt | ggc | aag | agt | gga | tgc | 336 |
| Asn | Met | Phe | Glu | Lys | Ile | His | Gln | Glu | Thr | Phe | Gly | Lys | Ser | Gly | Cys | |
| | | | 100 | | | | | 105 | | | | | 110 | | | |
| cgt | cgc | atc | gtt | cct | ggc | cag | ttc | tta | gct | gtg | gat | ccc | aaa | ggg | cga | 384 |
| Arg | Arg | Ile | Val | Pro | Gly | Gln | Phe | Leu | Ala | Val | Asp | Pro | Lys | Gly | Arg | |
| | | 115 | | | | | 120 | | | | | 125 | | | | |
| gcc | gtt | atg | att | agt | gcc | att | gag | aaa | cag | aaa | ttg | gtg | tat | att | ttg | 432 |
| Ala | Val | Met | Ile | Ser | Ala | Ile | Glu | Lys | Gln | Lys | Leu | Val | Tyr | Ile | Leu | |
| | 130 | | | | | 135 | | | | | 140 | | | | | |
| aac | aga | gat | gct | gca | gcc | cga | ctt | acc | att | tca | tct | ccc | ctg | gaa | gcc | 480 |
| Asn | Arg | Asp | Ala | Ala | Ala | Arg | Leu | Thr | Ile | Ser | Ser | Pro | Leu | Glu | Ala | |
| 145 | | | | | 150 | | | | | 155 | | | | | 160 | |
| cac | aaa | gca | aac | act | tta | gtg | tat | cat | gta | gtt | gga | gta | gat | gtc | gga | 528 |
| His | Lys | Ala | Asn | Thr | Leu | Val | Tyr | His | Val | Val | Gly | Val | Asp | Val | Gly | |
| | | | | 165 | | | | | 170 | | | | | 175 | | |
| ttt | gaa | aat | cca | atg | ttt | gct | tgt | ctg | gaa | atg | gat | tat | gag | gaa | gca | 576 |
| Phe | Glu | Asn | Pro | Met | Phe | Ala | Cys | Leu | Glu | Met | Asp | Tyr | Glu | Glu | Ala | |
| | | | 180 | | | | | 185 | | | | | 190 | | | |
| gac | aat | gat | cca | aca | ggg | gaa | gca | gca | gct | aat | acc | cag | cag | aca | ctt | 624 |
| Asp | Asn | Asp | Pro | Thr | Gly | Glu | Ala | Ala | Ala | Asn | Thr | Gln | Gln | Thr | Leu | |
| | | 195 | | | | | 200 | | | | | 205 | | | | |
| act | ttc | tat | gag | cta | gac | ctt | ggt | tta | aat | cat | gtg | gtc | cga | aaa | tac | 672 |
| Thr | Phe | Tyr | Glu | Leu | Asp | Leu | Gly | Leu | Asn | His | Val | Val | Arg | Lys | Tyr | |
| | 210 | | | | | 215 | | | | | 220 | | | | | |
| agt | gaa | cct | ttg | gag | gaa | cac | ggc | aac | ttc | ctt | att | aca | gtt | cca | gga | 720 |
| Ser | Glu | Pro | Leu | Glu | Glu | His | Gly | Asn | Phe | Leu | Ile | Thr | Val | Pro | Gly | |
| 225 | | | | | 230 | | | | | 235 | | | | | 240 | |
| ggg | tca | gat | ggt | cca | agt | gga | gta | ctg | atc | tgc | tct | gaa | aac | tat | att | 768 |
| Gly | Ser | Asp | Gly | Pro | Ser | Gly | Val | Leu | Ile | Cys | Ser | Glu | Asn | Tyr | Ile | |
| | | | | 245 | | | | | 250 | | | | | 255 | | |
| act | tac | aag | aac | ttt | ggt | gac | cag | cca | gat | atc | cgc | tgt | cca | att | ccc | 816 |
| Thr | Tyr | Lys | Asn | Phe | Gly | Asp | Gln | Pro | Asp | Ile | Arg | Cys | Pro | Ile | Pro | |
| | | | 260 | | | | | 265 | | | | | 270 | | | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| agg | agg | cgg | aat | gac | ctg | gat | gac | cct | gaa | aga | gga | atg | att | ttt | gtc | 864  |
| Arg | Arg | Arg | Asn | Asp | Leu | Asp | Asp | Pro | Glu | Arg | Gly | Met | Ile | Phe | Val |      |
|     |     | 275 |     |     |     | 280 |     |     |     |     | 285 |     |     |     |     |      |
| tgc | tct | gca | acc | cat | aaa | acc | aaa | tcg | atg | ttc | ttc | ttt | ttg | gct | caa | 912  |
| Cys | Ser | Ala | Thr | His | Lys | Thr | Lys | Ser | Met | Phe | Phe | Phe | Leu | Ala | Gln |      |
|     | 290 |     |     |     |     | 295 |     |     |     |     | 300 |     |     |     |     |      |
| act | gag | cag | gga | gat | atc | ttt | aag | atc | act | ttg | gag | aca | gat | gaa | gat | 960  |
| Thr | Glu | Gln | Gly | Asp | Ile | Phe | Lys | Ile | Thr | Leu | Glu | Thr | Asp | Glu | Asp |      |
| 305 |     |     |     |     | 310 |     |     |     |     | 315 |     |     |     |     | 320 |      |
| atg | gtt | act | gag | atc | cgg | ctc | aaa | tat | ttt | gat | act | gta | ccc | gtt | gct | 1008 |
| Met | Val | Thr | Glu | Ile | Arg | Leu | Lys | Tyr | Phe | Asp | Thr | Val | Pro | Val | Ala |      |
|     |     |     |     | 325 |     |     |     |     | 330 |     |     |     |     | 335 |     |      |
| gct | gcc | atg | tgt | gtg | ctt | aaa | aca | ggg | ttc | ctt | ttt | gta | gca | tca | gaa | 1056 |
| Ala | Ala | Met | Cys | Val | Leu | Lys | Thr | Gly | Phe | Leu | Phe | Val | Ala | Ser | Glu |      |
|     |     |     | 340 |     |     |     |     | 345 |     |     |     |     | 350 |     |     |      |
| ttt | gga | aac | cat | tac | tta | tat | caa | att | gca | cat | ctt | gga | gat | gat | gat | 1104 |
| Phe | Gly | Asn | His | Tyr | Leu | Tyr | Gln | Ile | Ala | His | Leu | Gly | Asp | Asp | Asp |      |
|     |     | 355 |     |     |     |     | 360 |     |     |     |     | 365 |     |     |     |      |
| gaa | gaa | cct | gag | ttt | tca | tca | gcc | atg | cct | ctg | gaa | gaa | gga | gac | aca | 1152 |
| Glu | Glu | Pro | Glu | Phe | Ser | Ser | Ala | Met | Pro | Leu | Glu | Glu | Gly | Asp | Thr |      |
| 370 |     |     |     |     | 375 |     |     |     |     | 380 |     |     |     |     |     |      |
| ttc | ttt | ttt | cag | cca | aga | cca | ctt | aaa | aac | ctt | gtg | ctg | gtt | gat | gag | 1200 |
| Phe | Phe | Phe | Gln | Pro | Arg | Pro | Leu | Lys | Asn | Leu | Val | Leu | Val | Asp | Glu |      |
| 385 |     |     |     |     | 390 |     |     |     |     | 395 |     |     |     |     | 400 |      |
| ttg | gac | agc | ctc | tct | ccc | att | ctg | ttt | tgc | cag | ata | gct | gat | ctg | gcc | 1248 |
| Leu | Asp | Ser | Leu | Ser | Pro | Ile | Leu | Phe | Cys | Gln | Ile | Ala | Asp | Leu | Ala |      |
|     |     |     |     | 405 |     |     |     |     | 410 |     |     |     |     | 415 |     |      |
| aat | gaa | gat | act | cca | cag | ttg | tat | gtg | gcc | tgt | ggt | agg | gga | ccc | cga | 1296 |
| Asn | Glu | Asp | Thr | Pro | Gln | Leu | Tyr | Val | Ala | Cys | Gly | Arg | Gly | Pro | Arg |      |
|     |     |     | 420 |     |     |     |     | 425 |     |     |     |     | 430 |     |     |      |
| tca | tct | ctg | aga | gtc | cta | aga | cat | gga | ctt | gag | gtg | tca | gaa | atg | gct | 1344 |
| Ser | Ser | Leu | Arg | Val | Leu | Arg | His | Gly | Leu | Glu | Val | Ser | Glu | Met | Ala |      |
|     |     |     | 435 |     |     |     |     | 440 |     |     |     |     | 445 |     |     |      |
| gtt | tct | gag | cta | cct | ggt | aac | ccc | aac | gct | gtc | tgg | aca | gtg | cgt | cga | 1392 |
| Val | Ser | Glu | Leu | Pro | Gly | Asn | Pro | Asn | Ala | Val | Trp | Thr | Val | Arg | Arg |      |
|     | 450 |     |     |     |     | 455 |     |     |     |     | 460 |     |     |     |     |      |
| cac | att | gaa | gat | gag | ttt | gat | gcc | tac | atc | att | gtg | tct | ttc | gtg | aat | 1440 |
| His | Ile | Glu | Asp | Glu | Phe | Asp | Ala | Tyr | Ile | Ile | Val | Ser | Phe | Val | Asn |      |
| 465 |     |     |     |     | 470 |     |     |     |     | 475 |     |     |     |     | 480 |      |
| gcc | acc | cta | gtg | ttg | tcc | att | gga | gaa | act | gta | gaa | gaa | gtg | act | gac | 1488 |
| Ala | Thr | Leu | Val | Leu | Ser | Ile | Gly | Glu | Thr | Val | Glu | Glu | Val | Thr | Asp |      |
|     |     |     |     | 485 |     |     |     |     | 490 |     |     |     |     | 495 |     |      |
| tct | ggg | ttc | ctg | ggg | acc | acc | ccg | acc | ttg | tcc | tgc | tcc | tta | tta | gga | 1536 |
| Ser | Gly | Phe | Leu | Gly | Thr | Thr | Pro | Thr | Leu | Ser | Cys | Ser | Leu | Leu | Gly |      |
|     |     |     | 500 |     |     |     |     | 505 |     |     |     |     | 510 |     |     |      |
| gat | gat | gcc | ttg | gtg | cag | gtc | tat | cca | gat | ggc | att | cgg | cac | ata | cga | 1584 |
| Asp | Asp | Ala | Leu | Val | Gln | Val | Tyr | Pro | Asp | Gly | Ile | Arg | His | Ile | Arg |      |
|     |     | 515 |     |     |     |     | 520 |     |     |     |     | 525 |     |     |     |      |
| gca | gac | aag | aga | gtc | aat | gag | tgg | aag | acc | cct | gga | aag | aaa | aca | att | 1632 |
| Ala | Asp | Lys | Arg | Val | Asn | Glu | Trp | Lys | Thr | Pro | Gly | Lys | Lys | Thr | Ile |      |
|     | 530 |     |     |     |     | 535 |     |     |     |     | 540 |     |     |     |     |      |
| gtg | aag | tgt | gca | gtg | aac | cag | cga | caa | gtg | gtg | att | gcc | ctg | aca | gga | 1680 |
| Val | Lys | Cys | Ala | Val | Asn | Gln | Arg | Gln | Val | Val | Ile | Ala | Leu | Thr | Gly |      |
| 545 |     |     |     |     | 550 |     |     |     |     | 555 |     |     |     |     | 560 |      |
| gga | gag | ctg | gtc | tat | ttc | gag | atg | gat | cct | tca | gga | cag | ctg | aat | gag | 1728 |
| Gly | Glu | Leu | Val | Tyr | Phe | Glu | Met | Asp | Pro | Ser | Gly | Gln | Leu | Asn | Glu |      |
|     |     |     |     | 565 |     |     |     |     | 570 |     |     |     |     | 575 |     |      |
| tac | aca | gaa | cgg | aag | gag | atg | tca | gca | gat | gtg | gtg | tgc | atg | agt | ctg | 1776 |
| Tyr | Thr | Glu | Arg | Lys | Glu | Met | Ser | Ala | Asp | Val | Val | Cys | Met | Ser | Leu |      |
|     |     |     | 580 |     |     |     |     | 585 |     |     |     |     | 590 |     |     |      |

```
gcc aat gta ccc cct gga gag cag cgg tct cgc ttc ctg gct gtg ggg    1824
Ala Asn Val Pro Pro Gly Glu Gln Arg Ser Arg Phe Leu Ala Val Gly
        595                 600                 605 ctt gtg gac aac act gtc aga atc atc tcc ctg gat ccc tca gac tgt    1872
Leu Val Asp Asn Thr Val Arg Ile Ile Ser Leu Asp Pro Ser Asp Cys
610                 615                 620 ttg caa cct cta agc atg cag gct ctc cca gcc cag cct gag tcc ttg    1920
Leu Gln Pro Leu Ser Met Gln Ala Leu Pro Ala Gln Pro Glu Ser Leu
625                 630                 635                 640 tgt atc gtg gaa atg ggt ggg act gag aag cag gat gag ctg ggt gag    1968
Cys Ile Val Glu Met Gly Gly Thr Glu Lys Gln Asp Glu Leu Gly Glu
                645                 650                 655 agg ggc tcg att ggc ttc cta tac ctg aat att ggg cta cag aac ggt    2016
Arg Gly Ser Ile Gly Phe Leu Tyr Leu Asn Ile Gly Leu Gln Asn Gly
        660                 665                 670 gtg ctg ctg agg act gtc ttg gac cct gtc act ggg gat ttg tct gat    2064
Val Leu Leu Arg Thr Val Leu Asp Pro Val Thr Gly Asp Leu Ser Asp
675                 680                 685 act cgc act cgg tac ctg ggg tcc cgt cct gtg aag ctc ttc cga gtc    2112
Thr Arg Thr Arg Tyr Leu Gly Ser Arg Pro Val Lys Leu Phe Arg Val
690                 695                 700 cga atg caa ggc cag gag gca gta ttg gcc atg tca agc cgc tca tgg    2160
Arg Met Gln Gly Gln Glu Ala Val Leu Ala Met Ser Ser Arg Ser Trp
705                 710                 715                 720 ttg agc tat tct tac caa tct cgc ttc cat ctc acc cca ctg tct tac    2208
Leu Ser Tyr Ser Tyr Gln Ser Arg Phe His Leu Thr Pro Leu Ser Tyr
                725                 730                 735 gag aca ctg gaa ttt gca tcg ggt ttt gcc tcg gaa cag tgt ccc gag    2256
Glu Thr Leu Glu Phe Ala Ser Gly Phe Ala Ser Glu Gln Cys Pro Glu
        740                 745                 750 ggc att gtg gcc atc tcc acc aac acc cta cgg att ttg gca tta gag    2304
Gly Ile Val Ala Ile Ser Thr Asn Thr Leu Arg Ile Leu Ala Leu Glu
755                 760                 765 aag ctc ggt gct gtc ttc aat caa gta gcc ttc cca ctg cag tac aca    2352
Lys Leu Gly Ala Val Phe Asn Gln Val Ala Phe Pro Leu Gln Tyr Thr
770                 775                 780 ccc agg aaa ttt gtc atc cac cct gag agt aac aac ctt att atc att    2400
Pro Arg Lys Phe Val Ile His Pro Glu Ser Asn Asn Leu Ile Ile Ile
785                 790                 795                 800 gaa acg gac cac aat gcc tac act gag gcc acg aaa gct cag aga aag    2448
Glu Thr Asp His Asn Ala Tyr Thr Glu Ala Thr Lys Ala Gln Arg Lys
                805                 810                 815 cag cag atg gca gag gaa atg gtg gaa gca gca ggg gag gat gag cgg    2496
Gln Gln Met Ala Glu Glu Met Val Glu Ala Ala Gly Glu Asp Glu Arg
        820                 825                 830 gag ctg gcc gca gag atg gca gca gca ttc ctc aat gaa aac ctc cct    2544
Glu Leu Ala Ala Glu Met Ala Ala Ala Phe Leu Asn Glu Asn Leu Pro
835                 840                 845 gaa tcc atc ttt gga gct ccc aag gct ggc aat ggg cag tgg gcc tct    2592
Glu Ser Ile Phe Gly Ala Pro Lys Ala Gly Asn Gly Gln Trp Ala Ser
850                 855                 860 gtg atc cga gtg atg aat ccc att caa ggg aac aca ctg gac ctt gtc    2640
Val Ile Arg Val Met Asn Pro Ile Gln Gly Asn Thr Leu Asp Leu Val
865                 870                 875                 880 cag ctg gaa cag aat gag gca gct ttt agt gtg gct gtg tgc agg ttt    2688
Gln Leu Glu Gln Asn Glu Ala Ala Phe Ser Val Ala Val Cys Arg Phe
                885                 890                 895 tcc aac act ggt gaa gac tgg tat gtg ctg gtg ggt gtg gcc aag gac    2736
Ser Asn Thr Gly Glu Asp Trp Tyr Val Leu Val Gly Val Ala Lys Asp
        900                 905                 910
```

```
ctg ata cta aac ccc cga tct gtg gca ggg ggc ttc gtc tat act tac    2784
Leu Ile Leu Asn Pro Arg Ser Val Ala Gly Gly Phe Val Tyr Thr Tyr
        915                 920                 925 aag ctt gtg aac aat ggg gaa aaa ctg gag ttt ttg cac aag act cct    2832
Lys Leu Val Asn Asn Gly Glu Lys Leu Glu Phe Leu His Lys Thr Pro
930                 935                 940 gtg gaa gag gtc cct gct gct att gcc cca ttc cag ggg agg gtg ttg    2880
Val Glu Glu Val Pro Ala Ala Ile Ala Pro Phe Gln Gly Arg Val Leu
945                 950                 955                 960 att ggt gtg ggg aag ctg ttg cgt gtc tat gac ctg gga aag aag aag    2928
Ile Gly Val Gly Lys Leu Leu Arg Val Tyr Asp Leu Gly Lys Lys Lys
                965                 970                 975 tta ctc cga aaa tgt gag aat aag cat att gcc aat tat atc tct ggg    2976
Leu Leu Arg Lys Cys Glu Asn Lys His Ile Ala Asn Tyr Ile Ser Gly
            980                 985                 990 atc cag act atc gga cat agg gta att gta tct gat gtc caa gaa agt    3024
Ile Gln Thr Ile Gly His Arg Val Ile Val Ser Asp Val Gln Glu Ser
        995                 1000                1005 ttc atc tgg gtt cgc tac aag cgt aat gaa aac cag ctt atc atc       3069
Phe Ile Trp Val Arg Tyr Lys Arg Asn Glu Asn Gln Leu Ile Ile
    1010                1015                1020 ttt gct gat gat acc tac ccc cga tgg gtc act aca gcc agc ctc       3114
Phe Ala Asp Asp Thr Tyr Pro Arg Trp Val Thr Thr Ala Ser Leu
    1025                1030                1035 ctg gac tat gac act gtg gct ggg gca gac aag ttt ggc aac ata       3159
Leu Asp Tyr Asp Thr Val Ala Gly Ala Asp Lys Phe Gly Asn Ile
    1040                1045                1050 tgt gtg gtg agg ctc cca cct aac acc aat gat gaa gta gat gag       3204
Cys Val Val Arg Leu Pro Pro Asn Thr Asn Asp Glu Val Asp Glu
    1055                1060                1065 gat cct aca gga aac aaa gcc ctg tgg gac cgt ggc ttg ctc aat       3249
Asp Pro Thr Gly Asn Lys Ala Leu Trp Asp Arg Gly Leu Leu Asn
    1070                1075                1080 ggg gcc tcc cag aag gca gag gtg atc atg aac tac cat gtc ggg       3294
Gly Ala Ser Gln Lys Ala Glu Val Ile Met Asn Tyr His Val Gly
    1085                1090                1095 gag acg gtg ctg tcc ttg cag aag acc acg ctg atc cct gga ggc       3339
Glu Thr Val Leu Ser Leu Gln Lys Thr Thr Leu Ile Pro Gly Gly
    1100                1105                1110 tca gaa tca ctt gtc tat acc acc ttg tct gga gga att ggc atc       3384
Ser Glu Ser Leu Val Tyr Thr Thr Leu Ser Gly Gly Ile Gly Ile
    1115                1120                1125 ctt gtg cca ttc acg tcc cat gag gac cat gac ttc ttc cag cat       3429
Leu Val Pro Phe Thr Ser His Glu Asp His Asp Phe Phe Gln His
    1130                1135                1140 gtg gaa atg cac ctg cgg tct gaa cat ccc cct ctc tgt ggg cgg       3474
Val Glu Met His Leu Arg Ser Glu His Pro Pro Leu Cys Gly Arg
    1145                1150                1155 gac cac ctc agc ttt cgc tcc tac tac ttc cct gtg aag aat gtg       3519
Asp His Leu Ser Phe Arg Ser Tyr Tyr Phe Pro Val Lys Asn Val
    1160                1165                1170 att gat gga gac ctc tgt gag cag ttc aat tcc atg gaa ccc aac       3564
Ile Asp Gly Asp Leu Cys Glu Gln Phe Asn Ser Met Glu Pro Asn
    1175                1180                1185 aaa caa aag aac gtc tct gaa gaa ctg gac cga acc cca ccc gaa       3609
Lys Gln Lys Asn Val Ser Glu Glu Leu Asp Arg Thr Pro Pro Glu
    1190                1195                1200 gtg tcc aag aaa ctc gag gat atc cgg acc cgc tac gcc ttc           3651
Val Ser Lys Lys Leu Glu Asp Ile Arg Thr Arg Tyr Ala Phe
    1205                1210                1215
```

-continued

```
<210> SEQ ID NO 4
<211> LENGTH: 1217
<212> TYPE: PRT
<213> ORGANISM: Homo sapiens

<400> SEQUENCE: 4

Met Phe Leu Tyr Asn Leu Thr Leu Gln Arg Ala Thr Gly Ile Ser Phe
1               5                   10                  15

Ala Ile His Gly Asn Phe Ser Gly Thr Lys Gln Gln Glu Ile Val Val
            20                  25                  30

Ser Arg Gly Lys Ile Leu Glu Leu Leu Arg Pro Asp Pro Asn Thr Gly
        35                  40                  45

Lys Val His Thr Leu Leu Thr Val Glu Val Phe Gly Val Ile Arg Ser
    50                  55                  60

Leu Met Ala Phe Arg Leu Thr Gly Gly Thr Lys Asp Tyr Ile Val Val
65                  70                  75                  80

Gly Ser Asp Ser Gly Arg Ile Val Ile Leu Glu Tyr Gln Pro Ser Lys
                85                  90                  95

Asn Met Phe Glu Lys Ile His Gln Glu Thr Phe Gly Lys Ser Gly Cys
            100                 105                 110

Arg Arg Ile Val Pro Gly Gln Phe Leu Ala Val Asp Pro Lys Gly Arg
        115                 120                 125

Ala Val Met Ile Ser Ala Ile Glu Lys Gln Lys Leu Val Tyr Ile Leu
    130                 135                 140

Asn Arg Asp Ala Ala Arg Leu Thr Ile Ser Ser Pro Leu Glu Ala
145                 150                 155                 160

His Lys Ala Asn Thr Leu Val Tyr His Val Val Gly Val Asp Val Gly
                165                 170                 175

Phe Glu Asn Pro Met Phe Ala Cys Leu Glu Met Asp Tyr Glu Glu Ala
            180                 185                 190

Asp Asn Asp Pro Thr Gly Glu Ala Ala Asn Thr Gln Gln Thr Leu
        195                 200                 205

Thr Phe Tyr Glu Leu Asp Leu Gly Leu Asn His Val Val Arg Lys Tyr
    210                 215                 220

Ser Glu Pro Leu Glu Glu His Gly Asn Phe Leu Ile Thr Val Pro Gly
225                 230                 235                 240

Gly Ser Asp Gly Pro Ser Gly Val Leu Ile Cys Ser Glu Asn Tyr Ile
                245                 250                 255

Thr Tyr Lys Asn Phe Gly Asp Gln Pro Asp Ile Arg Cys Pro Ile Pro
            260                 265                 270

Arg Arg Arg Asn Asp Leu Asp Asp Pro Glu Arg Gly Met Ile Phe Val
        275                 280                 285

Cys Ser Ala Thr His Lys Thr Lys Ser Met Phe Phe Phe Leu Ala Gln
    290                 295                 300

Thr Glu Gln Gly Asp Ile Phe Lys Ile Thr Leu Glu Thr Asp Glu Asp
305                 310                 315                 320

Met Val Thr Glu Ile Arg Leu Lys Tyr Phe Asp Thr Val Pro Val Ala
                325                 330                 335

Ala Ala Met Cys Val Leu Lys Thr Gly Phe Leu Phe Val Ala Ser Glu
            340                 345                 350

Phe Gly Asn His Tyr Leu Tyr Gln Ile Ala His Leu Gly Asp Asp Asp
        355                 360                 365

Glu Glu Pro Glu Phe Ser Ser Ala Met Pro Leu Glu Glu Gly Asp Thr
    370                 375                 380
```

```
Phe Phe Phe Gln Pro Arg Pro Leu Lys Asn Leu Val Leu Val Asp Glu
385                 390                 395                 400

Leu Asp Ser Leu Ser Pro Ile Leu Phe Cys Gln Ile Ala Asp Leu Ala
            405                 410                 415

Asn Glu Asp Thr Pro Gln Leu Tyr Val Ala Cys Gly Arg Gly Pro Arg
        420                 425                 430

Ser Ser Leu Arg Val Leu Arg His Gly Leu Glu Val Ser Glu Met Ala
    435                 440                 445

Val Ser Glu Leu Pro Gly Asn Pro Asn Ala Val Trp Thr Val Arg Arg
450                 455                 460

His Ile Glu Asp Glu Phe Asp Ala Tyr Ile Ile Val Ser Phe Val Asn
465                 470                 475                 480

Ala Thr Leu Val Leu Ser Ile Gly Glu Thr Val Glu Glu Val Thr Asp
            485                 490                 495

Ser Gly Phe Leu Gly Thr Thr Pro Thr Leu Ser Cys Ser Leu Leu Gly
        500                 505                 510

Asp Asp Ala Leu Val Gln Val Tyr Pro Asp Gly Ile Arg His Ile Arg
    515                 520                 525

Ala Asp Lys Arg Val Asn Glu Trp Lys Thr Pro Gly Lys Lys Thr Ile
530                 535                 540

Val Lys Cys Ala Val Asn Gln Arg Gln Val Val Ile Ala Leu Thr Gly
545                 550                 555                 560

Gly Glu Leu Val Tyr Phe Glu Met Asp Pro Ser Gly Gln Leu Asn Glu
            565                 570                 575

Tyr Thr Glu Arg Lys Glu Met Ser Ala Asp Val Val Cys Met Ser Leu
        580                 585                 590

Ala Asn Val Pro Pro Gly Glu Gln Arg Ser Arg Phe Leu Ala Val Gly
    595                 600                 605

Leu Val Asp Asn Thr Val Arg Ile Ile Ser Leu Asp Pro Ser Asp Cys
610                 615                 620

Leu Gln Pro Leu Ser Met Gln Ala Leu Pro Ala Gln Pro Glu Ser Leu
625                 630                 635                 640

Cys Ile Val Glu Met Gly Gly Thr Glu Lys Gln Asp Glu Leu Gly Glu
            645                 650                 655

Arg Gly Ser Ile Gly Phe Leu Tyr Leu Asn Ile Gly Leu Gln Asn Gly
        660                 665                 670

Val Leu Leu Arg Thr Val Leu Asp Pro Val Thr Gly Asp Leu Ser Asp
    675                 680                 685

Thr Arg Thr Arg Tyr Leu Gly Ser Arg Pro Val Lys Leu Phe Arg Val
690                 695                 700

Arg Met Gln Gly Gln Glu Ala Val Leu Ala Met Ser Ser Arg Ser Trp
705                 710                 715                 720

Leu Ser Tyr Ser Tyr Gln Ser Arg Phe His Leu Thr Pro Leu Ser Tyr
            725                 730                 735

Glu Thr Leu Glu Phe Ala Ser Gly Phe Ala Ser Glu Gln Cys Pro Glu
        740                 745                 750

Gly Ile Val Ala Ile Ser Thr Asn Thr Leu Arg Ile Leu Ala Leu Glu
    755                 760                 765

Lys Leu Gly Ala Val Phe Asn Gln Val Ala Phe Pro Leu Gln Tyr Thr
770                 775                 780

Pro Arg Lys Phe Val Ile His Pro Glu Ser Asn Asn Leu Ile Ile Ile
785                 790                 795                 800

Glu Thr Asp His Asn Ala Tyr Thr Glu Ala Thr Lys Ala Gln Arg Lys
            805                 810                 815
```

-continued

```
Gln Gln Met Ala Glu Glu Met Val Glu Ala Ala Gly Glu Asp Glu Arg
        820                 825                 830

Glu Leu Ala Ala Glu Met Ala Ala Ala Phe Leu Asn Glu Asn Leu Pro
        835                 840                 845

Glu Ser Ile Phe Gly Ala Pro Lys Ala Gly Asn Gly Gln Trp Ala Ser
    850                 855                 860

Val Ile Arg Val Met Asn Pro Ile Gln Gly Asn Thr Leu Asp Leu Val
865                 870                 875                 880

Gln Leu Glu Gln Asn Glu Ala Ala Phe Ser Val Ala Val Cys Arg Phe
            885                 890                 895

Ser Asn Thr Gly Glu Asp Trp Tyr Val Leu Val Gly Val Ala Lys Asp
        900                 905                 910

Leu Ile Leu Asn Pro Arg Ser Val Ala Gly Gly Phe Val Tyr Thr Tyr
        915                 920                 925

Lys Leu Val Asn Asn Gly Glu Lys Leu Glu Phe Leu His Lys Thr Pro
        930                 935                 940

Val Glu Glu Val Pro Ala Ala Ile Ala Pro Phe Gln Gly Arg Val Leu
945                 950                 955                 960

Ile Gly Val Gly Lys Leu Leu Arg Val Tyr Asp Leu Gly Lys Lys Lys
                965                 970                 975

Leu Leu Arg Lys Cys Glu Asn Lys His Ile Ala Asn Tyr Ile Ser Gly
            980                 985                 990

Ile Gln Thr Ile Gly His Arg Val Ile Val Ser Asp Val Gln Glu Ser
            995                 1000                1005

Phe Ile Trp Val Arg Tyr Lys Arg Asn Glu Asn Gln Leu Ile Ile
    1010                1015                1020

Phe Ala Asp Asp Thr Tyr Pro Arg Trp Val Thr Thr Ala Ser Leu
    1025                1030                1035

Leu Asp Tyr Asp Thr Val Ala Gly Ala Asp Lys Phe Gly Asn Ile
    1040                1045                1050

Cys Val Val Arg Leu Pro Pro Asn Thr Asn Asp Glu Val Asp Glu
    1055                1060                1065

Asp Pro Thr Gly Asn Lys Ala Leu Trp Asp Arg Gly Leu Leu Asn
    1070                1075                1080

Gly Ala Ser Gln Lys Ala Glu Val Ile Met Asn Tyr His Val Gly
    1085                1090                1095

Glu Thr Val Leu Ser Leu Gln Lys Thr Thr Leu Ile Pro Gly Gly
    1100                1105                1110

Ser Glu Ser Leu Val Tyr Thr Thr Leu Ser Gly Gly Ile Gly Ile
    1115                1120                1125

Leu Val Pro Phe Thr Ser His Glu Asp His Asp Phe Phe Gln His
    1130                1135                1140

Val Glu Met His Leu Arg Ser Glu His Pro Pro Leu Cys Gly Arg
    1145                1150                1155

Asp His Leu Ser Phe Arg Ser Tyr Tyr Phe Pro Val Lys Asn Val
    1160                1165                1170

Ile Asp Gly Asp Leu Cys Glu Gln Phe Asn Ser Met Glu Pro Asn
    1175                1180                1185

Lys Gln Lys Asn Val Ser Glu Glu Leu Asp Arg Thr Pro Pro Glu
    1190                1195                1200

Val Ser Lys Lys Leu Glu Asp Ile Arg Thr Arg Tyr Ala Phe
    1205                1210                1215
```

```
<210> SEQ ID NO 5
<211> LENGTH: 258
<212> TYPE: DNA
<213> ORGANISM: Homo sapiens
<220> FEATURE:
<221> NAME/KEY: CDS
<222> LOCATION: (1)..(258)
<220> FEATURE:
<221> NAME/KEY: sig_peptide
<222> LOCATION: (1)..(54)
<220> FEATURE:
<221> NAME/KEY: mat_peptide
<222> LOCATION: (55)..(258)

<400> SEQUENCE: 5 atg att cca gca gtg gtc ttg ctc tta ctc ctt ttg gtt gaa caa gca        48
Met Ile Pro Ala Val Val Leu Leu Leu Leu Leu Leu Val Glu Gln Ala
        -15                 -10                 -5 gcg gcc ctg gga gag cct cag ctc tgc tat atc ctg gat gcc atc ctg        96
Ala Ala Leu Gly Glu Pro Gln Leu Cys Tyr Ile Leu Asp Ala Ile Leu
 -1   1               5                  10 ttt ctg tat gga att gtc ctc acc ctc ctc tac tgt cga ctg aag atc       144
Phe Leu Tyr Gly Ile Val Leu Thr Leu Leu Tyr Cys Arg Leu Lys Ile
 15               20                  25                  30 caa gtg cga aag gca gct ata acc agc tat gag aaa tca gat ggt gtt       192
Gln Val Arg Lys Ala Ala Ile Thr Ser Tyr Glu Lys Ser Asp Gly Val
             35                  40                  45 tac acg ggc ctg agc acc agg aac cag gag act tac gag act ctg aag       240
Tyr Thr Gly Leu Ser Thr Arg Asn Gln Glu Thr Tyr Glu Thr Leu Lys
         50                  55                  60 cat gag aaa cca cca cag                                               258
His Glu Lys Pro Pro Gln
         65

<210> SEQ ID NO 6
<211> LENGTH: 86
<212> TYPE: PRT
<213> ORGANISM: Homo sapiens

<400> SEQUENCE: 6

Met Ile Pro Ala Val Val Leu Leu Leu Leu Leu Leu Val Glu Gln Ala
        -15                 -10                 -5

Ala Ala Leu Gly Glu Pro Gln Leu Cys Tyr Ile Leu Asp Ala Ile Leu
 -1   1               5                  10

Phe Leu Tyr Gly Ile Val Leu Thr Leu Leu Tyr Cys Arg Leu Lys Ile
 15               20                  25                  30

Gln Val Arg Lys Ala Ala Ile Thr Ser Tyr Glu Lys Ser Asp Gly Val
             35                  40                  45

Tyr Thr Gly Leu Ser Thr Arg Asn Gln Glu Thr Tyr Glu Thr Leu Lys
         50                  55                  60

His Glu Lys Pro Pro Gln
         65

<210> SEQ ID NO 7
<211> LENGTH: 5
<212> TYPE: PRT
<213> ORGANISM: Homo sapiens
<220> FEATURE:
<221> NAME/KEY: BINDING
<222> LOCATION: (1)..(5)

<400> SEQUENCE: 7

Val Glu Gly Gln Trp
 1               5
```

```
<210> SEQ ID NO 8
<211> LENGTH: 25
<212> TYPE: DNA
<213> ORGANISM: Artificial
<220> FEATURE:
<223> OTHER INFORMATION: Primer

<400> SEQUENCE: 8
tggaatcctg tggcatccat gaaac                                          25

<210> SEQ ID NO 9
<211> LENGTH: 25
<212> TYPE: DNA
<213> ORGANISM: Artificial
<220> FEATURE:
<223> OTHER INFORMATION: Primer

<400> SEQUENCE: 9
taaaacgcag ctcagtaaca gtccg                                          25

<210> SEQ ID NO 10
<211> LENGTH: 22
<212> TYPE: DNA
<213> ORGANISM: Artificial
<220> FEATURE:
<223> OTHER INFORMATION: Primer

<400> SEQUENCE: 10
ttccatccag ttgccttctt gg                                             22

<210> SEQ ID NO 11
<211> LENGTH: 19
<212> TYPE: DNA
<213> ORGANISM: Artificial
<220> FEATURE:
<223> OTHER INFORMATION: Primer

<400> SEQUENCE: 11
cttcatgtac tccaggtag                                                 19

<210> SEQ ID NO 12
<211> LENGTH: 21
<212> TYPE: DNA
<213> ORGANISM: Artificial
<220> FEATURE:
<223> OTHER INFORMATION: Primer

<400> SEQUENCE: 12
cagcttaaag ggcgggtcag a                                              21

<210> SEQ ID NO 13
<211> LENGTH: 21
<212> TYPE: DNA
<213> ORGANISM: Artificial
<220> FEATURE:
<223> OTHER INFORMATION: Primer

<400> SEQUENCE: 13
tggagacgcc agctctggct c                                              21

<210> SEQ ID NO 14
<211> LENGTH: 20
<212> TYPE: DNA
<213> ORGANISM: Artificial
<220> FEATURE:
<223> OTHER INFORMATION: Primer
```

<400> SEQUENCE: 14
gctccagcag ggaacaatag                                                      20

<210> SEQ ID NO 15
<211> LENGTH: 20
<212> TYPE: DNA
<213> ORGANISM: Artificial
<220> FEATURE:
<223> OTHER INFORMATION: Primer

<400> SEQUENCE: 15 gcccttttgat ggaattcaga                                                     20

<210> SEQ ID NO 16
<211> LENGTH: 20
<212> TYPE: DNA
<213> ORGANISM: Artificial
<220> FEATURE:
<223> OTHER INFORMATION: Primer

<400> SEQUENCE: 16
ccttcccttc cctctacacc                                                      20

<210> SEQ ID NO 17
<211> LENGTH: 20
<212> TYPE: DNA
<213> ORGANISM: Artificial
<220> FEATURE:
<223> OTHER INFORMATION: Primer

<400> SEQUENCE: 17
aaggtaaggc agggtggtct                                                      20

<210> SEQ ID NO 18
<211> LENGTH: 23
<212> TYPE: PRT
<213> ORGANISM: Mus musculus

<400> SEQUENCE: 18

Leu Ser Trp Thr Ile Ala Gly Ala Ser Ile Leu Phe Leu Ser Gly Cys
1               5                   10                  15

Phe Ile Thr Arg Cys Val Val
            20

<210> SEQ ID NO 19
<211> LENGTH: 23
<212> TYPE: PRT
<213> ORGANISM: Rattus norvegicus

<400> SEQUENCE: 19

Leu Ser Trp Thr Met Ala Gly Ala Ser Ile Leu Phe Leu Ser Val Cys
1               5                   10                  15

Phe Ile Thr Arg Cys Val Val
            20

<210> SEQ ID NO 20
<211> LENGTH: 23
<212> TYPE: PRT
<213> ORGANISM: Homo sapiens

```
<400> SEQUENCE: 20

Phe Leu Trp Thr Val Ala Gly Ile Pro Ile Leu Phe Leu Ser Ala Cys
1               5                   10                  15

Phe Ile Thr Arg Cys Val Val
            20

<210> SEQ ID NO 21
<211> LENGTH: 6
<212> TYPE: PRT
<213> ORGANISM: Mus musculus

<400> SEQUENCE: 21

Arg Val Asn Glu Trp Lys
1               5

<210> SEQ ID NO 22
<211> LENGTH: 8
<212> TYPE: PRT
<213> ORGANISM: Mus musculus

<400> SEQUENCE: 22

Ile His Gln Glu Thr Phe Gly Lys
1               5

<210> SEQ ID NO 23
<211> LENGTH: 10
<212> TYPE: PRT
<213> ORGANISM: Mus musculus

<400> SEQUENCE: 23

Gln Gln Glu Ile Val Val Ser Arg Gly Lys
1               5                   10

<210> SEQ ID NO 24
<211> LENGTH: 13
<212> TYPE: PRT
<213> ORGANISM: Mus musculus

<400> SEQUENCE: 24

Ile Leu Glu Leu Leu Arg Pro Asp Pro Asn Thr Gly Lys
1               5                   10

<210> SEQ ID NO 25
<211> LENGTH: 15
<212> TYPE: PRT
<213> ORGANISM: Mus musculus

<400> SEQUENCE: 25

Asn Val Ser Glu Glu Leu Asp Arg Thr Pro Pro Glu Val Ser Lys
1               5                   10                  15

<210> SEQ ID NO 26
<211> LENGTH: 18
<212> TYPE: PRT
<213> ORGANISM: Mus musculus

<400> SEQUENCE: 26

Asn Val Ile Asp Gly Asp Leu Cys Glu Gln Phe Asn Ser Met Glu Pro
1               5                   10                  15

Asn Lys
```

```
<210> SEQ ID NO 27
<211> LENGTH: 21
<212> TYPE: PRT
<213> ORGANISM: Mus musculus

<400> SEQUENCE: 27

Asp Tyr Ile Val Val Gly Ser Asp Ser Gly Arg Ile Val Ile Leu Glu
1               5                   10                  15

Tyr Gln Pro Ser Lys
            20

<210> SEQ ID NO 28
<211> LENGTH: 23
<212> TYPE: PRT
<213> ORGANISM: Mus musculus

<400> SEQUENCE: 28

Thr Pro Val Glu Glu Val Pro Ala Ala Ile Ala Pro Phe Gln Gly Arg
1               5                   10                  15

Val Leu Ile Gly Val Gly Lys
            20

<210> SEQ ID NO 29
<211> LENGTH: 25
<212> TYPE: PRT
<213> ORGANISM: Mus musculus

<400> SEQUENCE: 29

Phe Gly Asn Ile Cys Val Val Arg Leu Pro Pro Asn Thr Asn Asp Glu
1               5                   10                  15

Val Asp Glu Asp Pro Thr Gly Asn Lys
            20                  25

<210> SEQ ID NO 30
<211> LENGTH: 8
<212> TYPE: PRT
<213> ORGANISM: Mus musculus

<400> SEQUENCE: 30

Lys Arg Val Asn Glu Trp Lys Thr
1               5

<210> SEQ ID NO 31
<211> LENGTH: 10
<212> TYPE: PRT
<213> ORGANISM: Mus musculus

<400> SEQUENCE: 31

Lys Ile His Gln Glu Thr Phe Gly Lys Ser
1               5                   10

<210> SEQ ID NO 32
<211> LENGTH: 12
<212> TYPE: PRT
<213> ORGANISM: Mus musculus

<400> SEQUENCE: 32

Lys Gln Gln Glu Ile Val Val Ser Arg Gly Lys Ile
1               5                   10

<210> SEQ ID NO 33
<211> LENGTH: 15
<212> TYPE: PRT
<213> ORGANISM: Mus musculus
```

```
<400> SEQUENCE: 33

Lys Ile Leu Glu Leu Leu Arg Pro Asp Pro Asn Thr Gly Lys Val
1               5                   10                  15

<210> SEQ ID NO 34
<211> LENGTH: 17
<212> TYPE: PRT
<213> ORGANISM: Mus musculus

<400> SEQUENCE: 34

Lys Asn Val Ser Glu Glu Leu Asp Arg Thr Pro Pro Glu Val Ser Lys
1               5                   10                  15

Lys

<210> SEQ ID NO 35
<211> LENGTH: 20
<212> TYPE: PRT
<213> ORGANISM: Mus musculus

<400> SEQUENCE: 35

Lys Asn Val Ile Asp Gly Asp Leu Cys Glu Gln Phe Asn Ser Met Glu
1               5                   10                  15

Pro Asn Lys Gln
            20

<210> SEQ ID NO 36
<211> LENGTH: 23
<212> TYPE: PRT
<213> ORGANISM: Mus musculus

<400> SEQUENCE: 36

Lys Asp Tyr Ile Val Val Gly Ser Asp Ser Gly Arg Ile Val Ile Leu
1               5                   10                  15

Glu Tyr Gln Pro Ser Lys Asn
            20

<210> SEQ ID NO 37
<211> LENGTH: 25
<212> TYPE: PRT
<213> ORGANISM: Mus musculus

<400> SEQUENCE: 37

Lys Thr Pro Val Glu Glu Val Pro Ala Ala Ile Ala Pro Phe Gln Gly
1               5                   10                  15

Arg Val Leu Ile Gly Val Gly Lys Leu
            20                  25

<210> SEQ ID NO 38
<211> LENGTH: 27
<212> TYPE: PRT
<213> ORGANISM: Mus musculus

<400> SEQUENCE: 38

Lys Phe Gly Asn Ile Cys Val Val Arg Leu Pro Pro Asn Thr Asn Asp
1               5                   10                  15

Glu Val Asp Glu Asp Pro Thr Gly Asn Lys Ala
            20                  25

<210> SEQ ID NO 39
<211> LENGTH: 1217
<212> TYPE: PRT
<213> ORGANISM: Mus musculus
```

<400> SEQUENCE: 39

```
Met Phe Leu Tyr Asn Leu Thr Leu Gln Arg Ala Thr Gly Ile Ser Phe
1               5                   10                  15

Ala Ile His Gly Asn Phe Ser Gly Thr Lys Gln Gln Glu Ile Val Val
            20                  25                  30

Ser Arg Gly Lys Ile Leu Glu Leu Leu Arg Pro Asp Pro Asn Thr Gly
        35                  40                  45

Lys Val His Thr Leu Leu Thr Val Glu Val Phe Gly Val Ile Arg Ser
    50                  55                  60

Leu Met Ala Phe Arg Leu Thr Gly Gly Thr Lys Asp Tyr Ile Val Val
65                  70                  75                  80

Gly Ser Asp Ser Gly Arg Ile Val Ile Leu Glu Tyr Gln Pro Ser Lys
                85                  90                  95

Asn Met Phe Glu Lys Ile His Gln Glu Thr Phe Gly Lys Ser Gly Cys
            100                 105                 110

Arg Arg Ile Val Pro Gly Gln Phe Leu Ala Val Asp Pro Lys Gly Arg
        115                 120                 125

Ala Val Met Ile Ser Ala Ile Glu Lys Gln Lys Leu Val Tyr Ile Leu
    130                 135                 140

Asn Arg Asp Ala Ala Ala Arg Leu Thr Ile Ser Ser Pro Leu Glu Ala
145                 150                 155                 160

His Lys Ala Asn Thr Leu Val Tyr His Val Gly Val Asp Val Gly
                165                 170                 175

Phe Glu Asn Pro Met Phe Ala Cys Leu Glu Met Asp Tyr Glu Glu Ala
            180                 185                 190

Asp Asn Asp Pro Thr Gly Glu Ala Ala Asn Thr Gln Gln Thr Leu
        195                 200                 205

Thr Phe Tyr Glu Leu Asp Leu Gly Leu Asn His Val Val Arg Lys Tyr
    210                 215                 220

Ser Glu Pro Leu Glu Glu His Gly Asn Phe Leu Ile Thr Val Pro Gly
225                 230                 235                 240

Gly Ser Asp Gly Pro Ser Gly Val Leu Ile Cys Ser Glu Asn Tyr Ile
                245                 250                 255

Thr Tyr Lys Asn Phe Gly Asp Gln Pro Asp Ile Arg Cys Pro Ile Pro
            260                 265                 270

Arg Arg Arg Asn Asp Leu Asp Pro Glu Arg Gly Met Ile Phe Val
        275                 280                 285

Cys Ser Ala Thr His Lys Thr Lys Ser Met Phe Phe Phe Leu Ala Gln
    290                 295                 300

Thr Glu Gln Gly Asp Ile Phe Lys Ile Thr Leu Glu Thr Asp Glu Asp
305                 310                 315                 320

Met Val Thr Glu Ile Arg Leu Lys Tyr Phe Asp Thr Val Pro Val Ala
                325                 330                 335

Ala Ala Met Cys Val Leu Lys Thr Gly Phe Leu Phe Val Ala Ser Glu
            340                 345                 350

Phe Gly Asn His Tyr Leu Tyr Gln Ile Ala His Leu Gly Asp Asp Asp
        355                 360                 365

Glu Glu Pro Glu Phe Ser Ser Ala Met Pro Leu Glu Glu Gly Asp Thr
    370                 375                 380

Phe Phe Phe Gln Pro Arg Pro Leu Lys Asn Leu Val Leu Val Asp Glu
385                 390                 395                 400

Leu Asp Ser Leu Ser Pro Ile Leu Phe Cys Gln Ile Ala Asp Leu Ala
                405                 410                 415
```

```
Asn Glu Asp Thr Pro Gln Leu Tyr Val Ala Cys Gly Arg Gly Pro Arg
            420                 425                 430

Ser Ser Leu Arg Val Leu Arg His Gly Leu Glu Val Ser Glu Met Ala
        435                 440                 445

Val Ser Glu Leu Pro Gly Asn Pro Asn Ala Val Trp Thr Val Arg Arg
450                 455                 460

His Ile Glu Asp Glu Phe Asp Ala Tyr Ile Ile Val Ser Phe Val Asn
465                 470                 475                 480

Ala Thr Leu Val Leu Ser Ile Gly Glu Thr Val Glu Val Thr Asp
                485                 490                 495

Ser Gly Phe Leu Gly Thr Thr Pro Thr Leu Ser Cys Ser Leu Leu Gly
            500                 505                 510

Asp Asp Ala Leu Val Gln Val Tyr Pro Asp Gly Ile Arg His Ile Arg
                515                 520                 525

Ala Asp Lys Arg Val Asn Glu Trp Lys Thr Pro Gly Lys Lys Thr Ile
        530                 535                 540

Val Lys Cys Ala Val Asn Gln Arg Gln Val Val Ile Ala Leu Thr Gly
545                 550                 555                 560

Gly Glu Leu Val Tyr Phe Glu Met Asp Pro Ser Gly Gln Leu Asn Glu
            565                 570                 575

Tyr Thr Glu Arg Lys Glu Met Ser Ala Asp Val Val Cys Met Ser Leu
            580                 585                 590

Ala Asn Val Pro Pro Gly Glu Gln Arg Ser Arg Phe Leu Ala Val Gly
        595                 600                 605

Leu Val Asp Asn Thr Val Arg Ile Ile Ser Leu Asp Pro Ser Asp Cys
            610                 615                 620

Leu Gln Pro Leu Ser Met Gln Ala Leu Pro Ala Gln Pro Glu Ser Leu
625                 630                 635                 640

Cys Ile Val Glu Met Gly Gly Thr Glu Lys Gln Asp Glu Leu Gly Glu
                645                 650                 655

Arg Gly Ser Ile Gly Phe Leu Tyr Leu Asn Ile Gly Leu Gln Asn Gly
            660                 665                 670

Val Leu Leu Arg Thr Val Leu Asp Pro Val Thr Gly Asp Leu Ser Asp
            675                 680                 685

Thr Arg Thr Arg Tyr Leu Gly Ser Arg Pro Val Lys Leu Phe Arg Val
690                 695                 700

Arg Met Gln Gly Gln Glu Ala Val Leu Ala Met Ser Ser Arg Ser Trp
705                 710                 715                 720

Leu Ser Tyr Ser Tyr Gln Ser Arg Phe His Leu Thr Pro Leu Ser Tyr
            725                 730                 735

Glu Thr Leu Glu Phe Ala Ser Gly Phe Ala Ser Glu Gln Cys Pro Glu
            740                 745                 750

Gly Ile Val Ala Ile Ser Thr Asn Thr Leu Arg Ile Leu Ala Leu Glu
        755                 760                 765

Lys Leu Gly Ala Val Phe Asn Gln Val Ala Phe Pro Leu Gln Tyr Thr
        770                 775                 780

Pro Arg Lys Phe Val Ile His Pro Glu Ser Asn Asn Leu Ile Ile Ile
785                 790                 795                 800

Glu Thr Asp His Asn Ala Tyr Thr Glu Ala Thr Lys Ala Gln Arg Lys
                805                 810                 815

Gln Gln Met Ala Glu Glu Met Val Glu Ala Ala Gly Glu Asp Glu Arg
            820                 825                 830

Glu Leu Ala Ala Glu Met Ala Ala Ala Phe Leu Asn Glu Asn Leu Pro
            835                 840                 845
```

```
Glu Ser Ile Phe Gly Ala Pro Lys Ala Gly Asn Gly Gln Trp Ala Ser
850                 855                 860

Val Ile Arg Val Met Asn Pro Ile Gln Gly Asn Thr Leu Asp Leu Val
865                 870                 875                 880

Gln Leu Glu Gln Asn Glu Ala Ala Phe Ser Val Ala Val Cys Arg Phe
            885                 890                 895

Ser Asn Thr Gly Glu Asp Trp Tyr Val Leu Val Gly Val Ala Lys Asp
            900                 905                 910

Leu Ile Leu Ser Pro Arg Ser Val Ala Gly Gly Phe Val Tyr Thr Tyr
        915                 920                 925

Lys Leu Val Asn Asn Gly Glu Lys Leu Glu Phe Leu His Lys Thr Pro
    930                 935                 940

Val Glu Glu Val Pro Ala Ala Ile Ala Pro Phe Gln Gly Arg Val Leu
945                 950                 955                 960

Ile Gly Val Gly Lys Leu Leu Arg Val Tyr Asp Leu Gly Lys Lys Lys
            965                 970                 975

Leu Leu Arg Lys Cys Glu Asn Lys His Ile Ala Asn Tyr Ile Ser Gly
        980                 985                 990

Ile Gln Thr Ile Gly His Arg Val  Ile Val Ser Asp Val  Gln Glu Ser
            995             1000                1005

Phe Ile  Trp Val Arg Tyr  Lys  Arg Asn Glu Asn Gln  Leu Ile Ile
    1010                  1015                 1020

Phe Ala  Asp Asp Thr Tyr  Pro  Arg Trp Val Thr Thr  Ala Ser Leu
    1025                  1030                 1035

Leu Asp  Tyr Asp Thr Val  Ala  Gly Ala Asp Lys Phe  Gly Asn Ile
    1040                  1045                 1050

Cys Val  Val Arg Leu Pro  Pro  Asn Thr Asn Asp Glu  Val Asp Glu
    1055                  1060                 1065

Asp Pro  Thr Gly Asn Lys  Ala  Leu Trp Asp Arg Gly  Leu Leu Asn
    1070                  1075                 1080

Gly Ala  Ser Gln Lys Ala  Glu  Val Ile Met Asn Tyr  His Val Gly
    1085                  1090                 1095

Glu Thr  Val Leu Ser Leu  Gln  Lys Thr Thr Leu Ile  Pro Gly Gly
    1100                  1105                 1110

Ser Glu  Ser Leu Val Tyr  Thr  Thr Leu Ser Gly Gly  Ile Gly Ile
    1115                  1120                 1125

Leu Val  Pro Phe Thr Ser  His  Glu Asp His Asp Phe  Phe Gln His
    1130                  1135                 1140

Val Glu  Met His Leu Arg  Ser  Glu His Pro Pro Leu  Cys Gly Arg
    1145                  1150                 1155

Asp His  Leu Ser Phe Arg  Ser  Tyr Tyr Phe Pro Val  Lys Asn Val
    1160                  1165                 1170

Ile Asp  Gly Asp Leu Cys  Glu  Gln Phe Asn Ser Met  Glu Pro Asn
    1175                  1180                 1185

Lys Gln  Lys Asn Val Ser  Glu  Glu Leu Asp Arg Thr  Pro Pro Glu
    1190                  1195                 1200

Val Ser  Lys Lys Leu Glu  Asp  Ile Arg Thr Arg Tyr  Ala Phe
    1205                  1210                 1215
```

USE APPLICATION OF SUGAR CHAIN-RECOGNIZING RECEPTOR

CROSS-REFERENCE TO RELATED APPLICATIONS

This patent application is the U.S. national phase of International Patent Application No. PCT/JP2009/063008, filed on Jul. 17, 2009.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 52,639 bytes ASCII (Text) file named "707526_RevisedSequenceListing" created Jul. 3, 2012.

TECHNICAL FIELD

The present invention relates to a novel use of Mincle (Macrophage inducible C-type lectin), known as a sugar chain-recognizing receptor. Specifically, the present invention relates to the suppression of inflammatory reactions by inhibiting the expression or a function (interaction with a protein or Fc receptor common γ subunit (FcRγ) released from non-homeostatically dead cells) of Mincle, a screening method for a substance that regulates inflammatory reactions, particularly a substance having anti-inflammatory action, with the expression or a function of Mincle as an index, and a diagnosis of non-homeostatic cell death with a protein that interacts with Mincle, released from dead cells, as an index.

BACKGROUND ART

In contrast to physiological programmed cell death, wherein dying cells are rapidly engulfed and digested by phagocytes without inducing inflammation (Nonpatent Document 1), in the excess or non-homeostatic cell death caused by non-infectious stimuli such as irradiation and tissue damage, transient infiltration of neutrophils into tissue is induced (Nonpatent Document 2). The molecular mechanism by which cells recognize this excess or non-homeostatic cell death and respond appropriately has not fully been clarified.

The Toll-like receptor (TLR) family of innate immunity receptors was reported to recognize self-ligands released from dead cells, such as hyaluronan, heat shock proteins (HSPs), uric acid, fibronectin, cardiolipin and nucleosome, as well as DNA/RNA-protein complexes such as small nuclear ribonucleoproteins (snRNPs) (Nonpatent Document 3). Some of these TLR-self-ligand interactions have been shown to be involved in inflammatory diseases.

Although C-type lectins are receptors in a family other than the TLR family, they are capable of mediating the perception of dead cells. These receptors play a distinct role in immunity as pattern-recognizing receptors (PRRs) of pathogen sugar chains. Furthermore, recent evidence has suggested that they may also be capable of recognizing ligands such as proteins, fats, and minerals. In addition to acting as PRRs, some of the C-type lectins expressed in bone marrow cells also function as receptors of dead cells (Nonpatent Document 4). Most of them are receptors of phagocytes that promote the clearance of dead cells.

Of the C-type lectin receptors, Mincle (also known as Clec4e or Clecsf9) is a type-2 transmembrane C-type lectin receptor expressed in macrophages. Previous reports have shown that the transcription of Mincle is elevated with some stimuli and cell stress, and that the expression is regulated by the transcriptional factor NF-IL6 (C/EBPβ) (Patent Document 1, Nonpatent Document 5); however, physiological functions of Mincle and physiological ligands thereof remain unknown.

PRIOR ART DOCUMENTS

Patent Document

Patent Document 1: JP-A-2001-112482

Nonpatent Documents

Nonpatent Document 1: J Clin Invest 108, 957-62 (2001)
Nonpatent Document 2: Oncogene 20, 7085-95 (2001)
Nonpatent Document 3: Nat Rev Immunol 6, 823-35 (2006)
Nonpatent Document 4: Nat Immunol 7, 1258-65 (2006)
Nonpatent Document 5: J Immunol 163, 5039-48 (1999)

SUMMARY OF THE INVENTION

Problems to be Solved by the Invention

It is an object of the present invention to identify a novel molecule that recognizes non-programmed, excess or non-homeostatic cell death and is involved in a mechanism of induction of inflammatory responses, particularly a receptor molecule that recognizes a self-ligand released from dead cells, and to provide a novel means of regulating inflammatory reactions by regulating the signaling via the ligand-receptor interaction.

It is another object of the present invention to identify a physiological ligand of Mincle and elucidate the physiological functions thereof.

Means of Solving the Problems

The present inventors conducted extensive investigations to solve the above-described problems, and found that Mincle selectively associates with FcRγ and activates macrophages to allow them to produce inflammatory cytokines/chemokines, and that the receptor recognizes a 130-kDa protein which is a component of the small nuclear ribonucleoprotein released from dead cells (SAP130; also called "Sf3b3"). Furthermore, the present inventors found that in mice undergoing thymocyte death induced by irradiation, infiltration of neutrophils in the thymus is inhibited by administration of an anti-Mincle antibody, thus confirming an anti-inflammatory effect by suppression of Mincle in vivo.

The present inventors conducted further investigations based on these findings, and have completed the present invention.

Accordingly, the present invention is as follows:

[1] An anti-inflammatory agent comprising a substance that inhibits the expression of Mincle or the interaction of Mincle and SAP130 or FcRγ.
[2] The agent described in [1], wherein the substance that inhibits the interaction of Mincle and SAP130 is an antibody against Mincle.
[3] The agent described in [2], wherein the antibody recognizes the amino acid sequence shown by amino acid numbers 146 to 150 in the amino acid sequence of human Mincle shown by SEQ ID NO:2 or a corresponding amino acid sequence in an orthologue of another mammal.

[4] The agent described in [1], wherein the substance that inhibits the interaction of Mincle and SAP130 is a peptide comprising the amino acid sequence shown by amino acid numbers 146 to 150 in the amino acid sequence of human Mincle shown by SEQ ID NO:2 or a corresponding amino acid sequence in an orthologue of another mammal.

[5] The agent described in [1], wherein the substance that inhibits the interaction of Mincle and SAP130 is an antibody against SAP130.

[6] The agent described in [1], wherein the substance that inhibits the expression of Mincle is an antisense nucleic acid, ribozyme or siRNA against the Mincle gene.

[7] The agent described in [1], wherein the substance that inhibits the interaction of Mincle and FcRγ is an antibody against Mincle and/or FcRγ.

[8] The agent described in [1], wherein the substance that inhibits the interaction of Mincle and FcRγ binds to a site containing a conserved arginine residue in the transmembrane domain of Mincle.

[9] The agent described in any one of [1] to [8], wherein the agent is for the prevention and/or treatment of an inflammatory disease.

[10] A screening method for a substance that regulates inflammatory reactions, wherein the method comprises contacting Mincle or a fragment thereof containing an extracellular region and SAP130 in the presence and absence of a test substance, and comparing the degrees of the interaction of Mincle or the fragment thereof and SAP130 under the two conditions.

[11] A screening method for a substance that regulates inflammatory reactions, wherein the method comprises measuring and comparing the degrees of the interaction of Mincle or a fragment thereof containing an extracellular region and transmembrane region and FcRγ in a cell that expresses Mincle or the fragment thereof in the presence and absence of a test substance.

[12] The method described in [11], wherein the method comprises comparing the degrees of the interaction of Mincle or a fragment thereof and FcRγ with the activation of the signaling pathway via Mincle and FcRγ as an index.

[13] The method described in [12], wherein the method comprises using as an index the expression of a gene under the control of a promoter containing a base sequence to which a transcriptional factor that gets activated by the signaling via Mincle and FcRγ is capable of binding.

[14] The method described in any one of [11] to [13], wherein SAP130 is co-present.

[15] A screening method for a substance that regulates inflammatory reactions, wherein the method comprises measuring and comparing the amounts of Mincle or a mRNA that encodes the same in a cell that produces the protein in the presence and absence of a test substance.

[16] The method described in [15], wherein SAP130 is co-present.

[17] The method described in any one of [10] to [16], wherein the method is for selecting a substance having anti-inflammatory action.

[18] A method of detecting non-homeostatic cell death, wherein the method comprises measuring the amount of SAP130 in a sample collected from a subject animal.

Effect of the Invention

By inhibiting the expression of Mincle or the interaction of Mincle and SAP130 or FcRγ, it is possible to block FcRγ-dependent signaling to prevent inflammatory reactions stimulated by non-homeostatic cell death. It is also possible to select a substance having the action of regulating inflammatory reactions with an effect on the interaction of Mincle and SAP130 or FcRγ as an index. Alternatively, it is possible to detect non-homeostatic cell death with the release of SAP130 to the outside of cells as an index.

BRIEF DESCRIPTION OF THE DRAWINGS

FIG. 2 shows (a) the alignments of transmembrane region sequences of Mincle. The amino acid sequences of mouse (mMincle (SEQ ID NO: 18)), rat (rMincle (SEQ ID NO: 19)) and human Mincle (hMincle (SEQ ID NO: 20)) are aligned. Conserved arginine residues are shown. (b) Mincle binds to FcRγ. 293T cells, along with Flag-tagged DAP12, DAP10 and FcRγ, were transfected with mouse Mincle. Each lysate was immunoprecipitated with anti-Flag and blotted with an anti-Mincle monoclonal antibody (1B6) and anti-Flag. The whole lysate was also blotted with anti-Mincle. (c) Mincle binds to FcRγ in peritoneal macrophages. Peritoneal macrophages induced with thioglycolate were stimulated with 0.1 µg/ml LPS for 18 hours; the cell lysate was immunoprecipitated with an anti-Mincle polyclonal antibody and blotted with anti-FcRγ and anti-Mincle. (d) The R42 of Mincle is critical to the binding to FcRγ. 293T cells, along with FcRγ, were transfected with Flag-tagged Mincle wild-type and Mincle R42I. Each lysate was immunoprecipitated with anti-FcRγ (upper panel) or anti-Flag (lower panel) and blotted with the specified antibodies. (e) The R42 of Mincle is critical to the potential for signaling. 2B4 T cells, along with FcRγ, were transfected with Flag-tagged Mincle wild-type and Mincle R42I. The cells were stimulated with plate-coated anti-Flag, and IL-2 production was measured by ELISA. The data are representative of three separate experiments.

(b) The Mincle-induced activation is FcRγ-dependent. Peritoneal macrophages from wild-type, FcRγ$^{-/-}$ and MyD88$^{-/-}$ mice, induced with thioglycolate, were stimulated with a plate-coated anti-Mincle monoclonal antibody (6E2) or 100 µg/ml Zymosan, and MIP-2 production was determined by ELISA. (c) Activation of Syk and Erk upon crosslinking of Mincle. Macrophages induced with thioglycolate were stimulated with an anti-Mincle and donkey anti-rat antibody for the indicated times. Each cell lysate was blotted with the indicated antibodies. (d) FcRγ-dependent tyrosine phosphorylation via Mincle. Macrophages from an FcγRI/III-deficient mouse and an FcRγ-deficient mouse, induced with thioglycolate, were stimulated for 5 minutes as shown in (c), and blotted with anti-phosphotyrosine (pY) and anti-phospho-Erk. (e) Peritoneal macrophages from wild-type (white), FcRγ$^{-/-}$ (grey) and CARD9$^{-/-}$ (black) mice, induced with thioglycolate, were stimulated with a plate-coated anti-Mincle monoclonal antibody (6E2) or 1 ng/ml LPS. 18 hours later, MIP-2 production was determined by ELISA. (f-g) Activation of BMMφ via Mincle. BMMφ from wild-type, FcRγ$^{-/-}$ and MyD88$^{-/-}$ mice were treated with 10 ng/ml LPS for 18 hours, then washed and stimulated with 30 µg/ml immobilized anti-IgG1, anti-Mincle monoclonal antibody (1B6) or 10 ng/ml LPS for 6 hours, and MIP-2 production was determined by ELISA. The same cells were stimulated as described in (d) and blotted with anti-phospho-Syk, anti-Syk and anti-Mincle-biotin, respectively.

Figure 4:
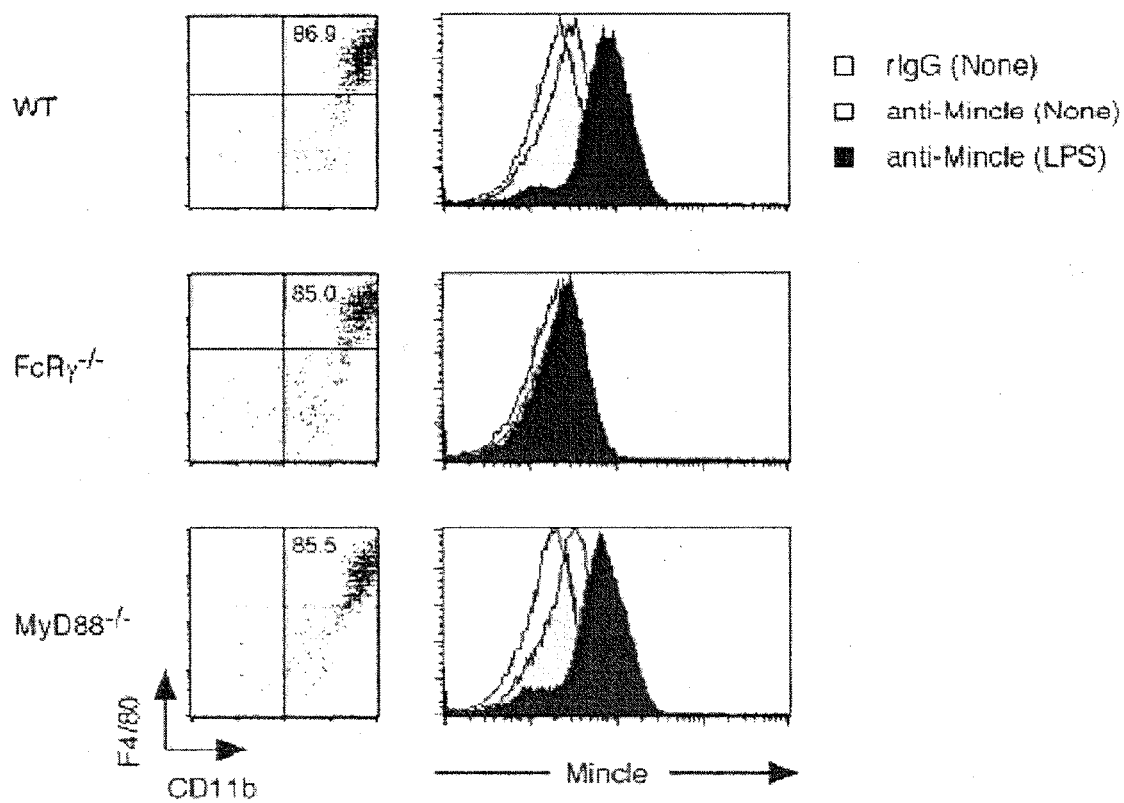

FIG. 4 shows results obtained when macrophages from the bone marrow (left panel) were allowed to stand without stimulation or stimulated with 1 ng/ml LPS for 18 hours. The cells were stained with biotinylated rat IgG1-bio (rIgG) and biotinylated anti-Mincle (1B6), as well as with Streptavidin-APC (right panel).

Figure 5:
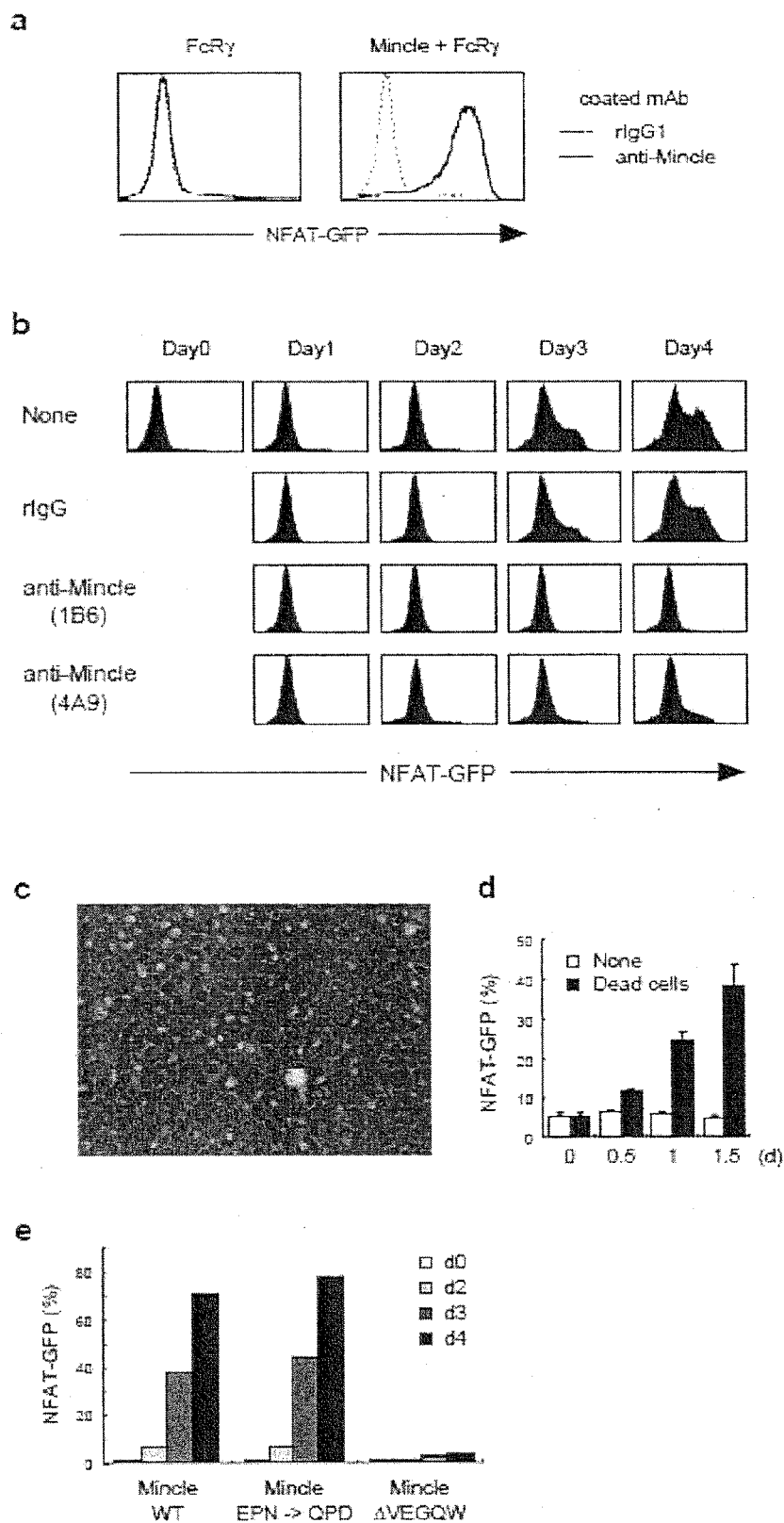

FIG. 5 shows (a) activation of NFAT-GFP with immobilized anti-Mincle. 2B4 cells expressing NFAT-GFP were transfected with FcRγ and/or Mincle. The cells were stimulated with 10 µg/ml plate-coated anti-rIgG1 (broken line) or anti-Mincle (solid line) for 18 hours, and the expression of GFP was analyzed by flow cytometry. (b) Dead cells activate NFAT-GFP via Mincle. NFAT reporter cells expressing Mincle and FcRγ were cultured in the presence or absence of 10 µg/ml rat IgG1 (rIgG), anti-Mincle clone 1B6 (1B6) or anti-Mincle clone 4A9 (4A9) without medium exchange for the indicated times. In two repeats of testing, the expression of GFP was analyzed by flow cytometry for the indicated times. The data are representative of three separate experiments. (c) GFP+ cells and dead cells in culture. Cells in (b) on day 2 of cultivation were stained with propidium iodide and analyzed using a fluorescence microscope (BZ-9000, Keyence). Typical merged images (DIC, GFP and propidium iodide are shown). (d) Etoposide-treated dead cells induce NFAT activation via Mincle. 5×10⁴ 2B4 cells were treated with 1 µg/ml etoposide for 4 hours to induce cell death and added to 5×10⁴ reporter cells. 24 hours later, IL-2 production was determined by ELISA. The data are representative of three separate experiments. (e) Not the EPN motif, but the VEGQW sequence, of Mincle is critical to dead cell-induced activation. Mincle wild-type (WT), Mincle E169Q/N171D (EPN→QPD) and Mincle ΔVEGQW (ΔVEGQW), along with FcRγ, were expressed in NFAT-GFP reporter cells. The cells were treated as in (b), and the expression of GFP was determined by flow cytometry.

Figure 6:
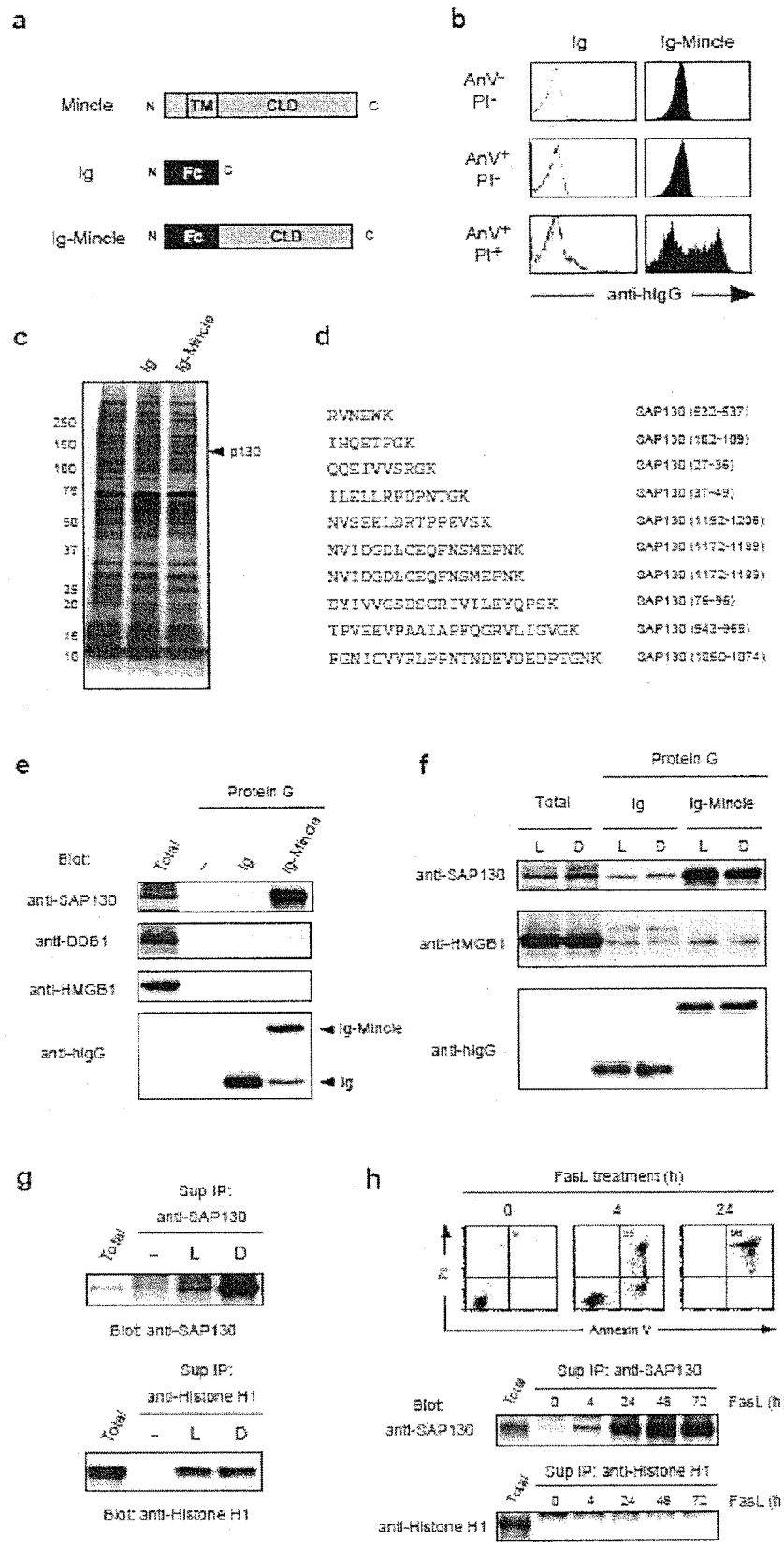

FIG. 6 shows (a) a schematic representation of Mincle, hIgG1 Fc (Ig) and the hIgG1 Fc-Mincle fusion protein (Ig-Mincle). TM, transmembrane. CLD, C-type lectin domain. (b) Ig-Mincle selectively recognizes dead cells. Thymocytes were treated with 10 µM dexamethasone for 4 hours and stained with Ig or Ig-Mincle, and with APC-labeled anti-hIgG. The cells were also stained with Annexin V-FITC (AnV) and propidium iodide (PI). (c) p130 interacts specifically with Mincle. 2B4 dead cells were lysed and subsequently pulled down using free (-), Ig-binding (Ig) and Ig-Mincle-binding (Ig-Mincle) Protein G Sepharose, and analyzed by silver staining. (d) p130 was identified as SAP130. The sequences of 10 independent peptides were analyzed by mass spectrometry (left). The positions of the individual peptides in SAP130 are shown in parentheses (right). SAP130(532-537) corresponds to SEQ ID NO: 21; SAP130(102-109) corresponds to SEQ ID NO: 22; SAP130 (27-36) corresponds to SEQ ID NO: 23; SAP130(37-49) corresponds to SEQ ID NO: 24; SAP130(1192-1205) corresponds to SEQ ID NO: 25; SAP130(1172-1189) corresponds to SEQ ID NO: 26; SAP130(76-96) corresponds to SEQ ID NO: 27; SAP130(543-565) corresponds to SEQ ID NO: 28; and SAP130(1050-1074) corresponds to SEQ ID NO: 29. (e) Western blots of Mincle-binding proteins. A 2B4 dead cell lysate was pulled down using the indicated Sepharose beads and blotted with anti-SAP130, anti-DDB1, anti-HMGB1 and anti-hIgG-HRP. The arrowheads indicate Ig-Mincle and Ig. (f) Mincle binds to SAP 130 derived from live cells. Live (L) or dead (D) 2B4 cells were pulled down using the indicated beads and blotted with the indicated antibodies. (g) SAP130 is secretable from dead cells. 2B4 cells were cultured for 1 day (live cells) or 4 days (dead cells), and the culture supernatant was recovered. The fresh medium (-), day-1 supernatant (L) and day-4 supernatant (D) were immunoprecipitated with anti-SAP130 (left panel) and anti-histone H1 (right panel). The whole lysate and each immunoprecipitate were blotted with anti-SAP and anti-Histone. (h) Release of SAP130 in Fas-mediated cell death. 2B4 expressing Fas was leucine zippered Fas ligand for the indicated times. The cells were stained with Annexin V-FITC and propidium iodide (PI) and analyzed by flow cytometry (upper panel). The supernatant from the treated cells was collected and analyzed as described in (g) (lower panel).

FIG. 7 shows (a) results obtained when proteins that interact with Mincle were sequentially purified using Protein G, Ig-Protein G and Ig-Mincle-Protein G Sepharose columns. The eluted protein was separated by SDS-PAGE, transferred to PVDF, and stained with colloidal gold. Ig-Mincle-Protein G without the cell lysate was applied as a control. The arrowhead indicates a protein detected only when Ig-Mincle-Protein G is used with the cell lysate. (b) A 130-kDa protein (p130) was excised and prepared. The digested peptide was analyzed by MALDI-TOF/MS (matrix assisted laser desorption/ionization time of flight mass spectrometry). AP 1 corresponds to SEQ ID NO: 30; AP2 corresponds to SEQ ID NO: 31; AP3 corresponds to SEQ ID NO: 32; AP4 corresponds to SEQ ID NO: 33; AP5 corresponds to SEQ ID NO: 34; AP6 and AP7 correspond to SEQ ID NO: 35; AP8 corresponds to SEQ ID NO: 36; AP9 corresponds to SEQ ID NO: 37; and AP10 corresponds to SEQ ID NO: 38. (c) p130 was identified as SAP130. The sequence from the peptide was superposed on the entire amino acid sequence of SAP130 (SEQ ID NO: 39).

Figure 8:
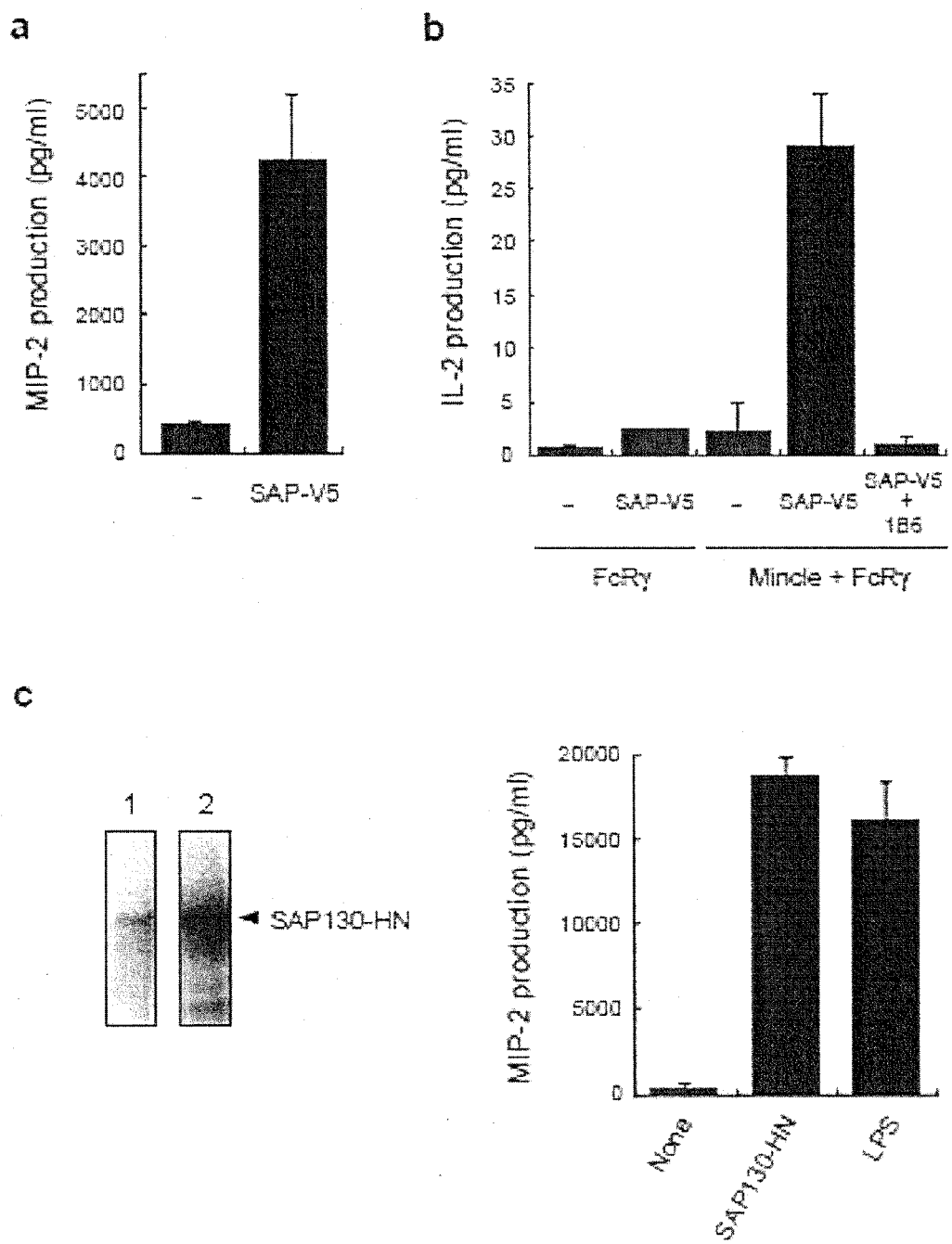

FIG. 8 shows (a) the induction of MIP-2 production by SAP130-V5 in macrophages. V5-tagged SAP130 was transfected to 293T cells. The cell lysate was applied to an anti-V5 agarose column, and the bound protein was eluted with the V5 peptide. Peritoneal macrophages induced with thioglycolate were stimulated with recombinant V5-tagged SAP130 on an anti-V5-coated plate for 18 hours. The MIP-2 concentration in the culture supernatant was determined by ELISA. (b) SAP130-V5 induces the cell activation via Mincle. NFAT reporter cells expressing FcRγ alone or both Mincle and FcRγ were stimulated with recombinant V5-tagged SAP130 in the presence or absence of 10 μg/ml anti-Mincle (1B6) on an anti-V5-coated plate for 18 hours. The IL-2 concentration in the culture supernatant was determined by ELISA. (c) Functional analysis of SAP130 expressed using baculovirus. HN-tagged SAP130 was purified from Sf9 cells using Q-Sepharose and TALON columns. The purified protein was separated by SDS-PAGE and identified by silver staining (lane 1) and anti-SAP130 blot. Macrophages induced with thioglycolate were stimulated with 0.5 μg/ml recombinant HN-tagged SAP130 (SAP130-HN) and 1 ng/ml LPS for 6 hours, and MIP-2 production was determined by ELISA (right panel).

FIG. 9 shows (a) TUNEL staining of thymuses derived from a non-treated mouse and a mouse undergoing 1-Gy irradiation (Irradiation) (GammaCell, MDS Nordion). Shown are cortical regions at 24 hours after irradiation. (b) Changes in cellularity after systemic irradiation. B6 mice underwent irradiation at 1 Gy, and total thymocyte counts (left) and the percentage of CD11b+Gr1 high neutrophils (right) were determined on the indicated days after irradiation. (c) Rapid induction of Mincle by systemic irradiation. B6 mice underwent irradiation at 1 Gy, and total RNA was extracted from the thymus at the indicated times after irradiation. On Mincle, real-time PCR analysis was performed. TLR2 and FcRγ were also analyzed as indexes of infiltration of inflammatory cells. (d-f) Anti-Mincle suppressed the infiltration of neutrophils after irradiation. 0.5 mg of rat IgG or anti-Mincle (clone 1B6 or 4A9) was administered intravenously to mice. One hour later, the same mice underwent γ-ray irradiation (1 Gy), then 12 hours later, the absolute number and cellularity of thymocytes were analyzed. On CD11b and Gr1, the thymocytes were analyzed. Absolute numbers of CD11b+Gr1 high neutrophils are shown (e). Production of MIP-2 derived from thymic macrophages was determined by ELISA (f). Each group comprised at least three mice. *, $p<0.05$.

FIG. 10 shows (a) the death of DP thymocytes by administration of dexamethasone (Dex). Each mouse was given 100 μg of Dex by intraperitoneal administration. 24 hours after administration, thymocytes were counted and the expression of CD4 and CD8 was analyzed. (b) Effect of anti-Mincle on Dex-induced neutrophil infiltration. 500 μg of rat IgG or anti-Mincle (1B6) was administered intravenously 1 hour before administration of Dex. 24 hours after administration of Dex, thymocytes were stained with anti-Gr1 and anti-CD11b. Each numerical figure shows the percentage of cells surrounded by the thymus. The percentage of the same population in the non-treated thymus was lower than 0.03%, as shown in FIG. 9d.

FIG. 11 shows (a-b) results obtained when 500 μg of anti-Mincle (1B6) was administered intravenously to B6 mice. One hour later, 10 μg of LPS was injected into the peritoneum; at 20 hours, peritoneal cells were collected and analyzed. The percentage (a) and absolute number (b) of neutrophils in the peritoneal cells are shown. Each group comprised at least four mice.

FIG. 12 shows (a) results obtained when dexamethasone-treated thymocytes were labeled with 5-chloromethylfluorescein diacetate (CMFDA). The labeled thymocytes were added to peritoneal macrophages induced with thioglycolate for 4 hours, and analyzed using a fluorescence microscope. The arrowheads indicate labeled thymocytes engulfed by the macrophages. (b) Peritoneal macrophages induced with thioglycolate were allowed to stand in a non-treated state (None), or treated with 0.1 μg/ml LPS for 8 hours to induce Mincle (LPS). Next, the labeled thymocytes were added in the presence or absence of an antibody, as indicated. Four hours later, the cells were recovered by trypsin-EDTA, and the percentage of macrophages, containing thymocytes, in the surrounded CD11b+ population was determined by flow cytometry.

FIG. 13 shows (a) a schematic representation of the splicing factor 3b subunit (SF3b) protein. The U2 snRNP complex consists of SF3b, SF3a, Sm, U2A' and U2B'. SAP49, SAP130, SAP145, SAP155 and snRNA form SF3b. The GUAGUA sequence in the U2 snRNA is well conserved among different species, forming a pair with a sequence around the branching point in the intron. (b) The samples shown in FIG. 4a were pulled down with Ig-Mincle and Protein G Sepharose, and blotted with antibodies against the U2 snRNP complex protein, such as anti-SAP49, anti-SAP145 and anti-SAP155.

MODE FOR EMBODYING THE INVENTION

"Mincle", "SAP130" and "FcRγ" in the present invention are proteins comprising the same or substantially the same amino acid sequence as the amino acid sequences shown by SEQ ID NO:2, SEQ ID NO:4 and SEQ ID NO:6, respectively. For the proteins and peptides in the present specification, the left end indicates the N-terminus (amino terminus) and the right end indicates the C-terminus (carboxyl terminus), according to the common practice of peptide designation.

These proteins may be ones isolated/purified from cells [for example, hepatocytes, splenocytes, nerve cells, glial cells, pancreatic β cells, myelocytes, mesangial cells, Langerhans' cells, epidermal cells, epithelial cells, goblet cells, endothelial cells, smooth muscle cells, fibroblasts, fibrocytes, myocytes, adipocytes, immune cells (e.g., macrophages, T cells, B cells, natural killer cells, mast cells, neutrophils, basophils, eosinophils, monocytes), megakaryocytes, synovial cells, chondrocytes, bone cells, osteoblasts, osteoclasts, mammary gland cells or interstitial cells, or corresponding precursor cells, stem cells or cancer cells thereof, and the like] of humans or other warm-blooded animals (for example, guinea pigs, rats, mice, chicken, rabbits, dogs, pigs, sheep, cattle, monkeys and the like) or any tissues where such cells are present [for example, brain or each part of brain (e.g., olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscles (e.g., smooth muscle, skeletal muscle), lung, gastrointestinal tract (e.g., large intestine, small intestine), blood vessel, heart, thymus, spleen, submandibular gland, peripheral blood, prostate, testis, ovary, placenta, uterus, bone, joint, adipose tissue (e.g., white adipose tissue, brown adipose tissue) and the like] by a method of protein separation and purification known per se.

As "substantially the same amino acid sequence as the amino acid sequence shown by SEQ ID NO:n (n=2, 4 or 6)", an amino acid sequence having a similarity of about 60% or more, preferably about 70% or more, more preferably about 80% or more, still more preferably about 90% or more, particularly preferably about 95% or more, most preferably about 97% or more, to the amino acid sequence shown by SEQ ID NO:n, and the like can be mentioned. Here, "a similarity" means a ratio (%) of identical amino acid residues and similar amino acid residues to all overlapping amino acid residues in the optimal alignment (preferably, the algorithm can consider introduction of gaps on one or both sides of the sequence for the best alignment) where two amino acid sequences are aligned using a mathematical algorithm known in the technical field. "A similar amino acid" means an amino acid having similar physiochemical properties; examples thereof include amino acids classified under the same group, such as aromatic amino acids (Phe, Trp, Tyr), aliphatic amino acids (Ala, Leu, Ile, Val), polar amino acids (Gln, Asn), basic amino acids (Lys, Arg, His), acidic amino acids (Glu, Asp), amino acids having a hydroxyl group (Ser, Thr) and amino acids having a small side-chain (Gly, Ala, Ser, Thr, Met). Substitution by such similar amino acids is expected not to change the phenotype of the protein (i.e., conservative amino acid substitution). Specific examples of the conservative amino acid substitution are known in the technical field and described in various documents (see, for example, Bowie et al., Science, 247:1306-1310 (1990)).

Amino acid sequence similarity in the present description can be calculated using the homology calculation algorithm NCBI BLAST (National Center for Biotechnology Information Basic Local Alignment Search Tool) under the following conditions (expectancy=10; gap allowed; matrix=BLOSUM62; filtering=OFF). Other algorithms to determine amino acid sequence similarity include, for example, the algorithm described in Karlin et al., Proc. Natl. Acad. Sci. USA, 90:5873-5877 (1993) [the algorithm is incorporated in the NBLAST and XBLAST programs (version 2.0) (Altschul et al., Nucleic Acids Res., 25:3389-3402 (1997))], the algorithm described in Needleman et al., J. Mol. Biol., 48:444-453 (1970) [the algorithm is incorporated in the GAP program in the GCG software package], the algorithm described in Myers and Miller, CABIOS, 4:11-17 (1988) [the algorithm is incorporated in the ALIGN program (version 2.0), which is part of the CGC sequence alignment software package], the algorithm described in Pearson et al., Proc. Natl. Acad. Sci. USA, 85:2444-2448 (1988) [the algorithm is incorporated in the FASTA program in the GCG software package] and the like; these can likewise be used preferably.

More preferably, substantially the same amino acid sequence as the amino acid sequence shown by SEQ ID NO:n is an amino acid sequence having an identity of about 60% or more, preferably about 70% or more, more preferably about 80% or more, still more preferably about 90% or more, particularly preferably about 95% or more, most preferably about 97% or more, to the amino acid sequence shown by SEQ ID NO:n.

"A protein comprising the same or substantially the same amino acid sequence as the amino acid sequence shown by SEQ ID NO:n" is a protein that comprises substantially the same amino acid sequence as the amino acid sequence shown by SEQ ID NO:n, and possesses substantially the same quality of activity as the protein consisting of the amino acid sequence shown by SEQ ID NO:n.

Here, "activity" refers to an activity to interact with SAP130 to induce the production of inflammatory cytokines and the like via FcRγ and to transport neutrophils for Mincle, to the potential for interacting with Mincle to activate Mincle for SAP130, and to an activity to induce the production of inflammatory cytokines and the like in cooperation with Mincle and to transport neutrophils for FcRγ. "Substantially the same quality" means that the properties are qualitatively the same from the viewpoint of, for example, physiology or pharmacology. Therefore, it is preferable that the activities be equivalent to each other, but quantitative factors such as the degrees of these activities (e.g., about 0.01 to about 100 times, preferably about 0.1 to about 10 times, more preferably about 0.5 to 2 times) and the molecular weight of the protein may be different.

Measurements of the interaction of Mincle and SAP130 or of Mincle and FcRγ and neutrophil trafficking activity can be performed in accordance with methods known per se; for example, these activities can be measured by, for example, the methods described in Examples below.

Mincle in the present invention also includes what are called muteins of proteins comprising an amino acid sequence having one or two or more amino acids (for example, about 1 to 30, preferably about 1 to 10, more preferably 1 to several (5, 4, 3 or 2) amino acids) substituted, deleted, inserted or added (or combinations thereof) in the amino acid sequence shown by SEQ ID NO:2. When an amino acid sequence is inserted, deleted or substituted as described above, the position of the insertion, deletion or substitution is not particularly limited, as far as the potential for interacting with SAP130 or FcRγ is retained.

Likewise, SAP130 in the present invention also includes proteins comprising an amino acid sequence having one or two or more amino acids (for example, about 1 to 50, preferably about 1 to 30, more preferably 1 to 10, still more preferably 1 to several (5, 4, 3 or 2) amino acids) substituted, deleted, inserted or added (or combinations thereof) in the amino acid sequence shown by SEQ ID NO:4. FcRγ in the present invention also includes proteins comprising an amino acid sequence having one or two or more amino acids (for example, about 1 to 30, preferably about 1 to 10, more preferably 1 to several (5, 4, 3 or 2) amino acids) substituted, deleted, inserted or added (or combinations thereof) in the amino acid sequence shown by SEQ ID NO:6.

Other preferred examples of the Mincle, SAP130 and FcRγ proteins in the present invention include various splicing variants (for example, splicing variants of human Mincle registered as Supplice Patterns (SP) 1 to SP5 in relation to CLEC4E with the Alternative Splicing Database (ASD) of GeneCards (registered trademark) and the like for Mincle; splicing variants of human SAP130 registered as SP1 to SP13 in relation to SF3B3 with ASD and the like for SAP130; splicing variants of human SAP130 registered as SP1 to SP2 in relation to FCER1G with ASD and the like), orthologues thereof in other mammals (for example, a mouse orthologue registered as RefSeq No. NP_064332 with GenBank, a rat orthologue registered as RefSeq No. NP_001005897, a chimpanzee orthologue registered as RefSeq No. XP_001135204, a canine orthologue registered as RefSeq No. XP_854311 and the like for Mincle; a mouse orthologue registered as RefSeq No. NP_598714 with GenBank, a rat orthologue registered as RefSeq No. XP_214697, a chimpanzee orthologue registered as RefSeq No. XP_511081, a canine orthologue registered as RefSeq No. XP_536791, a chicken orthologue registered as RefSeq No. XP_001232348 and the like for SAP130; a mouse orthologue registered as RefSeq No. NP_034315 with GenBank, a canine orthologue registered as RefSeq No. NP_001003171 and the like for FcRγ), naturally occurring allelic mutants or polymorphs thereof and the like.

In the present invention, "a substance that inhibits the interaction of Mincle and SAP130" may be any one capable of inhibiting the activation of Mincle upon stimulation by SAP130 and signaling in cooperation with FcRγ; preferably, a substance that inhibits the binding of Mincle and SAP130 can be mentioned.

Specifically, as an example of a substance that inhibits the binding of Mincle and SAP130, an antibody against the Mincle or SAP130 protein can be mentioned. The antibody may be a polyclonal antibody or a monoclonal antibody. These antibodies can be produced according to a method of antibody or antiserum production known per se. The isotype of the antibody is not particularly limited, and is preferably IgG, IgM or IgA, particularly preferably IgG. The antibody is not particularly limited, as far as it has at least a complementarity determining region (CDR) for specifically recognizing and binding to the target antigen; in addition to complete antibody molecules, for example, fragments such as Fab, Fab', and F(ab')$_2$, conjugate molecules prepared by gene engineering, such as scFv, scFv-Fc, minibody, and diabody, or derivatives thereof modified with molecules possessing protein stabilizing activity such as polyethylene glycol (PEG) and the like are acceptable.

Because Mincle is a cell surface receptor of the 1-pass transmembrane type, it is desirable that the anti-Mincle antibody in the present invention be one that recognizes an extracellular region of Mincle. As shown in an Example below, the region of Mincle critical to the interaction with SAP130 contains, in case of human Mincle, VEGQW (SEQ ID NO:7), which is shown by amino acid numbers 146 to 150 in the amino acid sequence shown by SEQ ID NO:2 (a corresponding amino acid sequence in an orthologue of another mammal). Therefore, preferably, the anti-Mincle antibody in the present invention is one that recognizes the region. Such an antibody can be acquired by synthesizing an oligopeptide containing the amino acid sequence of the region by a well-known method of peptide synthesis such as solid phase synthesis, conjugating this with an appropriate carrier protein, and immunizing an animal with this conjugate as an immunogen, or subjecting the animal to extracorporeal immunization using lymphocytes and the like. However, the anti-Mincle antibody in the present invention, even when recognizing a region other than the region critical to the interaction with SAP130, can likewise be used preferably, as far as it is capable of inhibiting the binding of SAP130 to Mincle to activate it by binding to SAP130.

Meanwhile, because SAP130 is released from dead cells to the outside thereof, the anti-SAP130 antibody in the present invention may recognize any region of SAP130; preferably, an antibody that recognizes a region of SAP 130 critical to the interaction with Mincle, particularly a region involved in the binding to a region containing VEGQW (SEQ ID NO:7), which is shown by amino acid numbers 146 to 150 in the amino acid sequence shown by SEQ ID NO:2, or a corresponding amino acid sequence in an orthologue of another mammal, can be mentioned.

In a preferred embodiment, because the antibody against the Mincle or SAP130 protein is used as a pharmaceutical for a human recipient, the antibody (preferably a monoclonal antibody) is an antibody having a reduced risk of exhibiting antigenicity when administered to humans, specifically a fully human antibody, a humanized antibody, a mouse-human chimera antibody or the like, and particularly preferably a fully human antibody. A humanized antibody and a chimera antibody can be prepared by gene engineering according to a conventional method. Although a fully human antibody can also be produced from a human-human (or mouse) hybridoma, it is desirable, for supplying a large amount of antibody stably and at low cost, that the antibody be produced using a human antibody-producing mouse or the phage display method.

As an example of another substance that inhibits the binding of Mincle and SAP130, a peptide can be mentioned comprising the same or substantially the same amino acid sequence as the amino acid sequence of a region of Mincle involved in the binding to SAP130. Here, "substantially the same amino acid sequence" means an amino acid sequence having 1 to 3, preferably 1 to 2, amino acids substituted, deleted, inserted or added in the amino acid sequence of a region involved in the binding to SAP130, and retaining the potential for binding to SAP130. Specifically, as the amino acid sequence of a region of Mincle involved in the binding to SAP130, VEGQW (SEQ ID NO:7), which is shown by amino acid numbers 146 to 150 in the amino acid sequence of human Mincle, which is shown by SEQ ID NO:2 above, or an amino acid sequence corresponding to the sequence in an orthologue of another mammal can be mentioned. Although the length of the peptide is not particularly limited, taking into account the issues of the size of molecular weight, the ease of synthesis, antigenicity and the like, the length is about 5 to 50 amino acids, preferably about 5 to 30 amino acids, more preferably about 5 to 15 amino acids. The peptide may comprise an amino acid sequence not involved in the binding to SAP130; for example, as far as the interaction of the amino acid sequence involved in the binding and SAP130 is not adversely influenced, an amino acid sequence designed to improve a physicochemical property (e.g., hydrophobicity, isoelectric point, thermal stability, pH stability, anti-enzyme stability and the like) of the peptide can be added to the N-terminal and/or C-terminal side of the amino acid sequence involved in the binding.

The substance that inhibits the interaction of Mincle and SAP130 in the present invention is not limited to the above-described anti-Mincle antibodies and SAP130-binding peptides; the substance may be another substance, such as a low molecular compound, as far as it directly or indirectly inhibits the interaction of Mincle and SAP130. Such a substance can be acquired by, for example, the screening method (I) or (III) of the present invention described below.

In the present invention, "a substance that inhibits the expression of Mincle" may be one that acts in any stage at the Mincle gene transcription level, post-transcriptional regulation level, translation-into-protein level, post-translational modification level and the like. Therefore, examples of a substance that inhibits the expression of the Mincle protein include a substance that inhibits the transcription of the Mincle gene, a substance that inhibits the processing from the initial transcription product into the mRNA, a substance that inhibits the translocation of the mRNA to cytoplasm, a substance that promotes the degradation of the mRNA, a substance that inhibits the translation from the mRNA into the protein, a substance that inhibits the post-translational modification of the Mincle polypeptide, and the like.

As a substance capable of specifically inhibiting the translation of the mRNA of Mincle into the protein, preferably, a nucleic acid comprising a base sequence complementary or substantially complementary to the base sequence of the mRNA or a portion thereof can be mentioned.

A base sequence substantially complementary to the base sequence of the Mincle mRNA means a base sequence having a complementarity such that the base sequence is capable of binding to the target sequence for the mRNA to inhibit the translation thereof under physiological conditions in mammalian cells; specifically, for example, the base sequence is a base sequence having a similarity of about 80% or more, preferably about 90% or more, more preferably about 95% or more, most preferably about 97% or more, with respect to the overlapping region, to a base sequence completely complementary to the base sequence of the mRNA (i.e., the base sequence of a complementary strand of the mRNA).

"Base sequence similarity" in the present invention can be calculated using the homology calculation algorithm NCBI BLAST (National Center for Biotechnology Information Basic Local Alignment Search Tool) under the following conditions (expectancy=10; gap allowed; filtering=ON; match score=1; mismatch score=−3).

More specifically, as the base sequence complementary or substantially complementary to the base sequence of the Mincle mRNA, (a) the base sequence shown by SEQ ID NO:1 or (b) a base sequence that hybridizes with the base sequence under stringent conditions, and that is complementary or substantially complementary to a sequence that encodes a protein having substantially the same quality of activity as the protein consisting of the amino acid sequence shown by SEQ ID NO:2 can be mentioned. Here, "substantially the same quality of activity" is as described above.

Examples of stringent conditions include conditions described in Current Protocols in Molecular Biology, John Wiley & Sons, 6.3.1-6.3.6, 1999, for example, hybridization with 6×SSC (sodium chloride/sodium citrate)/45° C. followed by not less than one time of washing with 0.2×SSC/0.1% SDS/50 to 65° C.; those skilled in the art can choose as appropriate hybridization conditions that give equivalent stringency.

The Mincle mRNA is preferably a human Mincle mRNA containing the base sequence shown by SEQ ID NO:1 (RefSeq Accession No. NM_014358), or an orthologue thereof in another mammal (for example, a mouse orthologue registered as RefSeq No. NM_019948 with GenBank, a rat orthologue registered as RefSeq No. NM_001005897, a chimpanzee orthologue registered as RefSeq No. XM_001135204, a canine orthologue registered as RefSeq No. XM_849218 and the like), or a naturally occurring allelic mutant or polymorph thereof.

Although "a portion of a base sequence complementary or substantially complementary to the base sequence of the Mincle mRNA" is not particularly limited with respect to the length and position thereof, as far as it is capable of binding specifically to the Mincle mRNA and capable of inhibiting the translation from the mRNA to the protein, it is preferable from the viewpoint of sequence specificity that the portion comprise at least 10 bases or more, preferably about 15 bases or more, more preferably about 20 bases or more, of a portion complementary or substantially complementary to the target sequence.

Specifically, the nucleic acid comprising a base sequence complementary or substantially complementary to the base sequence of the Mincle mRNA or a portion thereof is preferably, for example, one of the following (a) to (c).
(a) Antisense nucleic acid against the Mincle mRNA
(b) siRNA against the Mincle mRNA
(c) Nucleic acid capable of producing an siRNA against the Mincle mRNA "An antisense nucleic acid against the Mincle mRNA" in the present invention is a nucleic acid that comprises a base sequence complementary or substantially complementary to the base sequence of the mRNA or a portion thereof, and that exhibits the function to suppress protein synthesis by binding to the target mRNA to form a specific and stable double strand. The antisense nucleic acid may be a double-stranded DNA, a single-stranded DNA, a double-stranded RNA, a single-stranded RNA, or a DNA:RNA hybrid, and may have a publicly known modification added thereto. Here, "a nucleic acid" may comprise not only the purine and pyrimidine bases, but also other modified heterocyclic bases. When the antisense nucleic acid is a DNA, the RNA:DNA hybrid formed by the target RNA and the antisense DNA is capable of being recognized by endogenous RNase H to cause selective degradation of the target RNA. Therefore, in case of an antisense DNA intended to cause degradation by RNase H, the target sequence may be not only a sequence in the mRNA, but also the sequence of an intron region in the early translation product of the CPSF5 or CPSF6 gene.

Furthermore, the antisense nucleic acid of the present invention may be one capable of binding to the Mincle gene, which is a double-stranded DNA, to form a triple strand (triplex) and inhibit the transcription into RNA (antigene).

The target region for the antisense nucleic acid of the present invention is not particularly limited with respect to the length thereof, as far as hybridization of the antisense nucleic acid results in the inhibition of the translation into the Mincle protein; the target region may be a sequence of about 10 bases for the shortest or the entire sequence of the mRNA or initial transcription product for the longest. Taking into account the issues of the ease of synthesis, antigenicity and cellular translocation and the like, an oligonucleotide consisting of about 10 to about 40 bases, particularly about 15 to about 30 bases, is preferable, but this is not to be construed as limiting.

Although the nucleotide molecules that constitute the antisense nucleic acid may be naturally occurring DNAs or RNAs, the molecules can contain various chemical modifications in order to increase the stability (chemical and/or to-enzyme) or specific activity (affinity for RNA). For example, to prevent degradation by nuclease and the like, the phosphoric acid residue (phosphate) of each nucleotide that constitutes the antisense nucleic acid can be substituted with, for example, a chemically modified phosphoric acid residue such as phosphorothioate (PS), methylphosphonate, or phosphorodithionate. The hydroxyl group at the 2'-position of the sugar (ribose) of each nucleotide may be replaced with —OR (R represents, for example, $CH_3$(2'-O-Me), $CH_2CH_2OCH_3$ (2'-O-MOE), $CH_2CH_2NHC$ (NH) $NH_2$, $CH_2CONHCH_3$, $CH_2CH_2CN$ or the like). Furthermore, a base moiety (pyrimidine, purine) may be chemically modified; for example, introduction of a methyl group or a cationic functional group into the 5-position of the pyrimidine base, substitution of the 2-position carbonyl group with thiocarbonyl, and the like can be mentioned.

Regarding the conformation of the sugar moiety of RNA, two types are dominant: C2'-endo (S type) and C3'-endo (N type); in a single-stranded RNA, the sugar moiety occurs in an equilibrium of the two, but when a double strand is formed, the conformation is fixed at the N type. Therefore, BNA (LNA) (Imanishi, T. et al., Chem. Commun., 1653-9, 2002; Jepsen, J. S. et al., Oligonucleotides, 14, 130-46, 2004) and ENA (Morita, K. et al., Nucleosides Nucleotides Nucleic Acids, 22, 1619-21, 2003), which are RNA derivatives wherein the conformation of the sugar moiety is fixed at the N type by bridging the 2' oxygen and 4' carbon to confer strong bindability to the target RNA, can also be used preferably.

An antisense oligonucleotide of the present invention can be prepared by determining the target sequence on the basis of the cDNA sequence or genomic DNA sequence of Mincle, and synthesizing a sequence complementary thereto using a commercially available automated DNA/RNA synthesizer (Applied Biosystems Company, Beckman Company and the like).

Herein, a double-stranded RNA consisting of an oligo-RNA complementary to the mRNA of Mincle and a strand complementary thereto, i.e., what is called an siRNA, is also defined as being included in nucleic acids comprising a base sequence complementary or substantially complementary to the base sequence of the mRNA of Mincle or a portion thereof. An siRNA can be designed as appropriate on the basis of base sequence information on the mRNA serving as the target, using commercially available software (e.g., RNAi Designer; Invitrogen). The ribonucleoside molecules constituting the siRNA may also have the same modifications as in the above-described case of antisense nucleic acid to improve the stability, specific activity and the like. However, in case of an siRNA, it is necessary to introduce the minimally modified nucleoside allowing the RISC complex to function because a naturally occurring RNA can lose its RNAi activity if all ribonucleoside molecules therein are replaced with modified forms.

An siRNA can be prepared by synthesizing a sense chain and antisense chain of the target sequence on the mRNA using an automated DNA/RNA synthesizer, respectively, and denaturing the chains in an appropriate annealing buffer solution at about 90 to about 95° C. for about 1 minute, and thereafter annealing the chains at about 30 to about 70° C. for about 1 to about 8 hours. An siRNA can also be prepared by synthesizing a short hairpin RNA (shRNA) that serves as an siRNA precursor, and cleaving this using a dicer.

As a nucleic acid designed to be able to produce an siRNA against the mRNA of Mincle in vivo, the above-described shRNA, an expression vector constructed to express it, and the like can be mentioned. An shRNA can be prepared by designing an oligo-RNA comprising a base sequence resulting from joining of a sense chain and antisense chain of the target sequence on the mRNA with a spacer sequence having a length enabling the formation of an appropriate loop structure (for example, about 15 to 25 bases) inserted therebetween, and synthesizing this using an automated DNA/RNA synthesizer. An expression vector containing an shRNA expression cassette can be prepared by generating a double-stranded DNA that encodes the above-described shRNA by a conventional method, and thereafter inserting the DNA into an appropriate expression vector. As an shRNA expression vector, one having a Pol III system promoter such as U6 or H1 can be used. In this case, an shRNA transcribed in the animal cell incorporating the expression vector forms a loop by itself, and is thereafter processed by an endogenous enzyme dicer and the like, whereby a mature siRNA is formed.

Other preferred examples of the nucleic acid comprising a base sequence complementary or substantially complementary to the base sequence of the mRNA of Mincle or a portion thereof include ribozymes capable of specifically cleaving the mRNA in the coding region. Herein, the term ribozyme is used as a concept encompassing DNA, as far as sequence-specific nucleic acid cleavage activity is possessed. The most versatile ribozymes are self-splicing RNAs found in infectious RNAs such as viroid and virusoid, and the hammerhead type, the hairpin type and the like are known.

A nucleic acid comprising a base sequence complementary or substantially complementary to the base sequence of the mRNA of Mincle or a portion thereof can be supplied in a special form like a liposome or microspheres, and can be given in the form of an adduct with a hydrophobic substance such as a polycation like polylysine, or a lipid (e.g., phospholipids, cholesterols and the like).

The substance that inhibits the expression of Mincle in the present invention is not limited to the above-described antisense nucleic acid, siRNA, ribozyme and the like; the substance may be another substance, such as a low molecular compound, as far as it directly or indirectly inhibits the expression of Mincle. Such a substance can be acquired by, for example, the screening method (IV) of the present invention described below.

In the present invention, "a substance that inhibits the interaction of Mincle and FcRγ" may be any one, as far as it is capable of inhibiting the signaling by the activated Mincle in cooperation with FcRγ; preferably, a substance that inhibits the association of Mincle and FcRγ can be mentioned.

Specifically, as a substance that inhibits the association of Mincle and FcRγ, for example, an antibody against Mincle and/or FcRγ can be mentioned. Each antibody against Mincle or FcRγ is capable of reducing the potential for associating with the partner molecule by binding to Mincle or FcRγ to sterically inhibit the association with the partner molecule, or to result in a conformational change. A double-specific antibody that recognizes both Mincle and FcRγ can likewise be used preferably because it can block the signaling via FcRγ if binding to both antigen molecules to make them unable to approach each other to the extent that they can interact with each other. Although the regions of Mincle and FcRγ recognized by these antibodies are not particularly limited, they are preferably extracellular regions.

The antibody against Mincle and/or FcRγ may be a polyclonal antibody or a monoclonal antibody. These antibodies can be produced according to a method of antibody or antiserum production known per se. The isotype of the antibody is not particularly limited, and is preferably IgG, IgM or IgA, particularly preferably IgG. The antibody is not particularly limited, as far as it has at least a complementarity determining region (CDR) for specifically recognizing and binding to the target antigen; the same various forms as those described above can be used.

In a preferred embodiment, these antibodies are used as pharmaceuticals for human recipients, the antibodies are preferably complete human antibodies, humanized antibodies, mouse-human chimera antibodies or the like, and particularly preferably complete human antibodies.

The substance that inhibits the interaction of Mincle and FcRγ in the present invention is not limited to the above-described antibodies against Mincle and/or FcRγ; the substance may be another substance, such as a low molecular compound, as far as it directly or indirectly inhibits the interaction of Mincle and FcRγ. Such a substance can be acquired by, for example, the screening method (II) or (III) of the present invention described below.

As described in an Example below, an arginine residue well conserved among mammalian species in the transmembrane domain of Mincle (the amino acid indicated by amino acid number 41 in the amino acid sequence shown by SEQ ID NO:2) is critical to the association of Mincle and FcRγ. Therefore, a substance capable of binding specifically to a transmembrane region of Mincle containing the arginine residue is capable of effectively inhibiting the interaction of Mincle and FcRγ. Because hydrophobicity is required when a transmembrane region is targeted, it is highly advantageous to utilize a liposoluble low-molecular compound.

A substance that inhibits the expression of Mincle or the interaction of Mincle and SAP130 or FcRγ is capable of blocking FcRγ-dependent signaling to inhibit inflammatory reactions stimulated by non-homeostatic cell death. Therefore, a pharmaceutical containing a substance that inhibits the expression of Mincle or the interaction of Mincle and SAP130 or FcRγ can be used as, for example, an anti-inflammatory agent, in prophylactic and/or therapeutic agents for various inflammatory diseases (for example, Crohn disease, rheumatoic arthritis, Behçet disease (ophthalmic symptoms), ulcerative colitis, ankylosing spondylitis, psoriasis (including psoriatic arthritis), HIV infections, multiple myeloma, congestive heart failure, GVHD, giant cell arthritis (GCA), polymyalgia rheumatica (PMR), pigmentary purpura lichenoid dermatitis, sarcoidosis, Wegener granuloma, pyoderma, Behçet disease, TNF receptor-associated periodic syndrome (TRAPS), SAPHO syndrome, Takayasu disease, myositis, Still disease, periarteritis nodosa (PN), relapsing polychondritis, scleroderma polymyositis, hemophagocytosis syndrome, pemphigus, Kawasaki disease atopic dermatitis) and the like.

(1) Pharmaceutical Containing an Antibody, a Low-Molecular Compound or the Like

A pharmaceutical comprising an antibody against Mincle, SAP130 or FcRγ, or a low molecular compound that inhibits the expression of Mincle or the interaction of Mincle and SAP130 or FcRγ is of low toxicity, and can be administered as a liquid as it is, or as an appropriate dosage form of pharmaceutical composition, to humans or other mammals (e.g., mice, rats, rabbits, sheep, pigs, cattle, cats, dogs, monkeys and the like) orally or parenterally (e.g., intravascular administration, subcutaneous administration and the like).

The pharmaceutical composition used for administration may contain both the above-described antibody or low-molecular compound or a salt thereof and a pharmacologically acceptable carrier, diluent or excipient. Such a pharmaceutical composition is supplied in a dosage form suitable for oral or parenteral administration.

As examples of the composition for parenteral administration, injections, suppositories and the like are used; the injections may include dosage forms such as intravenous injections, subcutaneous injections, intracutaneous injections, intramuscular injections and drip infusion injections. Such an injection can be prepared according to a publicly known method. An injection can be prepared by, for example, dissolving, suspending or emulsifying the above-described antibody or low-molecular compound of the present invention or a salt thereof in a sterile aqueous or oily solution in common use for injections. As examples of aqueous solutions for injection, physiological saline, an isotonic solution containing glucose or another auxiliary drug, and the like can be used, which may be used in combination with an appropriate solubilizer, for example, alcohol (e.g., ethanol), polyalcohol (e.g., propylene glycol, polyethylene glycol), non-ionic surfactant [e.g., polysorbate 80, HCO-50 (polyoxyethylene (50 mol) adduct of hydrogenated castor oil)] and the like. As examples of oily solutions, sesame oil, soybean oil and the like can be used, which may be used in combination with benzyl benzoate, benzyl alcohol and the like as solubilizers. The prepared injection solution is preferably filled in an appropriate ampoule. Suppositories used for rectal administration may be prepared by mixing the above-described antibody or a salt thereof in an ordinary suppository base.

As the composition for oral administration, solid or liquid dosage forms, specifically tablets (including sugar-coated tablets and film-coated tablets), pills, granules, powders, capsules (including soft capsules), syrups, emulsions, suspensions and the like can be mentioned. Such a composition is produced by a publicly known method, and may contain a carrier, diluent or excipient in common use in the field of pharmaceutical making. Examples of carriers and excipients for tablets include lactose, starch, sucrose, and magnesium stearate.

The above-described pharmaceutical composition for parenteral or oral administration is conveniently prepared in a medication unit dosage form suitable for the dosage of the active ingredient. Examples of such medication unit dosage forms include tablets, pills, capsules, injections (ampoules), and suppositories. It is preferable that the antibody or low-molecular compound be contained at normally 5 to 500 mg, particularly 5 to 100 mg for injections, or 10 to 250 mg for other dosage forms, per medication unit dosage form.

The dose of the above-described pharmaceutical containing the above-described antibody or low-molecular compound or a salt thereof varies depending on the subject of administration, target disease, symptoms, route of administration and the like; for example, when the pharmaceutical is used for the treatment/prevention of adult rheumatoid arthritis, it is convenient to administer the antibody or low-molecular compound usually at about 0.01 to 20 mg/kg body weight, preferably about 0.1 to 10 mg/kg body weight, more preferably about 0.1 to 5 mg/kg body weight, based on a single dose, about 1 to 5 times a day, preferably about 1 to 3 times a day, by intravenous injection. In case of other modes of parenteral administration and oral administration, similar doses may be administered. In case the symptom is particularly severe, the dose may be increased according to the symptom.

Each of the aforementioned compositions may comprise any other drug that does not produce an unwanted interaction when formulated with the above-described antibody or low-molecular compound. Examples of drugs that can be used in combination with the above-described antibody and low-molecular compound include antibacterial drugs, antifungal drugs, non-steroidal anti-inflammatory drugs, steroid drugs, anticoagulant drugs, platelet aggregation inhibitors, thrombolytic drugs, immunoregulating drugs, antiprotozoan drugs, antibiotics, antiviral drugs, antitussive/expectorant drugs, sedative drugs, anesthetic drugs, anti-ulcer drugs, arrhythmia therapeutic drugs, hypotensive diuretic drugs, tranquilizers, antipsychotic drugs, antitumor drugs, antihyperlipemic drugs, muscle relaxants, antiepileptic drugs, antidepressive drugs, anti-allergic drugs, cardiotonic drugs, therapeutic drugs for arrhythmia, vasodilating drugs, vasoconstricting drugs, hypotensive diuretic drugs, therapeutic drugs for diabetes, narcotic antagonists, vitamin drugs, vitamin derivatives, therapeutic drugs for arthritis, antirheumatic drugs, anti-asthmatic drugs, therapeutic drugs for pollakiuria/urinary incontinence, therapeutic drugs for atopic dermatitis, therapeutic drugs for allergic rhinitis, hypertensive drugs, proteolytic drugs, protease inhibiting drugs, anti-SIDS drugs, antiseptic drugs, antiseptic shock drugs, endotoxin antagonists or antibodies, signaling inhibitors, inflammatory mediator action suppressing drugs, inflammatory mediator action suppressing antibodies, inflammatory mediator production suppressing drugs, anti-inflammatory mediator action suppressing drugs, anti-inflammatory mediator action suppressing antibodies, anti-inflammatory mediator production suppressing drugs, α1 adrenergic agonists and the like. The above-described antibody or low-molecular compound and these other drugs may be administered to the patient at one time or different times.

(2) Pharmaceutical Containing a Nucleic Acid Such as an Antisense Nucleic Acid, siRNA, or Ribozyme A pharmaceutical comprising an antisense nucleic acid, siRNA, or ribozyme against the Mincle mRNA or a nucleic acid that encodes the same is of low toxicity, and can be administered as a liquid as it is, or as an appropriate dosage form of pharmaceutical composition, to humans or non-human mammals (e.g., mice, rats, rabbits, sheep, pigs, cattle, cats, dogs, monkeys and the like) orally or parenterally (e.g., intravascular administration, subcutaneous administration and the like).

When these nucleic acids are used as the above-described anti-inflammatory agents, prophylactic/therapeutic agents for inflammatory diseases and the like, the same can be prepared and administered as pharmaceutical formulations according to a method known per se. Specifically, the nucleic acid of the present invention, alone or after being inserted into an appropriate expression vector for mammalian cells, such as retrovirus vector, lentivirus vector, adenovirus vector, or adeno-associated virus vector, in a functional mode, can be prepared as a pharmaceutical formulation according to a routine means. The nucleic acid can be administered as it is, or along with an auxiliary for promoting its ingestion, using a gene gun or a catheter such as a hydrogel catheter. Alternatively, the nucleic acid can be prepared as an aerosol and topically administered into the trachea as an inhalant.

Furthermore, for the purpose of improving the disposition, extending the half-life, and increasing the intracellular uptake efficiency, the aforementioned nucleic acid may be prepared as a preparation (injection) alone or with a carrier such as a liposome, and administered intravenously, subcutaneously and the like.

The nucleic acid of the present invention may be administered as it is, or as an appropriate pharmaceutical composition. The pharmaceutical composition used for administration may contain both the nucleic acid of the present invention and a pharmacologically acceptable carrier, diluent or excipient. Such a pharmaceutical composition is supplied in a dosage form suitable for oral or parenteral administration.

As examples of the composition for parenteral administration, injections, suppositories and the like are used; the injections may include dosage forms such as intravenous injections, subcutaneous injections, intracutaneous injections, intramuscular injections and drip infusion injections. Such an injection can be prepared according to a publicly known method. Suppositories used for rectal administration may be prepared by mixing the above-described nucleic acid in an ordinary suppository base.

As the composition for oral administration, solid or liquid dosage forms, specifically tablets (including sugar-coated tablets and film-coated tablets), pills, granules, powders, capsules (including soft capsules), syrups, emulsions, suspensions and the like can be mentioned. Such a composition is produced by a publicly known method, and may contain a carrier, diluent or excipient in common use in the field of pharmaceutical making. Examples of carriers and excipients for tablets include lactose, starch, sucrose, and magnesium stearate.

The above-described pharmaceutical composition for parenteral or oral administration is conveniently prepared in a medication unit dosage form suitable for the dosage of the active ingredient. Examples of such medication unit dosage forms include tablets, pills, capsules, injections (ampoules), and suppositories. It is preferable that the nucleic acid of the present invention be contained at, for example, normally 5 to 500 mg, particularly 5 to 100 mg for injections, or 10 to 250 mg for other dosage forms, per medication unit dosage form.

The dose of the above-described pharmaceutical containing the nucleic acid of the present invention varies depending on the subject of administration, target disease, symptoms, route of administration and the like; for example, when the pharmaceutical is used for the treatment/prevention of adult rheumatoid arthritis, it is convenient to administer the nucleic acid of the present invention usually at about 0.01 to 20 mg/kg body weight, preferably about 0.1 to 10 mg/kg body weight, more preferably about 0.1 to 5 mg/kg body weight, based on a single dose, about 1 to 5 times a day, preferably about 1 to 3 times a day, by intravenous injection. In case of other modes of parenteral administration and oral administration, similar doses may be administered. In case the symptom is particularly severe, the dose may be increased according to the symptom.

Each of the aforementioned compositions may comprise any other drug that does not produce an unwanted interaction when formulated with the nucleic acid of the present invention. The other drug is exemplified by the drugs mentioned above as can be used in combination with the above-described antibody and low-molecular compound.

As stated above, Mincle recognizes SAP130 released from dead cells to get activated, thus acting to interact with FcRγ to induce the production of inflammatory cytokines and the like, and to cause neutrophil infiltration. Therefore, a substance that inhibits the expression of Mincle or the interaction of Mincle and SAP130 or FcRγ can be used as an anti-inflammatory agent to prevent/treat various inflammatory diseases. Meanwhile, because a substance that enhances the expression of Mincle or the interaction of Mincle and SAP130 or FcRγ is capable of promoting the infiltration of neutrophils into damaged or pathogen-infected tissues at an appropriate level, and promoting tissue repair, it can be used as a therapeutic agent for tissue damage or an infectious disease.

Therefore, the present invention also provides a screening method for a substance that regulates inflammatory reactions by selecting a substance that regulates the expression of Mincle or the interaction of Mincle and SAP130 or FcRγ.

(I) Screening Method for a Substance that Regulates the Interaction of Mincle and SAP130

The present invention provides a screening method a substance that regulates inflammatory reactions, wherein the method comprises contacting Mincle or a fragment containing an extracellular region thereof with SAP130 in the presence or absence of a test substance, and comparing the degrees of the interaction of Mincle or a fragment thereof and SAP130 under the two conditions.

The Mincle and SAP130 proteins used in this screening method are as described in the explanation on the above-described pharmaceutical of the present invention. Regarding Mincle, the full-length thereof may be used, or a fragment thereof containing an extracellular region (in the amino acid sequence shown by SEQ ID NO:2, a region consisting of the amino acid sequence shown by amino acid numbers 45 to 219) may be used. For the SAP130 protein as well, a fragment thereof can be used, as far as the fragment contains a region involved in the binding to Mincle and the activation of Mincle. Hereinafter, unless otherwise stated, the terms Mincle and SAP130 are to be used with a meaning encompassing the above-described functional fragments.

The Mincle and SAP130 proteins can be acquired from the above-described cell or tissue that produces the proteins, using protein separation and purification techniques known per se combined as appropriate. Alternatively, these proteins can also be acquired by cloning a nucleic acid that encodes the protein from an RNA, cDNA, cDNA library or the like prepared from a cell or tissue that produces the protein, using a probe or primer prepared on the basis of the above-described base sequence information thereon, inserting the clone into an appropriate expression vector, transferring the vector into a host cell, culturing the transformant cell to obtain a recombinant protein, and recovering the protein by a method known per se. Furthermore, the same can also be synthesized chemically by a known method of peptide synthesis on the basis of the above-described amino acid sequence information on these proteins.

More specifically, this screening method comprises the following steps (a), (b) and (c):

(a) a step for contacting a test substance with Mincle and SAP130,
(b) a step for measuring the binding activity of Mincle contacted with the test substance with SAP130, and comparing the activity with the binding activity of control Mincle not contacted with the test substance and SAP130, and
(c) a step for selecting a test substance that regulates the binding activity of Mincle and SAP130 on the basis of the result of the foregoing comparison (b).

In the step (a), the test substance may be any publicly known substance or a novel substance; such substances include, for example, nucleic acids, glucides, lipids, proteins, peptides, organic low molecular compounds, compound libraries prepared using combinatorial chemistry technology, random peptide libraries prepared by solid phase synthesis or the phage display method, or naturally occurring ingredients derived from microorganisms, animals, plants, marine organisms and the like.

In the step (a), the test substance is contacted with Mincle and SAP130. In the step (a), the method of contacting is not particularly limited; examples include a method comprising mixing Mincle and SAP130 at specified concentrations under physiological conditions at 25 to 37° C., and adding a test substance, a method comprising immobilizing SAP130 to a solid phase, and binding it to Mincle in the presence of a test substance, a method comprising adding a test substance and SAP130 to a culture broth for Mincle-expressing cells, and the like. The concentration of the test substance added varies depending on the choice of compound (solubility, toxicity and the like), and can be chosen as appropriate over the range of, for example, about 0.1 nM to about 100 nM. Incubation time is, for example, about 10 minutes to about 24 hours.

In the step (b), the binding activity of Mincle and SAP130 can be measured by the methods mentioned as examples below.

b-1) A method comprising immunoprecipitation using an anti-Mincle antibody or an anti-SAP130 antibody, and Western blotting with an antibody not used in the immunoprecipitation to measure the amount of Mincle and SAP130 bound.

b-2) A method comprising expressing either Mincle or SAP130 as a fusion protein with a marker such as polyhistidine or GST, or biotinylating the same, then recovering a conjugate by utilizing the binding of polyhistidine to nickel, of GST to glutathione, or of biotin to avidin, and measuring the amount bound by Western blotting in the same manner as b-1).

b-3) A surface plasmon resonance method (Biacore).

b-4) A method comprising measuring the binding of fluorescently labeled Mincle to SAP130-expressing cells using a flow cytometer.

In the step (b), a comparison of binding activity is performed on the basis of, for example, the presence or absence of a significant difference in the amount of Mincle and SAP130 bound, in the presence and absence of a test substance.

In the step (c), a test substance that reduces or increases the binding activity of Mincle with SAP130 is selected. A test substance that has reduced the binding activity is useful as a candidate for an anti-inflammatory substance, particularly for a prophylactic/therapeutic drug for an inflammatory disease. The same is also useful as an immunoregulator or a research reagent. Meanwhile, a test substance that has increased the binding activity is useful as a candidate for a therapeutic drug for tissue damage or an infectious disease.

(II) Screening Method for a Substance that Regulates the Interaction of Mincle and FcRγ

The present invention also provides a screening method for a substance that regulates inflammatory reactions, wherein the method comprises measuring and comparing the degrees of the interaction of Mincle or a fragment thereof and FcRγ in cells expressing both Mincle or a fragment thereof containing an extracellular and transmembrane region and FcRγ, in the presence and absence of a test substance.

The Mincle and FcRγ proteins used in this screening method are as described in the explanation on the above-described pharmaceutical of the present invention. Regarding Mincle, the full-length thereof may be used, or a fragment thereof containing an extracellular region and transmembrane region (in the amino acid sequence shown by SEQ ID NO:2, a region consisting of the amino acid sequence shown by amino acid numbers 22 to 219) may be used. For the FcRγ protein as well, a fragment thereof can be used, as far as the fragment contains a region involved in the binding to Mincle and the intracellular signaling. Hereinafter, unless otherwise stated, the terms Mincle and FcRγ are to be used with a meaning encompassing the above-described functional fragments.

More specifically, this screening method comprises the following steps (a), (b) and (c):

(a) a step for contacting a test substance with a cell that expresses Mincle and FcRγ and permits a measurement of a signal transmitted by the interaction thereof (referred to as "activation signal"), (b) a step for measuring the level of the activation signal in the cell contacted with the test substance, and comparing the level with the level of the activation signal in a control cell not contacted with the test substance, and (c) a step for selecting a test substance that regulates inflammatory reactions on the basis of the result of the foregoing comparison (b).

In the step (a), the test substance used is as described above. The cell expressing Mincle and FcRγ may be a cell having endogenous Mincle and FcRγ, or may be a transformed cell incorporating either one or both. As cells expressing Mincle and FcRγ endogenously, thymocytes, macrophages, dendritic cells, glial cells, Kupffer cells, ganglion cells and the like isolated from a mammal can be mentioned. In case of transformed cells, examples of host cells include animal cells such as H4IIE-C3 cells, HepG2 cells, 293T cells, HEK293 cells, COST cells, 2B4T cells, CHO, MCF-7 cells, and H295R cells. Nucleic acids that encode Mincle and FcRγ can be prepared by isolating the protein in the same manner as the above in the screening method (I), inserting it into an expression vector having a promoter capable of functioning in the host cell, and introducing this vector into the host cell by, for example, the calcium phosphate co-precipitation method, PEG method, electroporation method, microinjection method, lipofection method and the like.

Contacting of a test substance with the above-described cell can be achieved by, for example, adding the test substance to a medium suitable for culturing the cell (for example, a minimal essential medium (MEM) containing about 5 to 20% fetal bovine serum, Dulbecco's modified Eagle medium (DMEM), RPMI 1640 medium, 199 medium, F12 medium and the like) and various buffer solutions (for example, HEPES buffer solution, phosphate buffer solution, phosphate-buffered physiological saline, Tris-HCl buffer solution, borate buffer solution, acetate buffer solution and the like), and incubating the cells for a given time. The concentration of the test substance added varies depending on the choice of compound (solubility, toxicity and the like), and can be chosen as appropriate over the range of, for example, about 0.1 nM to about 100 nM. Incubation time is, for example, about 10 minutes to about 24 hours.

In the step (b), a measurement of activation signal levels is performed by measuring the response of the cell induced as a result of the signal.

For example, a measurement of activation signals can be performed by quantifying the phosphorylation of a kinase located downstream of the signaling pathway via Mincle and FcRγ, for example, Syk, Erk, CARD9 and the like. The phosphorylation of these molecules can be quantified by performing an immunoassay such as Western blotting or ELISA on the cell lysate, using antibodies specific for respective phosphorylation products. These phosphorylation product-specific antibodies are commercially available.

A measurement of activation signals may be performed by quantifying inflammatory cytokines/chemokines such as MIP-2, TNFα, IL-6, IL-8, and IL-12, produced upon activation of the above-described signaling pathway, by, for example, an immunoassay such as Western blotting or ELISA, using antibodies thereagainst.

In still another preferred aspect, activation signal levels can be measured with the expression of a gene under the control of a promoter comprising a base sequence to which a transcriptional factor activated by the signaling via Mincle and FcRγ can bind, as an index. Such transcriptional factors include, for example, NFAT, FB, and the like. A consensus cis-sequence to which these transcriptional factors bind is well known in the art. Provided that an expression vector having a DNA that encodes a reporter protein (for example, luciferase, GFP, peroxidase, alkaline phosphatase and the like) joined thereto downstream of a promoter containing the cis-sequence, is introduced into a cell that expresses Mincle and FcRγ, the expression of the reporter protein is induced upon activation of a transcriptional factor that activates the cis-sequence by the activation signal by the method described above; therefore it is possible to quantify the activation signal level by measuring it.

In the step (b), a comparison of activation signal levels is performed on the basis of the presence or absence of a significant difference in activation signal level in the presence and absence of a test substance. Although the activation signal level in the control cell not contacted with the test substance may be an amount expressed measured before or simultaneously with the measurement of the activation signal level in the cell contacted with the test substance, it is preferable, from the viewpoint of experimental accuracy and reproducibility, that the former amount expressed be a simultaneously measured amount expressed.

In the step (c), a test substance that reduces or increases the activation signal level via the interaction of Mincle and FcRγ is selected. A test substance that has reduced the activation signal level is useful as a candidate for an anti-inflammatory substance, particularly for a prophylactic/therapeutic drug for an inflammatory disease. The same is also useful as an immunoregulator or a research reagent. Meanwhile, a test substance that has increased the activation signal level is useful as a candidate for a therapeutic drug for tissue damage or an infectious disease.

(III) Screening Method for a Substance that Regulates the Interaction of Mincle and SAP130 or FcRγ

In the above-described screening method (II), by performing contacting of the test substance and the cell in the presence of SAP130, it is possible to screen for a substance that regulates the interaction of Mincle and SAP130, in addition to a substance that regulates the interaction of Mincle and FcRγ. In this screening method as well, a test substance that has reduced the activation signal level is likewise selected as a candidate for an anti-inflammatory substance, particularly for a prophylactic/therapeutic drug for an inflammatory disease. Meanwhile, a test substance that has increased the activation signal level is selected as a candidate for a therapeutic drug for tissue damage or an infectious disease. Whether the selected substance influences the interaction of Mincle and SAP130 or the interaction of Mincle and FcRγ can be confirmed by, for example, using this method in combination with the above-described screening method (I) or (II).

(IV) Screening Method for a Substance that Regulates the Expression of Mincle

The present invention also provides a screening method for a substance that regulates inflammatory reactions, comprising measuring and comparing the amount of the Mincle protein or the mRNA that encodes the same in a Mincle-producing cell in the presence and absence of a test substance.

More specifically, the screening method of the present invention for a substance that regulates the expression of Mincle comprises the following steps (a), (b) and (c):

(a) a step for contacting a test substance and a cell permitting a measurement of the expression of Mincle,
(b) a step for measuring the amount of Mincle expressed in the cell contacted with the test substance, and comparing the amount expressed with the amount of Mincle expressed in a control cell not contacted with the test substance, and
(c) a step for selecting a test substance that reduces the amount of Mincle expressed on the basis of the result of the foregoing comparison (b).

In the step (a), the test substance is as described above. As a cell permitting a measurement of the expression of Mincle, all cultured cells expressing Mincle, whether endogenous or exogenous, or cells containing a reporter gene under the control of an endogenous promoter of the Mincle gene, and the like can be mentioned. Whether these genes are expressed in the cultured cells can easily be determined by detecting the expression of these genes by a publicly known Northern blot method or RT-PCR method.

A cell permitting a measurement of the expression of Mincle can be supplied in the form of a Mincle-producing tissue or organ isolated from a non-human mammal, or of a non-human mammal individual. Alternatively, the cell may be a cell, tissue, organ, or individual of a transgenic animal incorporating a reporter gene under the control of an endogenous promoter of the Mincle gene.

When the cell is supplied in the form of a cultured cell, an isolated tissue or organ, or the like, contacting of the test substance and the cell can be performed as described above. Meanwhile, when the cell is supplied in the form of an animal individual, contacting of the test substance and the cell is performed by administration of the test substance to the animal. The route of administration is not particularly limited; for example, intravenous administration, intra-arterial administration, subcutaneous administration, intracutaneous administration, intraperitoneal administration, oral administration, intratracheal administration, rectal administration and the like can be mentioned. The dose is not particularly limited; for example, a single dose can be administered at about 0.5 to 20 mg/kg 1 to 5 times a day, preferably 1 to 3 times a day, for 1 to 14 days.

In the step (b), a measurement of the amount of Mincle expressed is performed on the mRNA or protein. The amount of the mRNA expressed is measured by, for example, preparing total RNA from the cell, and performing RT-PCR, Northern blotting or the like. The amount of the protein expressed can be measured by, for example, preparing an extract from the cell, and performing an immunological technique. Useful immunological techniques include Western blotting method, radioimmunoassay method (RIA method), ELISA method, fluorescent antibody method and the like. When using a cell containing a reporter gene joined downstream of a promoter of the Mincle gene (for example, luciferase, GFP), the amount expressed is measured on the basis of the signal intensity of the reporter protein.

As shown in an Example below, the expression of the Mincle gene is induced by the presence of SAP130. Therefore, by performing contacting of the test substance and the cell in the presence of SAP130 in the step (a), it is possible to screen for a substance capable of regulating the expression of the Mincle gene induced by stimulation with SAP130. As a method of allowing the co-presence of SAP130 in the step (a), addition of SAP130 to the medium can be mentioned when the cell is supplied in the form of a cultured cell or the like; however, the same can be achieved by partially inducing cell death by adding a cell undergoing non-homeostatic cell death induced by radiation and the like, or irradiating a cell permitting a measurement of the expression of Mincle with an appropriate amount of radiation or the like. Meanwhile, when the cell is supplied in the form of an animal individual, SAP130 can be supplied by partially inducing cell death by irradiating the animal and the like.

When RNA is utilized as an analyte, specifically, the screening method of the present invention can be performed by preparing a primer or probe on the basis of the sequence of the Mincle gene by a publicly known method, and detecting an increase in the amount of the RNA or the transcription product thereof bound to the aforementioned disease marker as an index by a Northern blot method, RT-PCR method, DNA chip analysis, in situ hybridization analysis method or the like.

When a Northern blot method is utilized, it is possible to detect and measure the presence or absence of the expression of the Mincle gene and the expression level by using the above-described probe of the present invention. Specifically, a method can be mentioned as an example wherein the above-described probe (complementary strand) is labeled with a radioisotope (RI), a fluorescent substance or the like, and it is hybridized with an RNA derived from the above-described cell, previously transferred to a nylon membrane or the like according to a conventional method, after which a signal from a label of a disease marker (RI or fluorescent substance) in the resulting double-strand of the above-described probe (DNA) and RNA is detected and measured using a radiation detector (BAS-1800II, produced by FUJIFILM Corporation) or a fluorescence detector. It is also possible to use a method comprising labeling the above-described probe (probe DNA) using the Alk Phos Direct Labelling and Detection System (produced by Amersham Pharamcia Biotech Company) according to the protocol, hybridizing it with an RNA derived from a living tissue of the subject, thereafter detecting and measuring a signal from a labeling disease marker using the multibioimager STORM860 (produced by Amersham Pharmacia Biotech Company).

When an RT-PCR method is utilized, it is possible to detect and measure the presence or absence of the expression of the Mincle gene and expression level in RNA by using a polynucleotide having at least 15 continuous bases in the base sequence of the Mincle gene and/or a polynucleotide complementary thereto as a primer. Specifically, a method can be mentioned as an example, wherein a cDNA is prepared from the RNA of the above-described cell according to a conventional method, this as a template is hybridized with a pair of primers (an orthodox strand that binds to the above-described cDNA (− strand), a heterodox strand that binds to the + strand) prepared to allow the target region of the Mincle gene to be amplified, a PCR method is performed according to a conventional method, and the resulting amplified double-stranded DNA is detected. Detection of the amplified double-stranded DNA can be achieved by a method comprising detecting a labeled double-stranded DNA produced by performing the above-described PCR using a primer previously labeled with an RI or a fluorescent substance, a method comprising transferring the produced double-stranded DNA to a nylon membrane or the like according to a conventional method, and hybridizing the DNA with a labeled disease marker as a probe and detecting it, and the like. The resulting labeled double-stranded DNA product can be measured using the Agilent 2100 bioanalyzer (produced by Yokogawa Analytical Systems Company) and the like. It is also possible to prepare an RT-PCR reaction liquid using SYBR Green RT-PCR Reagents (produced by Applied Biosystems Company) according to the protocol, carry out a reaction using the ABI PRISM 7700 Sequence Detection System (produced by Applied Biosystems Company), and detect the reaction product.

When DNA chip analysis is utilized, a method can be mentioned comprising preparing a DNA chip coupled with a partial sequence of the Mincle gene as a DNA probe (single-stranded or double-stranded), hybridizing the chip with, for example, a cRNA prepared from an RNA derived from the above-described cells by a conventional method and labeled with biotin, and detecting the resulting double-strand of DNA and cRNA using fluorescently labeled avidin.

When in situ hybridization is utilized, the above-described cells are fixed and embedded, and a section is prepared. A specific antisense probe or sense probe of the Mincle gene is prepared. This probe is labeled with an RI marker or a non-RI marker (for example, DIG marker). The section is deparaffinized (in case of a paraffin section) and pre-treated, and thereafter fixed in ethanol and the like. The fixed section is pre-hybridized and hybridized with the probe, after which washing and an RNase treatment are performed, and the presence or absence of the expression of the Mincle gene or the expression level thereof in the living tissue can be detected and measured by a method of detection suitable for the marker (for example, development in case of an RI marker, immunological detection and microscopy in case of an non-RI marker).

When a protein is utilized as an analyte, specifically, the screening method of the present invention can be performed by confirming an increase in the amount of protein bound to an anti-Mincle antibody by a Western blot method, radioimmunoassay (RIA method), ELISA method, fluorescent antibody method, immunocyte staining method or the like using the antibody, as an index.

When a Western blot method is utilized, it can be performed by using an anti-Mincle antibody as a primary antibody, thereafter detecting and measuring a signal from a radioisotope, a fluorescent substance or the like of a labeled compound obtained using a secondary antibody (an antibody that binds to the primary antibody) labeled with a radioisotope such as 125I, a fluorescent substance, an enzyme such as horseradish peroxidase (HRP) or the like, using a radiation tester (BAS-1800II: produced by FUJIFILM Corporation and the like), a fluorescence detector and the like. It is also possible to use an anti-Mincle antibody as a primary antibody, then detect the antibody using the ECL Plus Western Blotting Detection System (produced by Amersham Pharmacia Biotech Company) according to the protocol, and measure the antibody using the multibioimager STORM860 (produced by Amersham Pharmacia Biotech Company).

When an immunocyte staining method is utilized, Mincle-positive cells can be measured according to the method described in Example 4 below using, for example, an antibody labeled with an enzyme and a color developing substrate thereof.

In the step (b), a comparison of the amounts expressed is made on the basis of the presence or absence of a significant difference in the amount of Mincle expressed in the presence and absence of a test substance. Although the amount of Mincle expressed in the control cell not contacted with the test substance may be an amount expressed measured before or simultaneously with the measurement of the amount of Mincle expressed in the cell contacted with the test substance, it is preferable, from the viewpoint of experimental accuracy and reproducibility, that the former amount expressed be a simultaneously measured amount expressed.

In the step (c), a test substance that reduces or increases the expression of Mincle is selected. A test substance that has reduced the expression of Mincle is useful as a candidate for an anti-inflammatory substance, particularly for a prophylactic/therapeutic drug for an inflammatory disease. The same is also useful as an immunoregulator or a research reagent. Meanwhile, a test substance that has increased the expression of Mincle is useful as a candidate for a therapeutic drug for tissue damage or an infectious disease.

A pharmaceutical comprising a substance selected by the above-described screening method (I) to (IV) is of low toxicity, and can be administered as a liquid as it is, or as an appropriate dosage form of pharmaceutical composition, to humans or non-human mammals (e.g., mice, rats, rabbits, sheep, pigs, cattle, cats, dogs, monkeys and the like) orally or parenterally (e.g., intravascular administration, subcutaneous administration and the like). The pharmaceutical composition used for administration may contain both a selected substance and a pharmacologically acceptable carrier, diluent or excipient. Such a pharmaceutical composition is supplied as a dosage form suitable for oral or parenteral administration. As the pharmacologically acceptable carrier, diluent or excipient, those described above can be used.

The dose of the above-described pharmaceutical varies depending on the subject of administration, target disease, symptoms, route of administration and the like; for example, when the pharmaceutical is used for the treatment/prevention of adult rheumatoic arthritis, it is convenient to administer the active ingredient usually at about 0.01 to 20 mg/kg body weight, preferably about 0.1 to 10 mg/kg body weight, more preferably about 0.1 to 5 mg/kg body weight, based on a single dose, about 1 to 5 times a day, preferably about 1 to 3 times a day, by intravenous injection. In case of other modes of parenteral administration and oral administration, similar doses may be administered. In case the symptom is particularly severe, the dose may be increased according to the symptom.

The present invention also provides a method of detecting non-homeostatic cell death, comprising measuring the amount of SAP130 in a sample collected from a subject animal.

Subject animals include humans and other mammals, preferably humans, or laboratory animals in common use, such as mice, rats, rabbits, dogs, and monkeys. As measurement subject samples, blood, plasma, serum, lymph, saliva, mucosa, urine, tears, semen, and synovial fluid can be mentioned.

The amount of SAP130 in a sample can be measured using, for example, an anti-SAP130 antibody, Mincle or a fragment thereof containing a region involved in the binding to SAP130. Specifically, SAP can be quantified by, for example, adding the sample liquid to a reaction vessel (microtiter plate and the like) with a first anti-SAP130 antibody or Mincle or a fragment thereof immobilized thereon, incubating the vessel for a given time, thereafter removing the liquid phase, adding a labeled second anti-SAP antibody or anti-Mincle antibody, and measuring the amount of marker bound to the solid phase. Examples of useful labeling agents include radioisotopes (for example, [$^{125}$I], [$^{131}$I], [$^{3}$H], [$^{14}$C] and the like), enzymes (for example, β-galactosidase, β-glucosidase, alkaline phosphatase, peroxidase, malate dehydrogenase), fluorescent substances (for example, fluorescamine, fluorescein isothiocyanate and the like), luminescent substances (for example, luminol, luminol derivatives, luciferin, lucigenin and the like) and the like.

It is obvious to those skilled in the art that in addition to the above-described method, the amount of SAP130 in the sample can be measured using other immunological techniques, surface plasmon resonance and the like.

As a result of the above-described measurement, if the amount of SAP130 in the sample collected from the subject animal is significantly higher than the amount of SAP130 in a sample collected from a normal control, it can be judged that non-homeostatic cell death has occurred in the body of the subject animal.

EXAMPLES

The present invention is hereinafter described in further detail by means of the following Examples, by which, however, the invention is never limited.
[Method]
Mice C57BL/6 (B6) mice were purchased from Clea Japan. B6 background FcRγ$^{-/-}$ mice were established as described in Park, S. Y. et al., J Clin Invest 102, 1229-38 (1998). CARD9$^{-/-}$ mice were established as described in Hara, H. et al., Nat Immunol 8, 619-29 (2007), and back-crossed with B6 six times. B6 background MyD88$^{-/-}$ mice were kindly supplied by S. Akira (Osaka University). FcγRI$^{-/-}$ and FcγRIII$^{-/-}$ mice were kindly supplied by J. S. Verbeek (Leiden University). All the mice were maintained in a rearing rack with a laminar flow from an air filter, and had free access to standard diet and water. All animal experiments were performed in compliance with our facility guideline.
Construction Mincle cDNA was cloned by PCR and inserted into pMX-IRES-hCD8 vectors 50. Mincle-Flag was prepared using the same primer as that described previously (Matsumoto, M. et al., J Immunol 163, 5039-48 (1999)). To construct the Ig-Mincle fusion protein, an extracellular domain of mouse Mincle (amino acids 46-214) was fused with hIgG Fc. SAP130 cDNA was cloned by PCR and inserted into pcDNA3.1-V5-His-TOPO (Invitrogen).
Antibodies A rabbit anti-Mincle polyclonal antibody was prepared against a peptide corresponding to the cytoplasm side region of mouse Mincle (amino acids 1-16). Anti-phospho-Erk Ab was purchased from Promega, anti-phospho-Syk from Cell Signaling Technology, anti-human IgG-HRP and Protein G Sepharose from Amersham Biosciences (Piscataway, N.J.), anti-rat IgG-HRP from Zymed, anti-rat IgG-PE from Jackson Immunoresearch, anti-Histone-H1 and anti-SAP145 from Santa Cruz, anti-SAP49 from Abcam, anti-SAP130 from Novus Biologicals, SAP155 from MBL, anti-DDB1 from BD Biosciences, and anti-Flag from Sigma.
Cell Stimulation Peritoneal macrophages induced with thioglycolate were stimulated with anti-Mincle and mouse anti-rat IgAbs. The cells were lysed with 1% Nonidet P-40 lytic buffer solution; immunoprecipitation and Western blotting were performed as described previously (Yamasaki, S. et al., Nat Immunol 7, 67-75 (2006)). LPS (L4516) and zymosan (Z4250) were purchased from SIGMA.
Preparation of Ig-Mincle An extracellular domain of Mincle (amino acids 46-214) was fused with the C-terminus of the hIgG Fc region lacking a termination codon by PCR, and inserted into the XhoI/NotI fragment of pME18S-SLAMsig-hIgG Fc. 293T cells were transiently transfected with pME18S-SLAMsig-hIgG Fc (Ig) or pME18S-SLAMsig-hIgG Fc-Mincle (Ig-Mincle). The cells were cultured using a protein-free medium (PFMH-II). The filtered supernatant was applied to a Protein A-Sepharose column; the bound fraction was eluted with 50 mM diethylamine and immediately neutralized with Tris-HCl (pH 7.5). The primary fraction was dialyzed against PBS, and this was used as the purified Ig fusion solution. The molecular weight and degree of purification of the protein were estimated by silver staining and Western blotting using anti-hIgG-HRP (Pierce). A leucine-zippered Fas-ligand (FasL) was kindly supplied by S. Nagata (Kyoto University).

Molecular Modeling

The sequence of Mincle was acquired from an NCBI server. The partial sequence of Mincle ranging from the 79th to 214th residue was extracted, and the three-dimensional structure thereof was predicted using an ordinary method of homology modeling. The crystalline structure of DC-SIGN (PDB-entry: 1nfd) was taken as a template for generating a homology model from the Protein Data Bank (PDB). The partial sequence of Mincle was aligned with the template protein using the NW alignment. In an attempt to obtain the appropriate alignment, the gap and Cys residue in Mincle were manually replaced to the corresponding position of the Cys residue in the template. The appropriate alignment was achieved, and the atoms of the primary chain in the target protein were assigned to the coordinates of the corresponding residue in the template protein of DC-SIGN. An insertion and deletion in the loop region were modelled by searching for a suitable structure from a fragment database generated from fragments of proteins having a publicly known structure. A side chain was constructed in the backbone of the Mincle model using the Metropolis Monte Carlo method. To optimize the structure, optimization in 2000 steps was performed by the steepest descent method using the molecular dynamic package AMBER8.

FIG. 1d was generated using ViewerLite (Accelrys).

RT-PCR

After the genomic DNA was removed by a DNase (Wako Nippon Gene) treatment, cDNA strands were generated with random primers using reverse transcriptase II (Invitrogen). Using gene-specific primers, the expression of RNA was quantified by real-time PCR, and the values were normalized by the expression of β-actin. The sequences of the gene-specific primers are as follows.

```
β-actin,
5'-TGGAATCCTGTGGCATCCATGAAAC-3'    (SEQ ID NO: 8)
                                    (forward)
5'-TAAAACGCAGCTCAGTAACAGTCCG-3';   (SEQ ID NO: 9)
                                    (reverse)

IL-6,
5'-TTCCATCCAGTTGCCTTCTTGG-3'        (SEQ ID NO: 10)
                                    (forward)
5'-CTTCATGTACTCCAGGTAG-3';          (SEQ ID NO: 11)
                                    (reverse)

TLR2,
5'-CAGCTTAAAGGGCGGGTCAGA-3'         (SEQ ID NO: 12)
                                    (forward)
5'-TGGAGACGCCAGCTCTGGCTC-3';        (SEQ ID NO: 13)
                                    (reverse)

Mincle,
5'-GCTCCAGCAGGGAACAATAG-3'          (SEQ ID NO: 14)
                                    (forward)
5'-GCCCTTTGATGGAATTCAGA-3';         (SEQ ID NO: 15)
                                    (reverse)
and FcRγ,
5'-CCTTCCCTTCCCTCTACACC-3'          (SEQ ID NO: 16)
                                    (forward)
5'-AAGGTAAGGCAGGGTGGTCT-3'.         (SEQ ID NO: 17)
                                    (reverse)
```

Statistics

All statistical analyses were performed using unpaired two-tailed Student's t-test.

Example 1

Figure 1:
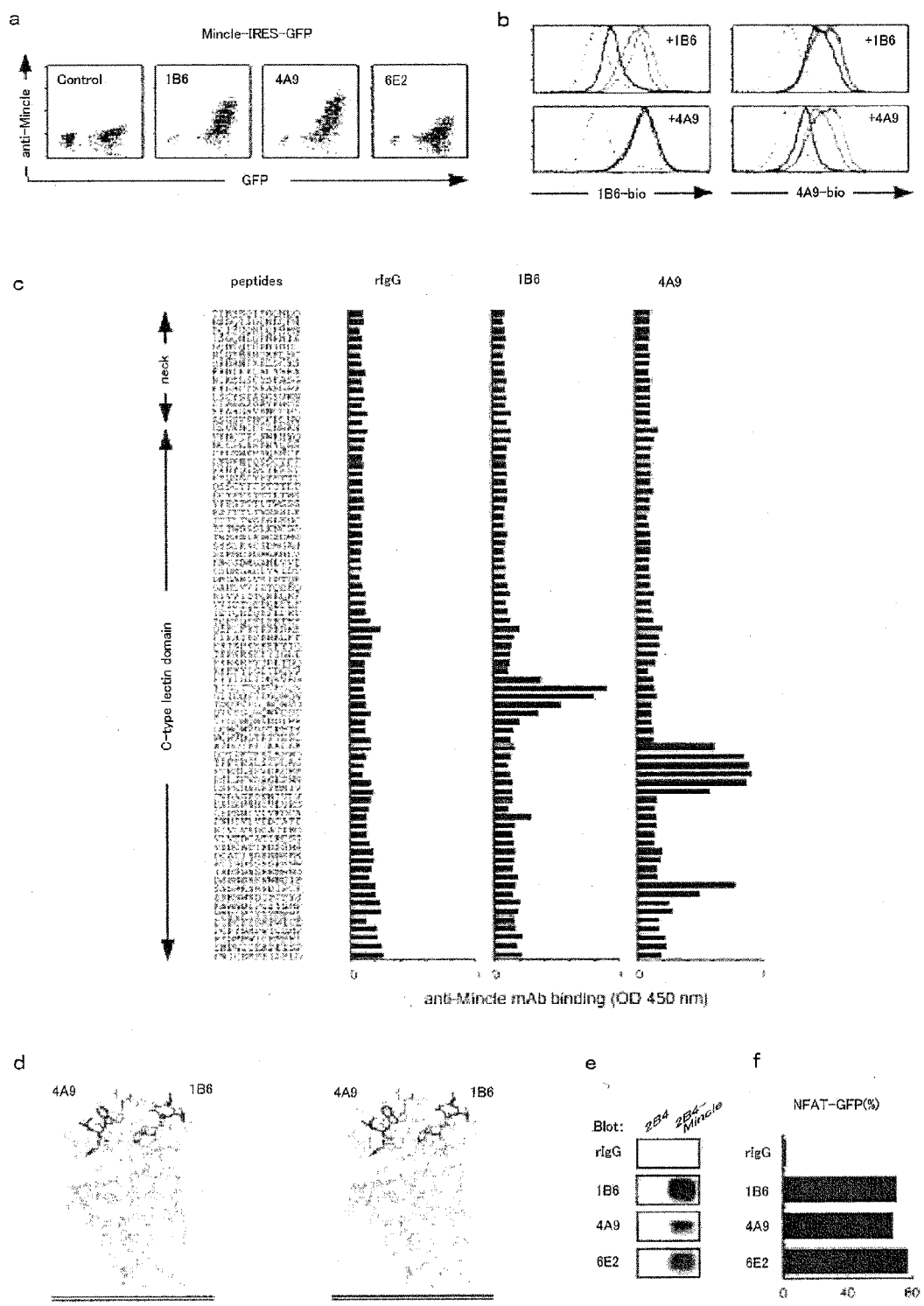
FIG. 1 shows (a) screening for an anti-Mincle monoclonal antibody by flow cytometry. 2B4 cells expressing Mincle-IRES-GFP were stained with rat IgG (control) or a hybridoma supernatant and anti-rat IgG-PE. The concentrations of the 1B6, 4A9 and 6E2 antibodies were 2.3, 1.1 and 0.05 µg/ml, respectively. (b) Binding competition. A Mincle transfectant was stained with 1 µg/ml 1B6-biotin (left) and 4A9-biotin (right) in the presence of 0 µg/ml (thin black), 1 µg/ml (grey), and 10 µg/ml (thick black) 1B6 (upper) and 4A9 (lower); subsequently Streptavidin-APC staining was performed. (c) Peptide epitope mapping. Biotinylated peptides encompassing an extracellular domain of Mincle (13 a.a in length, 11 a.a. overlapped) were synthesized. Each peptide was coated on a streptavidin-coated microplate at 0.5 nM. After blocking with BSA, rIgG, an anti-Mincle monoclonal antibody and anti-rat IgG-HRP were used as primary and secondary antibodies, respectively. Deduced epitope sequences (VEGQW for 1B6, and FWD for 4A9) are shown, respectively. (d) Molecular modeling of the 3-D structure of the extracellular domain. The VEGQW motif and FWD motif are shown, respectively. A putative mannose-binding EPN motif is shown in black. (e) A Western blot. Lysates from 2B4 cells and 2B4 cells transfected with Mincle were blotted with the anti-Mincle monoclonal antibody and anti-rat IgG-HRP. (f) Stimulatory activity. The anti-Mincle monoclonal antibody was coated at 10 µg/ml, and 2B4 cells expressing NFAT-GFP, Mincle and FcRγ were stimulated for 18 hours, and analyzed by FACS.

Wistar rats were immunized with rat basophilic leukemia (RBL-2H3) cells expressing mouse Mincle to establish anti-Mincle monoclonal antibodies. By staining 2B4 cells expressing Mincle-IRES-GFP, supernatants of cloned hybridomas were screened. Three independent clones 1B6 (IgG1, κ), 4A9 (IgG1, κ) and 6E2 (IgG2c, κ) were characterized (FIG. 1) and used in this study. The endotoxin levels in the respective monoclonal antibodies were lower than 1 EU/ml (Limulus Color KY Test, Wako). Biotinylation of the monoclonal antibodies was performed using the EZ-link biotinylation kit (Pearce) (FIG. 1).

Epitope mapping of the anti-Mincle monoclonal antibodies was performed by peptide-based ELISA. 79 biotinylated peptides encompassing an extracellular domain of Mincle (13 a.a. long, 11 a.a. overlapped) were synthesized by JPT Peptide Technologies. Each peptide at 0.5 nM was bound to a streptavidin-coated multiwell plate (PerkinElmer). After blocking with 1 μg/ml BSA, 10 μg/ml rat IgG and each anti-Mincle monoclonal antibody were added. After plate washing, 1 μg/ml anti-rat IgG-HRP was added, and color developing was performed using the TMBZ peroxidase substrate (SUMILON) (FIG. 1).

Example 2

From the alignments of the amino acid sequences of mouse, rat and human Mincle, it was found that a conserved arginine residue is present in the transmembrane domain (FIG. 2a). As described with respect to other immune receptors, it is suggested that Mincle interacts with ITAM-containing adapter molecules (FcRγ, DAP10, DAP12 and CD3ζ) because of the presence of a positively charged residue in this transmembrane portion. To determine to which of these subunits Mincle is capable of binding, Mincle, along with these adapters, was transfected to 293T. By immunoprecipitation and Western blot analysis using a newly established anti-Mincle antibody (FIG. 1), it was found that Mincle binds selectively to FcRγ but does not bind to DAP10, DAP12 and CD3ζ (FIG. 2b and data not shown). Importantly, the binding of endogenous Mincle and FcRγ was also evident in mouse peritoneal macrophages (FIG. 2c). Then, we confirmed that human Mincle also binds to FcRγ (data not shown). The interaction of Mincle and FcRγ was mediated by the $Arg^{42}$ ($R^{42}$) residue in the transmembrane region of Mincle. This is because the mutation of $R^{42}I$ (from a positive charge to neutrality) causes the binding to FcRγ to be lost, as demonstrated by the mutual immunoprecipitation (FIG. 2d). This binding seems to be critical to signaling by Mincle. This is because when Mincle and FcRγ were ectopically expressed in T cell hybridoma, the IL-2 production induced by Mincle crosslinking became dependent on $R^{42}$ (FIG. 2e). Mincle has a potential serine/threonine phosphorylation site in its cytoplasmic side region; a deletion mutant of Mincle lacking the tail portion on the C-terminal side ($Mincle^{\Delta 2-18}$) did not reduce the signaling potential in the same system (data not shown). These results suggest that Mincle is capable of signaling via FcRγ.

Example 3

Next, to determine whether endogenous Mincle can transduce an activation signal, peritoneal macrophages induced with thioglycolate were stimulated with an anti-Mincle antibody. Immobilized anti-Mincle induced the production of TNFα, MIP-2 (CXCL2) FIG. 3a), KC (CXCL1) and IL-6 (data not shown), but control IgG did not. Although there was no Mincle-induced production of inflammatory cytokines in $FcR\gamma^{-/-}$ cells, a comparable amount of cytokines were induced with FcRγ-independent LPS stimulation (FIG. 3b).

Figure 3:
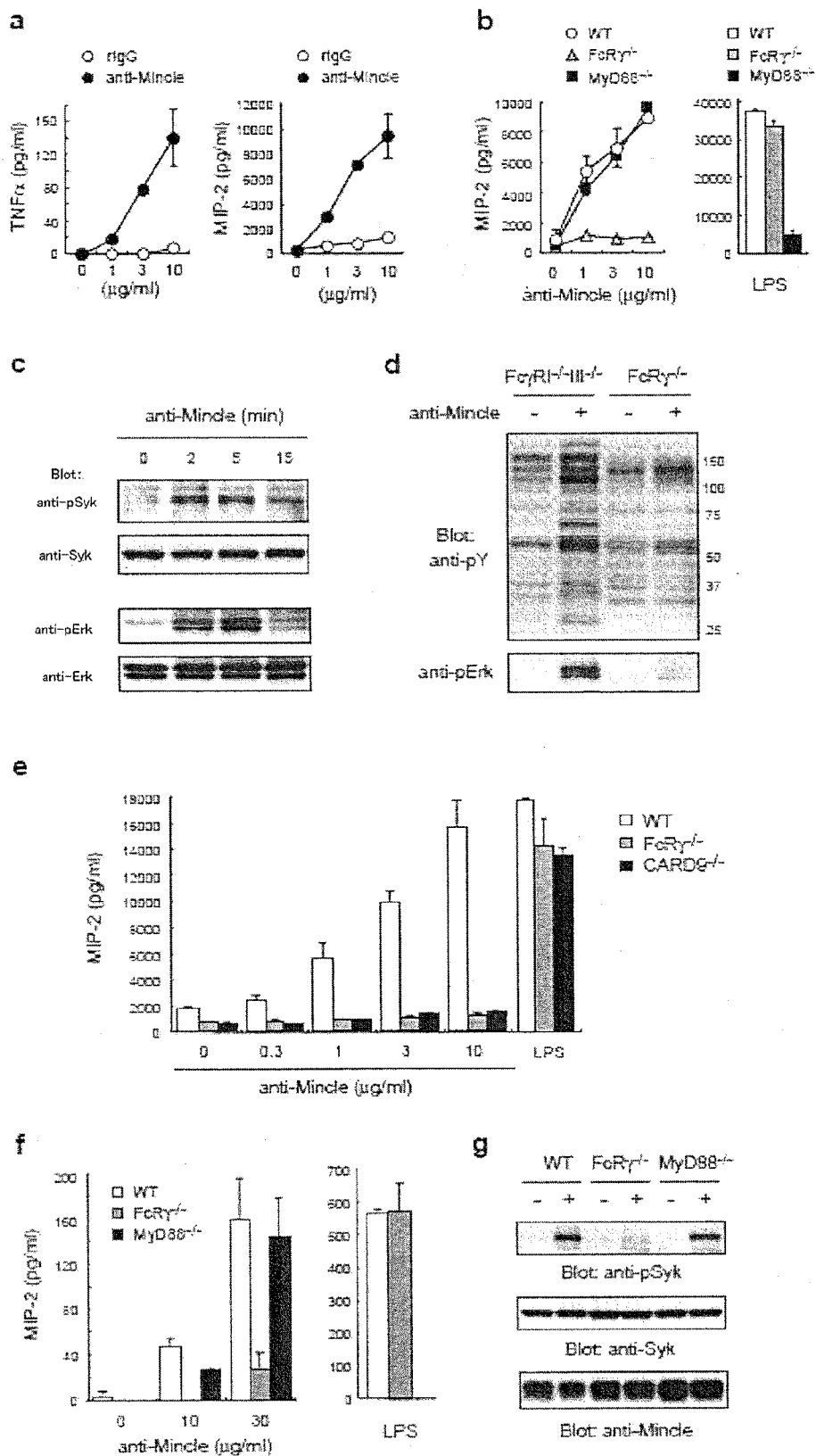
FIG. 3 shows (a) the production of TNFα and MIP-2 after Mincle ligation. Peritoneal macrophages induced with thioglycolate were stimulated with plate-coated rat IgG1 (rIgG1) or anti-Mincle monoclonal antibody (6E2) for 18 hours, and cytokine production in the culture supernatant was determined by ELISA. Similar results were obtained with other anti-Mincle monoclonal antibody clones 1B6 and 4A9.

MyD88, an adapter critical to TLR signaling, was not essential to the cytokine production via Mincle (FIG. 3b). This means that Mincle transduces activation signals to macrophages FcRγ-dependently.

Next, we examined proximal signals generated upon Mincle stimulation. The phosphorylation of cellular proteins, including the kinases Syk and Erk, in peritoneal macrophages was induced by Mincle crosslinking (FIG. 3c). In many immune receptors, Syk bound directly to phosphorylation ITAM to induce the phosphorylation of multiple downstream substrates. Therefore, the induction of the overall tyrosine phosphorylation by the anti-Mincle monoclonal antibody was remarkably suppressed in FcRγ$^{-/-}$ macrophages (FIG. 3d, right lane); this suggests that Mincle utilizes the FcRγ-Syk cascade to induce downstream signals. The phosphorylation via anti-Mincle decreases in FcRγ macrophages, but is still observable in FcγRI/III (CD64/16) double-deficient macrophages (FIG. 3d, left lane). This finding suggests that anti-Mincle, independent of the Fcγ receptor (FcγR), is involved in direct signaling via the Mincle-FcRγ complex.

Recently, it was shown that the adapter molecule CARD9 is essential to linking Syk to inflammatory reactions. For this reason, we compared reactions induced by anti-Mincle in wild-type, FcRγ$^{-/-}$ and CARD9$^{-/-}$ mouse macrophages. The production of MIP-2 induced by Mincle decreased in CARD9$^{-/-}$ peritoneal macrophages to the same extent as that in FcRγ$^{-/-}$ cells (FIG. 3e).

We also tested macrophages of bone marrow derivation (BMMφ) for Mincle signaling. Agreeing with the results for peritoneal macrophages, Mincle-mediated MIP-2 production in activated BMMφ (FIG. 3f) and Syk activation (FIG. 3g) were dependent on FcRγ, rather than on MyD88. These results suggest that Mincle activates macrophages through the FcRγ-Syk-CARD9 signaling axis.

Example 4

Although FcRγ is basically unnecessary to the surface expression of Mincle (data not shown), the enhancement of the surface expression of LPS-inducible endogenous Mincle was weaker in FcRγ$^{-/-}$ BMMφ than in the wild-type. However, interestingly, this elevation was found to be independent of MyD88 (FIG. 4).

Example 5

Next, we attempted to discover a physiological ligand of Mincle. Secretion of inflammatory cytokines and chemokines by myelogenic cells is an possible index that can be used for screening for a ligand candidate. However, such cytokines and chemokines are also produced in large amounts upon TLR stimulation. Therefore, to distinguish from the ligand of TLR that can contaminate the putative ligand of Mincle, we used a non-myelogenic T cell hybridoma as a host cell, and utilized the NFAT-GFP reporter as a means for specific detection of ITAM-mediated signals.

We established a T cell hybridoma that co-expresses Mincle, FcRγ and the NFAT-GFP reporter. Although soluble anti-Mincle did not influence the expression of GFP (data not shown), drastic expression of GFP was induced due to the crosslinking of Mincle by plate-coated anti-Mincle (FIG. 5a). As expected, no induction of GFP was observed with a TLR ligand such as LPS or zymosan (data not shown).

Interestingly, we found that when cells were cultured without medium exchange for 3 to 4 days, the expression of NFAT-GFP is remarkably induced (FIG. 5b, first panel). During this culturing period, the number of dying cells increased, and at the same time the GFP+ population increased (FIGS. 5b, c). In the cells showing the expression of only FcRγ and not showing the expression of Mincle, no expression of GFP was observed (data not shown), and NFAT activation was nearly completely inhibited by the soluble anti-Mincle monoclonal antibody (FIG. 5b, lower panel). These results suggest that a component derived from dead cells may be involved in signaling via Mincle.

Agreeing with this hypothesis, some GFP+ cells were observed in a state bound to propidium iodide (PI)-positive dead cells (FIG. 5c). The topoisomerase II inhibitor etoposide promotes cell death by inducing DNA damage. Even when etoposide-treated dead cells were simply added, Mincle-expressing cells were able to be activated (FIG. 5d). These results suggest that an unknown ligand of Mincle is produced and/or released during cell death.

Mincle contains the EPN motif, a well-investigated mannose-binding motif, in the C-type lectin domain thereof. To determine whether the recognition of dead cells by Mincle involves mannose or a related hydrocarbon, we mutated the EPN motif of Mincle to obtain the QPD motif. The QPD motif is known to bind selectively to galactose. The mutated Mincle having E169Q/N171D (Mincle EPN→QPD), like the wild-type, still transmitted the activation signal that has responded to dead cells. This finding suggests that Mincle recognizes its ligand, independently of the hydrocarbon (FIG. 5e). Certainly, a recent report has shown that C-type lectins recognize non-hydrocarbon ligands like hydrocarbon ligands. In a mutant of Mincle lacking the VEGQW sequence of an epitope recognized by the potent inhibitory monoclonal antibody 1B6 (FIG. 1), NFAT activation is lost (FIG. 5e). This finding suggests that these residues are critical to the recognition of Mincle ligands derived from dead cells.

Example 6

To further examine Mincle ligands derived from dead cells, we constructed a soluble Mincle protein. Since Mincle is a type II membrane protein, an extracellular domain of Mincle was fused with the Fc domain of human immunoglobulin G (Ig-Mincle) (FIG. 6a). First, we performed a test to determine whether Ig-Mincle specifically recognizes dead cells. Ig-Mincle bound selectively to Annexin V+ PI+ thymocytes (FIG. 6b) and dead 2B4 cells (data not shown), but control Ig did not. Therefore, the dead cells seem to express the Mincle-binding protein.

Above all, Ig-Mincle binds to dead cells without $Ca^{2+}$, despite the fact that $Ca^{2+}$ is known to be essential to lectin in recognizing a hydrocarbon-based ligand. For this reason, to identify a candidate for a Mincle ligand, we screened a Mincle-binding protein in a lysate of dead cells in the absence of $Ca^{2+}$ using Ig-Mincle. Using a reproducible method, we found a 130-kD protein (p130) to bind specifically to Ig-Mincle, but not to bind to control Ig (FIG. 6c). Hence, we the purified Mincle-binding protein by a series of column purification procedures using a lysate of dead cells (FIG. 7). Mass spectrometric analysis revealed that all the 10 peptides derived from p130 correspond to the spliceosome-binding protein 130 (SAP130, also known as Sf3b3), which is a component of the U2 small nuclear ribonucleoprotein (snRNP) 24 (FIG. 6d).

SAP130 is remarkably homologous to the damaged-DNA binding protein 1 (DDB1), which binds to UV-damaged DNA. However, immunoblotting using anti-SAP130 revealed that Ig-Mincle binds selectively to SAP130 and does not bind to DDB1 (FIG. 6e). High mobility group box 1 (HMGB1), which is a nuclear protein reported to be secreted from dead cells and act as a signal for alerting the immune system about excess or non-homeostatic cell death, is still another candidate for a Mincle ligand. However, HMGB1 did not interact with Ig-Mincle (FIGS. 6e, f) or NFAT-GFP expressing activated Mincle (data not shown). These results show that SAP130 binds selectively to Mincle.

It is possible that protein modifications such as phosphorylation, glycosylation, ubiquitination and methylation that occur in the cell death process may confer the ability of SAP130 to bind to Mincle. To verify this concept, the Mincle binding potentials of SAP130 derived from live and dead cells were compared. FIG. 6f shows that Mincle binds equally well to SAP130 derived from live and dead cells. This implies that the SAP130 signal for excess cell death is not regulated at the protein modification level.

Because SAP130 is localized in the nucleus in normal live cells, the translocation of SAP130 into the external environment upon cell death can be a alarm signal for non-homeostatic cell death. Certainly, it is known that the Sm protein, another constituent of snRNPs, translocates from late apoptotic or necrostic cells to the supernatant. Agreeing with this concept, compared with histone H1, which is still another typical nuclear protein, a substantial amount of SAP130 was released from dead cells (FIG. 6g). The release of SAP130 was also evident during Fas-ligand (Fas-L)-induced cell death, and it closely correlated with the emergence of propidium iodide (PI)+ late apoptotic/necrotic cells (FIG. 6h).

Example 7

A 2B4T cell hybridoma was cultured for 4 days to generate dead cells. 1×10$^8$ cells were lysed with 1% NP-40 lytic buffer solution (1% NP-40, 50 mM Tris, 150 mM NaCl, 5 mM EDTA, 10 µg/ml aprotinin, 12.5 µg/ml chymostatin, 50 µg/ml leupeptin, 25 µg/ml pepstatin A, 1 mM phenylmethylsulfonyl fluoride). Ig and Ig-Mincle protein were covalently bound to Protein G Sepharose 4 Fast Flow (Amersham Bioscience) using dimethyl pimelimidate (Pierce) and ethanolamine. The cell lysate was twice eluted through Protein G Sepharose, and then eluted three times through Ig-coupled Protein G Sepharose. The flowthrough fraction was applied to an Ig-Mincle-bound Protein G Sepharose column, and the column was washed with the lytic buffer solution. The bound fraction was eluted by boiling with a sample buffer solution, separated by SDS-PAGE, and subsequently transferred to PVDF and stained with Colloidal Gold Total Protein Stain (Bio-Rad). A band corresponding to p130 was excised and analyzed by MALDI-TOF/MS in Protein Research Network, Inc. (FIG. 7).

To purify SAP130 from mammalian cells, V5-tagged SAP130 was expressed in 293T cells, purified from the cell lysate using anti-V5 agarose, and subsequently eluted with the V5 peptide. To purify SAP130 expressed in baculovirus, an SAP130 cDNA was inserted into the pLP-BacPAK9-6xHN baculovirus vector (Clontech) to infect Sf9 cells with the recombinant baculovirus. The cell supernatant was purified using Q-Sepharose Fast Flow (GE Healthcare) and TALON metal affinity resins (Clontech) (FIG. 7).

Example 8

Next, we determined whether purified SAP130 was capable of activating Mincle-expressing cells. To purify recombinant SAP130 from mammalian cells, V5-tagged SAP130 was expressed in 293T cells, eluted along with the V5 peptide using anti-V5-agarose, and purified from the cell lysate. When peritoneal macrophages were stimulated with SAP130-V5 on plate-coated anti-V5, a substantial amount of MIP-2 was secreted in the supernatant (FIG. 8a). The same stimulation also induced IL-2 production from a T cell hybridoma expressing Mincle and FcRγ (FIG. 8b). This finding shows that it is minimally likely that the activity of the purified protein is due to a contaminating endotoxin. We also confirmed that SAP-130-V5 does not have an influence at all on non-Mincle-expressing parent cells (FIG. 8b). Furthermore, the SAP130-V5-induced IL-2 production by Mincle-expressing cells was nearly completely inhibited by the soluble anti-Mincle monoclonal antibody (FIG. 8b). These results suggest that SAP130 can act as an endogenous ligand of Mincle.

We also generated recombinant HN-tagged SAP130 in insect cells using a baculovirus expression vector. The recombinant SAP130 retained the immune stimulatory activity for production of MIP-2 in macrophages (FIG. 8c).

These results together imply that SAP130 is a functional ligand of Mincle. Because SAP130 is an endogenous nuclear protein, the recognition of SAP130 by Mincle can be a signal of the onset of excess cell death.

Example 9

Finally, we examined the physiological functions of Mincle in vivo. Several reports have demonstrated that transient infiltration of inflammatory cells is induced by excess or non-homeostatic cell death despite the absence of infection. A model system for investigating this phenomenon involves mouse systemic irradiation, which induces the mass death of CD4+CD8+ double-positive (DP) thymocytes in the cortical region (FIGS. 9a, b), and as a result causes transient infiltration of neutrophils into the thymus (FIG. 9b, right panel). Since it has been reported that the infiltration is reduced in mutant mice that do not undergo DP thymocyte death, such as p53$^{-/-}$ mice, this infiltration of neutrophils seems to be a result of excess cell death. We have also confirmed that infiltration of neutrophils is by far less prevalent after irradiation in apoptosis-resistant Apaf1$^{-/-}$ mice, like in Rag2$^{-/-}$ mice, which lack DP thymocytes (data not shown).

We found that the Mincle mRNA rose rapidly after systemic irradiation (FIG. 9c). Because the elevation of Mincle occurred prior to the induction of TLR2 and FcRγ, which exhibited infiltration of inflammatory cells in the thymus, this elevation was due to the transcriptional activation of Mincle (FIG. 9c).

Next, a test was performed to determine whether Mincle induces neutrophil infiltration by recognizing dead cells. The infiltration of neutrophils into the thymus after irradiation was dramatically suppressed by administration of an anti-Mincle monoclonal antibody for prevention (FIGS. 9d, e), whereas the frequency of thymocyte death did not change with the monoclonal antibody treatment (data not shown).

It has been reported that MIP-2 produced by thymic macrophages is critical to neutrophil recruitment. An anti-Mincle treatment inhibited the MIP-2 production by thymic macrophages (FIG. 9f). This finding suggests that this monoclonal antibody prevents the Mincle-ligand interaction to induce inflammatory cytokines/chemokines from macrophages.

Example 10

The infiltration of neutrophils due to dexamethasone-induced thymic cell death was also decreased by a treatment with anti-Mincle monoclonal antibody (FIG. 10). The neutrophil infiltration-preventing effect of the monoclonal antibody clone 1B6 was more potent than that of clone 4A9; this agrees with the more potent preventive effect of 1B6 on Mincle in vitro (FIG. 5b).

Example 11

Anti-Mincle did not influence the in vivo trafficking of neutrophils with LPS stimulation (FIG. 11). Therefore, infiltration of neutrophils upon thymocyte death is mostly mediated by Mincle.

Example 12

There has been increasing evidence that C-type lectin receptors are important immune receptors because they recognize various self- and non-self ligands. Although pathogenic components recognized by C-type lectins have been well described, self-ligands have not been understood so well. Roughly speaking, they seem to be molecules associated with tissue damage. For example, the endocytosis receptors MBL, Lox-1 and MGL-1 recognize ligands from dead cells, and are capable of mediating the clearance thereof. Because an anti-Mincle monoclonal antibody did not prevent the phagocytosis of dead thymocytes, Mincle does not seem to be an endocytosis receptor (FIG. 12). Although nothing has been found so far to recognize damaged self, a certain lectin receptor is capable of mediating signaling via ITAM. Therefore, Mincle is the first ITAM-coupled receptor to directly recognize dead cells.

Example 13

We identified SAP130 as a ligand of Mincle. In the U2 snRNP complex, SAP130 interacts with SAP145, SAP155 and SAP49 to form a spliceosome (FIG. 13a). Therefore, SAP155, SAP145 and SAP49 also co-precipitate with Ig-Mincle, but the efficiency is not as high as with SAP130 (FIG. 13b). Obtained using purified SAP130, our data suggests that each independently activates Mincle-expressing cells, but whether the complex formation enhances the reactivity of Mincle currently remains unknown.

INDUSTRIAL APPLICABILITY

According to the screening method of the present invention, it is possible to screen a novel anti-inflammatory agent capable of radically inhibiting inflammatory reaction activation signals. The thus-obtained anti-inflammatory agent of the present invention can be provided for the treatment of an inflammatory disease. The diagnostic method of the present invention makes it possible to diagnose the presence or absence of cell death in tissue that induces inflammatory reactions. Furthermore, it is possible to search an agonist of inflammatory reactions that can be used as a therapeutic agent that promotes the infiltration of neutrophils in damaged or pathogen-infected tissue at an appropriate level, and hence promotes tissue repair.

This application is based on a patent application No. 2008-186570 filed in Japan (filing date: Jul. 17, 2008), the contents of which are incorporated in full herein.

The invention claimed is:

1. A method of suppressing inflammatory reactions stimulated by non-homeostatic cell death, which method comprises administering to a subject a substance that inhibits the expression of Mincle or the interaction of Mincle and SAP130 or FcRγ, thereby suppressing inflammation in the subject, wherein the substance is selected from the group consisting of:

(i) an anti-Mincle antibody that inhibits the interaction of Mincle and SAP130; and (ii) an anti-Mincle antibody that inhibits the interaction of Mincle and FcRγ.

2. The method according to claim 1, wherein the anti-Mincle antibody that inhibits the interaction of Mincle and SAP130 recognizes the amino acid sequence shown by amino acid numbers 146 to 150 in the amino acid sequence of human Mincle shown by SEQ ID NO:2.

3. A method of suppressing inflammatory reactions stimulated by non-homeostatic cell death, which method comprises administering to a subject a substance that inhibits the interaction of Mincle and FcRγ, thereby suppressing inflammation in the subject, wherein the substance that inhibits the interaction of Mincle and FcRγ is an antibody against Mincle.

4. The method according to claim 1, wherein the anti-Mincle antibody that inhibits the interaction of Mincle and FcRγ binds to a site containing a conserved arginine residue in the transmembrane domain of Mincle.

5. A method for the treatment of an inflammatory disease, which method comprises administering to a subject a substance that inhibits the expression of Mincle or the interaction of Mincle and SAP 130 or FcRγ, thereby treating an inflammatory disease in the subject, wherein the substance is selected from the group consisting of:

(i) an anti-Mincle antibody that inhibits the interaction of Mincle and SAP 130; and (ii) an anti-Mincle antibody that inhibits the interaction of Mincle and FcRγ.

6. The method according to claim 1, wherein the substance is (i) an anti-Mincle antibody that inhibits the interaction of Mincle and SAP130.

7. The method according to claim 6, wherein the anti-Mincle antibody that inhibits the interaction of Mincle and SAP130 recognizes the amino acid sequence shown by amino acid numbers 146 to 150 in the amino acid sequence of human Mincle shown by SEQ ID NO:2.

8. The method according to claim 1, wherein the substance is (ii) an anti-Mincle antibody that inhibits the interaction of Mincle and FcRγ.

9. The method according to claim 8, wherein the anti-Mincle antibody that inhibits the interaction of Mincle and FcRγ binds to a site containing a conserved arginine residue in the transmembrane domain of Mincle.

10. The method according to claim 5, wherein the substance is (i) an anti-Mincle antibody that inhibits the interaction of Mincle and SAP130.

11. The method according to claim 10, wherein the anti-Mincle antibody that inhibits the interaction of Mincle and SAP130 recognizes the amino acid sequence shown by amino acid numbers 146 to 150 in the amino acid sequence of human Mincle shown by SEQ ID NO:2.

12. The method according to claim 5, wherein the substance is (ii) an anti-Mincle antibody that inhibits the interaction of Mincle and FcRγ.

13. The method according to claim 12, wherein the anti-Mincle antibody that inhibits the interaction of Mincle and FcRγ binds to a site containing a conserved arginine residue in the transmembrane domain of Mincle.

* * * * *